United States Patent
Hoshino et al.

(10) Patent No.: US 11,634,374 B2
(45) Date of Patent: Apr. 25, 2023

(54) FLUORINATED ETHER COMPOUND, FLUORINATED ETHER COMPOSITION, COATING LIQUID, ARTICLE AND ITS PRODUCTION METHOD

(71) Applicant: AGC Inc., Tokyo (JP)

(72) Inventors: Taiki Hoshino, Chiyoda-ku (JP); Makoto Uno, Chiyoda-ku (JP); Masahiro Ito, Chiyoda-ku (JP)

(73) Assignee: AGC Inc., Tokyo (JP)

( * ) Notice: Subject to any disclaimer, the term of this patent is extended or adjusted under 35 U.S.C. 154(b) by 0 days.

(21) Appl. No.: 17/469,008

(22) Filed: Sep. 8, 2021

(65) Prior Publication Data
US 2021/0403402 A1 Dec. 30, 2021

Related U.S. Application Data

(63) Continuation of application No. 16/679,454, filed on Nov. 11, 2019, now Pat. No. 11,155,508, which is a continuation of application No. PCT/JP2018/019371, filed on May 18, 2018.

(30) Foreign Application Priority Data

May 26, 2017 (JP) .............................. JP2017-104731

(51) Int. Cl.
| | |
|---|---|
| *C07C 43/12* | (2006.01) |
| *C09D 7/63* | (2018.01) |
| *C08G 65/00* | (2006.01) |
| *C09D 5/16* | (2006.01) |
| *C09D 171/00* | (2006.01) |
| *C07F 7/18* | (2006.01) |
| *B05D 7/24* | (2006.01) |
| *C08G 65/336* | (2006.01) |
| *C09K 3/18* | (2006.01) |
| *C08G 65/323* | (2006.01) |
| *C09D 5/00* | (2006.01) |

(52) U.S. Cl.
CPC .............. *C07C 43/126* (2013.01); *C09D 5/00* (2013.01); *C09D 7/63* (2018.01)

(58) Field of Classification Search
None
See application file for complete search history.

(56) References Cited

U.S. PATENT DOCUMENTS

2014/0287246 A1 9/2014 Murotani et al.
2014/0302332 A1 10/2014 Murotani et al.

FOREIGN PATENT DOCUMENTS

| CN | 104114564 A | 10/2014 |
| JP | 2005-508433 A | 3/2005 |
| WO | WO 2013/121984 A1 | 8/2013 |
| WO | WO 2013/121986 A1 | 8/2013 |

OTHER PUBLICATIONS

International Search Report dated Aug. 14, 2018 in PCT/JP2018/019371 filed on May 18, 2018.

*Primary Examiner* — Ramsey Zacharia
(74) *Attorney, Agent, or Firm* — Oblon, McClelland, Maier & Neustadt, L.L.P.

(57) ABSTRACT

To provide a fluorinated ether compound capable of forming a surface layer excellent in initial water/oil repellency, fingerprint stain removability, abrasion resistance and light resistance; a fluorinated ether composition and a coating liquid containing the fluorinated ether compound; an article having a surface layer excellent in initial water/oil repellency, fingerprint stain removability, abrasion resistance and light resistance and a method for producing it. A fluorinated ether compound having a poly(oxyperfluoroalkylene) chain having a unit ($\alpha$) which is an oxyperfluoroalkylene unit having 5 or 6 carbon atoms, and a unit ($\beta$) which is an oxyperfluoroalkylene unit having at most 4 carbon atoms, and having at least one of a hydrolysable silyl group and a silanol group on at least one terminal of the poly(oxyperfluoroalkylene) chain via a linking group.

16 Claims, No Drawings

FLUORINATED ETHER COMPOUND, FLUORINATED ETHER COMPOSITION, COATING LIQUID, ARTICLE AND ITS PRODUCTION METHOD

CROSS REFERENCE TO RELATED APPLICATIONS

This application is a continuation of U.S. application Ser. No. 16/679,454, filed on Nov. 11, 2019, which is a continuation of international patent application PCT/JP2018/019371, filed on May 18, 2018, the text of which is incorporated by reference, and claims foreign priority to Japanese Patent Application No. 2017-104731, filed on May 26, 2017, the entire content of which is incorporated herein by reference.

TECHNICAL FIELD

The present invention relates to a fluorinated ether compound, a fluorinated ether composition, a coating liquid, an article and its production method.

BACKGROUND ART

A fluorinated ether compound having a poly(oxyperfluoroalkylene) chain is capable of forming on a surface of a substrate a surface layer having high lubricity, water/oil repellency, etc. and thus is suitably used for a surface treatment agent. A surface treatment agent containing the fluorinated ether compound is used in an application where it is desired to maintain, for a long period of time, a performance (abrasion resistance) whereby water/oil repellency is less likely to be lowered even if the surface layer is rubbed repeatedly with a finger, and a performance (fingerprint stain removability) whereby a fingerprint adhering to the surface layer can be readily removed by wiping, for example, as a surface treatment agent for a member constituting the surface of a touch panel to be touched with a finger.

As a fluorinated ether compound which is capable of forming on a surface of a substrate a surface layer excellent in abrasion resistance and fingerprint stain removability, the following has been proposed.

A fluorinated ether compound which has a poly(oxyperfluoroalkylene) chain (αβ) having a $C_4$ oxyperfluoroalkylene unit (α) and an oxyperfluoroalkylene unit (β) other than the unit (α) and which has a hydrolyzable silyl group on at least one terminal of the poly(oxyperfluoroalkylene) chain (αβ) via a linking group (Patent Document 1).

PRIOR ART DOCUMENTS

Patent Document

Patent Document 1: WO2013/121986

DISCLOSURE OF INVENTION

Technical Problem

In recent years, a surface layer of a member constituting a surface to be touched by fingers of a touch panel is required to have further improved abrasion resistance and light resistance. Accordingly, a fluorinated ether compound capable of forming a surface layer excellent in fingerprint stain removability, abrasion resistance and light resistance may sometimes be required.

An object of the present invention is to provide a fluorinated ether compound capable of forming a surface layer excellent in initial water/oil repellency, fingerprint stain removability, abrasion resistance and light resistance; a fluorinated ether composition and a coating liquid containing the fluorinated ether compound; an article having a surface layer excellent in initial water/oil repellency, fingerprint stain removability, abrasion resistance and light resistance and a method for producing it.

Another object of the present invention is to provide a fluorinated ether compound useful as an intermediate of a fluorinated ether compound suitably used for a surface treatment agent.

Solution to Problem

The present invention provides a fluorinated ether compound, a fluorinated ether composition, a coating liquid, an article and a method for producing the article, having the following constructions [1] to [15].

[1] A fluorinated ether compound having a poly(oxyperfluoroalkylene) chain having a unit (α) which is an oxyperfluoroalkylene unit having 5 or 6 carbon atoms, and a unit (β) which is an oxyperfluoroalkylene unit having at most 4 carbon atoms, and having at least one of a hydrolyzable silyl group and a silanol group on at least one terminal of the poly(oxyperfluoroalkylene) chain via a linking group.

[2] The fluorinated ether compound according to [1], wherein in the poly(oxyperfluoroalkylene) chain, the proportion of the number of the unit (α) to the total number of the unit (α) and the unit (β) is from 0.02 to 0.5.

[3] The fluorinated ether compound according to [1] or [2], wherein the poly(oxyperfluoroalkylene) chain contains a structure having the unit (α) and the unit (β) alternately arranged.

[4] The fluorinated ether compound according to any one of [1] to [3], wherein the unit (α) is ($CF_2CF_2CF_2CF_2CF_2O$) or ($CF_2CF_2CF_2CF_2CF_2CF_2O$). [5] The fluorinated ether compound according to any one of [1] to [4], wherein the unit (p) is ($CF_2O$) or ($CF_2CF_2O$).

[6] The fluorinated ether compound according to anyone of [1] to [5], which is a compound represented by the following formula (11):

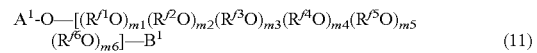

$$A^1\text{-O---}[(R^{f1}O)_{m1}(R^{f2}O)_{m2}(R^{f3}O)_{m3}(R^{f4}O)_{m4}(R^{f5}O)_{m5}(R^{f6}O)_{m6}]\text{---}B^1 \quad (11)$$

wherein $A^1$ is a $C_{1-20}$ perfluoroalkyl group or $B^1$,
$R^{f1}$ is a $C_1$ perfluoroalkylene group,
$R^{f2}$ is a $C_2$ perfluoroalkylene group,
$R^{f3}$ is a $C_3$ perfluoroalkylene group,
$R^{f4}$ is a $C_4$ perfluoroalkylene group,
$R^{f5}$ is a $C_5$ perfluoroalkylene group,
$R^{f6}$ is a $C_6$ perfluoroalkylene group,
m1, m2, m3, m4, m5 and m6 are each 0 or an integer of at least 1, m1+m2+m3+m4 is an integer of at least 1, m5+m6 is an integer of at least 1, and m1+m2+m3+m4+m5+m6 is an integer of from 2 to 200,
$B^1$ is $-Q[-SiR_nL_{3-n}]_k$,
Q is a (k+1) valent linking group,
R is a hydrogen atom or a monovalent hydrocarbon group,
L is a hydrolyzable group or a hydroxy group,
n is an integer of from 0 to 2, and
k is an integer of from 1 to 10.

[7] The fluorinated ether compound according to [6], wherein $B^1$ is a group represented by any one of the following formulae (g1) to (g7):

$$—R^{f7}—(X^1)_p-Q^1-SiR_nL_{3-n} \quad (g1)$$

$$—R^{f7}—(X^2)_r-Q^{21}-N[-Q^{22}-SiR_nL_{3-n}]_2 \quad (g2)$$

$$—R^{f7}—[C(O)N(R^{31})]_s-Q^{31}-(O)_t-C[—(O)_u-Q^{32}-SiR_nL_{3-n}]_3 \quad (g3)$$

$$—R^{f7}-Q^{41}-Si[-Q^{42}-SiR_nL_{3-n}]_3 \quad (g4)$$

$$—R^{f7}—[C(O)N(R^5)]_v-Q^{51}-Z[-Q^{52}-SiR_nL_{3-n}]_w \quad (g5)$$

$$—R^{f7}-Q^{61}-G(R^6)[-Q^{62}-SiR_nL_{3-n}]_2 \quad (g6)$$

$$—R^{f7}-Q^{71}-[CH_2C(R^{71})(-Q^{72}-SiR_nL_{3-n})]_y—R^{72} \quad (g7)$$

wherein $R^{f7}$ is a $C_{1-6}$ perfluoroalkylene group,
R is a hydrogen atom or a monovalent hydrocarbon group,
L is a hydrolyzable group or a hydroxy group,
n is an integer of from 0 to 2,
in the formula (g1),
$X^1$ is an etheric oxygen atom or $—C(O)N(R^1)—$ (provided that N is bonded to $Q^1$),
$R^1$ is a hydrogen atom or an alkyl group,
p is 0 or 1, and
$Q^1$ is an alkylene group, a group having an etheric oxygen atom or a silphenylene skeleton between carbon atoms of an alkylene group having at least 2 carbon atoms, or a group having a bivalent organopolysiloxane residue or a dialkylsilylene group between carbon atoms or at a terminal on the side bonded to $(X^1)_p$ of an alkylene group having at least 2 carbon atoms,
in the formula (g2),
$X^2$ is an etheric oxygen atom, —NH— or $—C(O)N(R^2)—$ (provided that N is bonded to $Q^{21}$),
$R^2$ is a hydrogen atom or an alkyl group,
r is 0 or 1 (provided that it is 0 when $Q^{21}$ is a single bond),
$Q^{21}$ is a single bond, an alkylene group, or a group having an etheric oxygen atom, —NH—, —C(O)—, —C(O)O— or —OC(O)— between carbon atoms of an alkylene group having at least 2 carbon atoms,
$Q^{22}$ is an alkylene group, or a group having an etheric oxygen atom, —NH— or a bivalent organopolysiloxane residue between carbon atoms of an alkylene group having at least 2 carbon atoms, and
two $[-Q^{22}-SiR_nL_{3-n}]$ may be the same or different,
in the formula (g3),
$R^{31}$ is a hydrogen atom or an alkyl group,
s is 0 or 1,
$Q^{31}$ is a single bond, an alkylene group, or a group having an etheric oxygen atom between carbon atoms of an alkylene group having at least 2 carbon atoms,
t is 0 or 1 (provided that it is 0 when $Q^{31}$ is a single bond),
u is 0 or 1,
$Q^{32}$ is an alkylene group, a group having an etheric oxygen atom or a silphenylene skeleton between carbon atoms of an alkylene group having at least 2 carbon atoms, or a group having $—C(O)N(R^{32})—$, a bivalent organopolysiloxane residue or a dialkylsilylene group between carbon atoms or at a terminal on the side bonded to $(O)_u$ of an alkylene group having at least 2 carbon atoms, $R^{32}$ is a hydrogen atom or an alkyl group, and three $[—(O)_u-Q^{32}-SiR_nL_{3-n}]$ may be the same or different,
in the formula (g4),
$Q^{41}$ is an alkylene group, or a group having an etheric oxygen atom between carbon atoms of an alkylene group having at least 2 carbon atoms,
$Q^{42}$ is an alkylene group, or a group having an etheric oxygen atom or a bivalent organopolysiloxane residue between carbon atoms of an alkylene group having at least 2 carbon atoms, and
three $[-Q^{42}-SiR_nL_{3-n}]$ may be the same or different, in the formula (g5),
$R^5$ is a hydrogen atom or an alkyl group,
v is 0 or 1,
$Q^{51}$ is an alkylene group, or a group having an etheric oxygen atom between carbon atoms of an alkylene group having at least 2 carbon atoms,
Z is a (w+1) valent organopolysiloxane residue,
$Q^{52}$ is an alkylene group, or a group having an etheric oxygen atom or a bivalent organopolysiloxane residue between carbon atoms of an alkylene group having at least 2 carbon atoms,
w is an integer of from 2 to 7, and
$w[-Q^{52}-SiR_nL_{3-n}]$ may be the same or different,
in the formula (g6),
$Q^{61}$ is a single bond, an alkylene group, or a group having an etheric oxygen atom between carbon atoms of an alkylene group having at least 2 carbon atoms,
G is a carbon atom or a silicon atom,
$R^6$ is a hydroxy group or an alkyl group,
$Q^{62}$ is an alkylene group, or a group having an etheric oxygen atom or a bivalent organopolysiloxane residue between carbon atoms of an alkylene group having at least 2 carbon atoms, and
two $[-Q^2-SiR_nL_{3-n}]$ may be the same or different, and
in the formula (g7),
$Q^{71}$ is a single bond, an alkylene group, or a group having an etheric oxygen atom between carbon atoms of an alkylene group having at least 2 carbon atoms,
$R^{71}$ is a hydrogen atom or an alkyl group,
$Q^{72}$ is a single bond or an alkylene group,
$R^{72}$ is a hydrogen atom or a halogen atom,
y is an integer of from 1 to 10, and
two to ten $[-Q^{72}-SiR_nL_{3-n}]$ may be the same or different.

[8] The fluorinated ether compound according to [6] or [7], wherein in the formula (11), $A^1$ is a $C_{1-20}$ perfluoroalkyl group, and all the $(R^{f5}O)$ and $(R^{f6}O)$ are located on the $A^1$-O-side from the $[0.5\times(m1+m2+m3+m4+m5+m6)]$th unit as counted from the $A^1$-O— side.

[9] The fluorinated ether compound according to any one of [1] to [5], which is a compound represented by the following formula (10):

$$[A^{10}-O—\{(R^{f1}O)_{m1}(R^{f2}O)_{m2})(R^{f3}O)_{m3}(R^{f4}O)_{m4}(R^{f5}O)_{m5}(R^{f6}O)_{m6}\}]_j—B^{10} \quad (10)$$

wherein $A^{10}$ is a $C_{1-20}$ perfluoroalkyl group or $B^{10}$,
$R^{f1}$ is a $C_1$ perfluoroalkylene group,
$R^{f2}$ is a $C_2$ perfluoroalkylene group,
$R^{f3}$ is a $C_3$ perfluoroalkylene group,
$R^{f4}$ is a $C_4$ perfluoroalkylene group,
$R^{f5}$ is a $C_5$ perfluoroalkylene group,
$R^{f6}$ is a $C_6$ perfluoroalkylene group,
m1, m2, m3, m4, m5 and m6 are each 0 or an integer of at least 1, m1+m2+m3+m4 is an integer of at least 1, m5+m6 is an integer of at least 1, and m1+m2+m3+m4+m5+m6 is an integer of from 2 to 200, j is an integer of from 2 to 10,
$B^{10}$ is $Q^{10}[-SiR_nL_{3-n}]_k$,
$Q^{10}$ is a (k+j) valent linking group,
R is a hydrogen atom or a monovalent hydrocarbon group,
L is a hydrolyzable group or a hydroxy group,
n is an integer of from 0 to 2, and
k is an integer of from 1 to 10.

[10] The fluorinated ether compound according to [9], wherein in the formula (10), $A^{10}$ is a $C_{1-20}$ perfluoroalkyl group, and all the $(R^{f5}O)$ and $(R^{f6}O)$ are located on the $A^{10}$-O-side from the $[0.5\times(m1+m2+m3+m4+m5+m6)]$th unit as counted from the $A^{10}$-O— side.

[11] A fluorinated ether composition, comprising at least one type of the fluorinated ether compound as defined in any one of the above [1] to [10], and another fluorinated ether compound.

[12] A coating liquid comprising the fluorinated ether compound as defined in any one of the above [1] to [10] or the fluorinated ether composition as defined in [11], and a liquid medium.

[13] An article having a surface layer formed of the fluorinated ether compound as defined in any one of the above [1] to [10] or the fluorinated ether composition as defined in [11], on a surface of a substrate.

[14] A method for producing an article, which comprises treating a surface of a substrate by dry coating method using the fluorinated ether compound as defined in any one of the above [1] to [10] or the fluorinated ether composition as defined in [11] to form a surface layer on the surface of the substrate.

[15] A method for producing an article, which comprises applying the coating liquid as defined in [12] by wet coating method to a surface of a substrate, and removing the liquid medium, to form a surface layer on the surface of the substrate.

The present invention further provides a fluorinated ether compound represented by the following formula (12), a fluorinated ether compound represented by the following formula (13), a fluorinated ether compound represented by the following formula (14) and a fluorinated ether compound represented by the following compound (15), useful as an intermediate for producing the fluorinated ether compound.

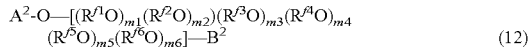

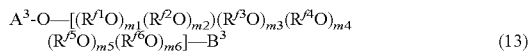

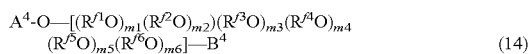

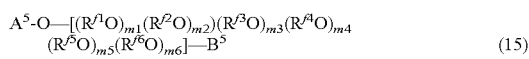

wherein $A^2$ is a $C_{1-20}$ perfluoroalkyl group or $B^2$, $B^2$ is $-R^{f7}-C(O)OR^8$, and $R^8$ is a hydrogen atom or a monovalent organic group, $A^3$ is a $C_{1-20}$ perfluoroalkyl group or $B^3$, and $B^3$ is $-R^{f7}-CH_2OH$, $A^4$ is a $C_{1-20}$ perfluoroalkyl group or $B^4$, and $B^4$ is $-R^{f7}-I$, and $A^5$ is a $C_{1-20}$ perfluoroalkyl group or $B^5$, $B^5$ is $-Q^a[-CH=CH_2]_k$ and $Q^a$ is a (k+1) valent linking group, in the formulae (12) to (15), $R^{f1}$ is a $C_1$ perfluoroalkylene group, $R^{f2}$ is a $C_2$ perfluoroalkylene group, $R^{f3}$ is a $C_3$ perfluoroalkylene group, $R^{f4}$ is a $C_4$ perfluoroalkylene group, $R^{f5}$ is a $C_5$ perfluoroalkylene group, $R^{f6}$ is a $C_6$ perfluoroalkylene group, and $R^{f7}$ is a $C_{1-6}$ perfluoroalkylene group, and m1, m2, m3, m4, m5 and m6 are each 0 or an integer of at least 1, m1+m2+m3+m4 is an integer of at least 1, m5+m6 is an integer of at least 1, and m1+m2+m3+m4+m5+m6 is an integer of from 2 to 200.

Further, $-Q^a[-CH=CH_2]_k$ as $B^5$ in the formula (5) is preferably a group represented by anyone of the following formulae (g11) to (g16). $R^{f7}$ in the following formula is the same group as $R^{f7}$ in the formulae (12) to (14).

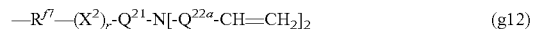

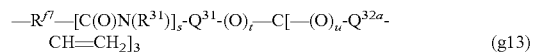

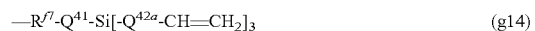

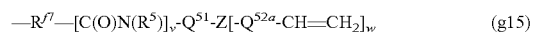

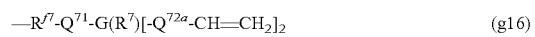

in the formula (g11),
$X^1$ is an etheric oxygen atom or $-C(O)N(R^1)-$ (provided that N is bonded to $Q^{1a}$),
$R^1$ is a hydrogen atom or an alkyl group,
p is 0 or 1, and
$Q^{1a}$ is an alkylene group, a group having an etheric oxygen atom or a silphenylene skeleton between carbon atoms of an alkylene group having at least 2 carbon atoms, or a group having a bivalent organopolysiloxane residue or a dialkylsilylene group between carbon atoms or at a terminal on the side bonded to $(X^1)_p$ of an alkylene group having at least 2 carbon atoms, in the formula (g12),
$X^2$ is an etheric oxygen atom, $-NH-$ or $-C(O)N(R^2)-$ (provided that N is bonded to $Q^{21}$),
$R^2$ is a hydrogen atom or an alkyl group,
r is 0 or 1 (provided that it is 0 when $Q^{21}$ is a single bond),
$Q^{21}$ is a single bond, an alkylene group, or a group having an etheric oxygen atom, $-NH-$, $-C(O)-$, $-C(O)O-$ or $-OC(O)-$ between carbon atoms of an alkylene group having at least 2 carbon atoms,
$Q^{22a}$ is an alkylene group, or a group having an etheric oxygen atom, $-NH-$ or a bivalent organopolysiloxane residue between carbon atoms of an alkylene group having at least 2 carbon atoms, and
two $[-Q^{22a}-CH=CH_2]$ may be the same or different, in the formula (g13),
$R^{31}$ is a hydrogen atom or an alkyl group,
s is 0 or 1,
$Q^{31}$ is a single bond, an alkylene group, or a group having an etheric oxygen atom between carbon atoms of an alkylene group having at least 2 carbon atoms,
t is 0 or 1 (provided that it is 0 when $Q^3$ is a single bond),
u is 0 or 1,
$Q^{32a}$ is an alkylene group, a group having an etheric oxygen atom or a silphenylene skeleton between carbon atoms of an alkylene group having at least 2 carbon atoms, or a group having $-C(O)N(R^{32})-$, a bivalent organopolysiloxane residue or a dialkylsilylene group between carbon atoms or at a terminal on the side bonded to $(O)_u$ of an alkylene group having at least 2 carbon atoms,
$R^{32}$ is a hydrogen atom or an alkyl group, and
three $[-(O)_u-Q^{32}-CH=CH_2]$ may be the same or different, in the formula (g14), $Q^{41}$ is an alkylene group, or a group having an etheric oxygen atom between carbon atoms of an alkylene group having at least 2 carbon atoms, $Q^{42a}$ is an alkylene group, or a group having an etheric oxygen atom or a bivalent organopolysiloxane residue between carbon atoms of an alkylene group having at least 2 carbon atoms, and three [-$Q^{42a}$-CH=CH$_2$] may be the same or different, in the formula (g15), $R^5$ is a hydrogen atom or an alkyl group, v is 0 or 1, $Q^{51}$ is an alkylene group, or a group having an etheric oxygen atom between carbon atoms of an alkylene group having at least 2 carbon atoms, Z is a (w+1) valent organopolysiloxane residue, $Q^{52a}$ is an alkylene group, or a group having an etheric oxygen atom or a bivalent organopolysiloxane residue between carbon atoms of an alkylene group having at least 2 carbon atoms, w is an integer of from 2 to 7, and w[-$Q^{52a}$-CH=CH$_2$] may be the same or different, in the formula (g16), $Q^{61}$ is a single bond, an alkylene group, or a group having an etheric oxygen atom between carbon atoms of an alkylene group having at least 2 carbon atoms, G is a carbon atom or a silicon atom, $R^6$ is a hydroxy group or an alkyl group, $Q^{62a}$ is an alkylene group, or a group having an etheric oxygen atom or a bivalent organopolysiloxane residue between carbon atoms of an alkylene group having at least 2 carbon atoms, and two [-$Q^{62a}$-CH=CH$_2$] may be the same or different.

Advantageous Effects of Invention

By the fluorinated ether compound of the present invention, it is possible to form a surface layer excellent in initial water/oil repellency, fingerprint stain removability, abrasion resistance and light resistance.

By the fluorinated ether composition of the present invention, it is possible to form a surface layer excellent in initial water/oil repellency, fingerprint stain removability, abrasion resistance and light resistance.

By the coating liquid of the present invention, it is possible to form a surface layer excellent in initial water/oil repellency, fingerprint stain removability, abrasion resistance and light resistance.

The article of the present invention has a surface layer excellent in initial water/oil repellency, fingerprint stain removability, abrasion resistance and light resistance.

According to the method for producing an article of the present invention, it is possible to produce an article having a surface layer excellent in initial water/oil repellency, fingerprint stain removability, abrasion resistance and light resistance.

DESCRIPTION OF EMBODIMENTS

In this specification, a compound represented by the formula (1) will be referred to as compound (1). Compounds represented by other formulae will be referred to in the same manner.

Further, a group represented by the formula (g1) will be referred to as group (g1). Groups represented by other formulae will be referred to in the same manner.

In this specification, meanings of the following terms and manner of description of chemical formulae are as follows.

A chemical formula of an oxyperfluoroalkylene unit shall be represented so that its oxygen atom be on the right-hand side of the perfluoroalkylene group.

A poly(oxyperfluoroalkylene) chain having units (α) and (β) (hereinafter sometimes referred to as "chain (αβ)") is a linear bivalent group, wherein one of the two terminals is a connecting bond bonded to a carbon atom (the carbon atom having this connecting bond will be referred to as a terminal carbon atom) and the other is a connecting bond of an oxygen atom (the oxygen atom having this connecting bond will be referred to as a terminal oxygen atom). A chemical formula of the chain (αβ) shall also be presented so that the terminal oxygen atom be on the right-hand side.

An "etheric oxygen atom" means an oxygen atom forming an ether bond (—O—) between carbon atoms.

A "hydrolyzable silyl group" means a group capable of forming a silanol group (Si—OH) by being hydrolyzed. For example, it may be $SiR_nL_{3-n}$ in the formula (1).

A "surface layer" means a layer formed on the surface of a substrate.

The "number average molecular weight" of the fluorinated ether compound is calculated by obtaining the number (average value) of oxyperfluoroalkylene groups based on the terminal group as a standard, by $^1$H-NMR and $^{19}$F-NMR. The terminal group may, for example, be a perfluoroalkyl group as $A^1$ or $SiR_nL_{3-n}$ as $B^1$ in the formula (1).

[Fluorinated Ether Compound]

The fluorinated ether compound of the present invention (hereinafter sometimes referred to as "the present compound") is a compound having a poly(oxyperfluoroalkylene) chain having a unit (α) which is an oxyperfluoroalkylene unit having 5 or 6 carbon atoms and a unit (β) which is an oxyperfluoroalkylene unit having at most 4 carbon atoms, that is, a chain (αβ), and having at least one of a hydrolyzable silyl group and a silanol group on at least one terminal of the chain (αβ) via a linking group (hereinafter a hydrolyzable silyl group and a silanol group will generally be referred to as a "hydrolyzable silyl group or the like").

The number of the chain (αβ) in the present compound may be one, or two or more. In order to obtain sufficient effects of the present invention, it is preferably one. In a case where the present compound has two or more chains (αβ), the present compound may be a compound having at least two chains (αβ) connected in series via a bivalent linking group, may be a compound having at least two chains (αβ) branched from a terminal of one chain (αβ) via a trivalent or higher linking group as a branch, or may be a compound having at least two chains (αβ) connected in series via a bivalent linking group, and having at least two chains (αβ) branched from a terminal of one chain (αβ) via a trivalent or higher linking group as a branch.

The number of the hydrolyzable silyl group in the present compound may be one, or may be two or more. In order to obtain sufficient effects of the present invention, it is preferably two or more.

In a case where the number of the chain (αβ) of the present compound is one, the present compound may have a hydrolyzable silyl group or the like on one terminal of the chain (αβ) via a linking group, or may have a hydrolyzable silyl group or the like on both terminals of the chain (αβ) via a linking group.

The present compound preferably has a hydrolyzable silyl group or the like only on one terminal of the chain (αβ), in order that the surface layer is more excellent in abrasion resistance.

In a case where the present compound has no hydrolyzable silyl group or the like on one terminal of the chain (αβ) via a linking group, it has a monovalent organic group on that terminal.

In a case where the number of the chain (αβ) of the present compound is one, the present compound is, in order that the surface layer is more excellent in initial water/oil repellency, abrasion resistance and fingerprint stain removability, a compound having a $C_{1-20}$ perfluoroalkyl group bonded to a carbon atom of one end of the chain (αβ) via an oxygen atom and having a hydrolyzable silyl group bonded to an oxygen atom of the other end of the chain (αβ) via a linking group.

(Chain (αβ))

The chain (αβ) preferably constitutes a molecular chain having units connected linearly or in branched between a terminal group and a linking group or between linking groups, in order to sufficiently obtain the effects of the present invention.

The chain (αβ) may have an oxyalkylene unit other than the units (α) and (β). As other unit, an oxypolyfluoroalkylene unit having at least one hydrogen atom may, for example, be mentioned. The chain (αβ) preferably consists solely of the unit (α) and the unit (β).

In the chain (αβ), as the unit (α), only one type of the unit (α) may be present, or two types of the units (α) differing in the number of carbon atoms may be present.

In the chain (αβ), as the unit (β), only one type of the unit (β) may be present, or two or more types of the units (β) differing in the number of carbon atoms may be present.

In the unit (α), the perfluoroalkylene group may be linear or branched. The unit (α) is, in view of more excellent initial water/oil repellency, abrasion resistance and light resistance of the surface layer, preferably linear, that is, $(CF_2CF_2CF_2CF_2CF_2O)$ or $(CF_2CF_2CF_2CF_2CF_2CF_2O)$.

The unit (β) is, in view of more excellent fingerprint stain removability of the surface layer, preferably a linear oxyperfluoroalkylene unit, more preferably $(CF_2O)$ or $(CF_2CF_2O)$, and in view of more excellent lubricity of the surface layer, particularly preferably $(CF_2O)$.

By the chain (αβ) having the unit (α), the surface layer is excellent in initial water/oil repellency, abrasion resistance and light resistance. However, if it consists of only the unit (α), the crystallinity of the poly(oxyperfluoroalkylene) chain tends to be too high, whereby fingerprint stain removability will be insufficient. Accordingly, by containing the unit (β), the crystallinity of the poly(oxyperfluoroalkylene) chain is lowered, and the initial water/oil repellency, abrasion resistance, fingerprint stain removability and light resistance of the surface layer can be achieved in a well-balanced manner.

In the chain (αβ), the proportion of the unit (α) (that is, the number of the unit (α)/the number of the unit (α) and the number of the unit (β)) is preferably from 0.02 to 0.5, particularly preferably from 0.02 to 0.2. That is, in the formula (11) or the like described hereinafter, (m5+m6)/(m1+m2+m3+m4+m5+m6) is preferably from 0.02 to 0.5, particularly preferably from 0.02 to 0.2. Within such a range, initial water/oil repellency, abrasion resistance, fingerprint stain removability and light resistance on the surface layer can be achieved in a well-balanced manner.

Particularly in the formula (11) or the like, it is preferred that $A^1$ or the like is a $C_{1-20}$ perfluoroalkyl group, and the positions of all $(R'^5O)$ and $(R'^6O)$ are on the $A^1$-O— side from [0.5×(m1+m2+m3+m4+m5+m6)]th unit as counted from the $A^1$-O— side. That is, they are preferably between the first and [0.5×(m1+m2+m3+m4+m5+m6)]th units as counted from the $A^1$-O— side. However, in a case where m1+m2+m3+m4+m5+m6 is an odd number, it corresponds to a natural number not exceeding 0.5 times that number.

In the chain (αβ), the binding order of the unit (α) and the unit (β) is not limited, and the units may be arranged randomly, in blocks or alternately. In order to efficiently obtain the initial water/oil repellency, abrasion resistance, fingerprint stain removability and light resistance on the surface layer, the chain preferably contains a structure having the unit (α) and the unit (β) alternately arranged.

(Linking Group)

The linking group may be a known linking group connecting a poly(oxyperfluoroalkylene) chain and a hydrolyzable silyl group or the like in a known fluorinated ether compound used as a surface treatment agent. Of the known linking group, the structure may be changed within a range not to impair the effects of the present invention. The linking group may be property determined within a range of knowledge of those skilled in the art.

(Terminal Group)

The hydrolyzable silyl group or the like is preferably a hydrolyzable silyl group in view of excellent storage stability of the present compound.

The number of the hydrolyzable silyl group or the like bonded to the linking group is, in order to sufficiently obtain the effects of the present invention, preferably from 1 to 10, more preferably from 1 to 3, particularly preferably 2 or 3.

In a case where the present compound has no hydrolyzable silyl group or the like on one terminal of the chain (αβ) via the linking group, the monovalent organic group present on the terminal is preferably a perfluoroalkyl group or a perfluoroalkyl group having an etheric oxygen atom, particularly preferably a perfluoroalkyl group.

(Present Compound)

The present compound may be a single compound, or may be a mixture of two or more types differing in the chain (αβ), the terminal group, the linking group or the like.

The number average molecular weight of the present compound is preferably from 2,000 to 10,000. When the number average molecular weight is within such a range, the surface layer is more excellent in the abrasion resistance. The number average molecular weight of the present compound is preferably from 2,100 to 9,000, particularly preferably from 2,400 to 8,000.

The present compound, which has the chain (αβ), a high content of fluorine atoms. Further, as described above, it has the chain (αβ) having the unit (α) to impart high initial water/oil repellency, abrasion resistance and light resistance to the surface layer and the unit (β) to lower the crystallinity of the poly(oxyperfluoroalkylene) chain which is increased by the unit (α). Accordingly, the present compound is capable of forming a surface layer having high initial water/oil repellency and being excellent in abrasion resistance, fingerprint stain removability and light resistance.

By the surface treatment by the present compound, the fluorinated ether composition or the coating liquid, as described hereinafter, the hydrolyzable silyl group $(SiR_nL_{3-n})$ in the present compound undergoes hydrolysis to form a silanol group (Si—OH), such silanol groups are intermolecularly reacted to form a Si—O—Si bond, or such a silanol group undergoes dehydration condensation with a hydroxy group (substrate —OH) on the surface of the substrate to form a chemical bond (substrate —O—Si). That is, the surface layer in the present invention contains the present compound in such a state that some or all of hydrolyzable silyl groups in the present compound are hydrolyzed and subjected to dehydration condensation.

(Compound (1))

The present compound is, in order to sufficiently obtain the effects of the present invention, preferably compound (1).

$$A^1\text{-O}-(R^fO)_m-B^1 \quad (1)$$

wherein $A^1$ is a $C_{1-20}$ perfluoroalkyl group or $B^1$, $R^f$ is a $C_{1-6}$ perfluoroalkylene group, m is an integer of from 2 to 200, $(R^fO)_m$ has the unit ($\alpha$) and the unit ($\beta$), $B^1$ is -Q[-SiR$_n$L$_{3-n}$]$_k$, Q is a (k+1) valent linking group, R is a hydrogen atom or a monovalent hydrocarbon group, L is a hydrolyzable group or a hydroxy group, n is an integer of from 0 to 2, and k is an integer of from 1 to 10.

<Chain ($\alpha\beta$)>

In the chain ($\alpha\beta$), that is, $(R^fO)_m$, the bonding order of the unit ($\alpha$) and the unit ($\beta$) is not limited, and the units may be arranged randomly, in blocks or alternately. In order to efficiently achieve the initial water/oil repellency, abrasion resistance, fingerprint stain removability and light resistance of the surface layer, the chain preferably contains a structure having the unit ($\alpha$) and the unit ($\beta$) alternately arranged.

The chain ($\alpha\beta$) is, in view of more excellent initial water/oil repellency, abrasion resistance, fingerprint stain removability and light resistance of the surface layer, preferably one having at least one of ($CF_2CF_2CF_2CF_2CF_2O$) and ($CF_2CF_2CF_2CF_2CF_2CF_2O$) and at least one of ($CF_2O$) and ($CF_2CF_2O$).

The chain ($\alpha\beta$) is preferably one having the following structure in at least part of the chain ($\alpha\beta$). In the following structural formulae, a structural formula having x1 pieces of unit ($\alpha$) and x2 pieces of the unit ($\beta$) represents a structure having x1 pieces of the unit ($\alpha$) and x2 pieces of the unit ($\beta$) arranged randomly or in blocks, and a structure having x3 pieces of assembly having the unit ($\alpha$) and the unit ($\beta$) bonded represents a structure having the unit ($\alpha$) and the unit ($\beta$) alternately arranged. In a structure having the units alternately arranged, if the total number of the unit ($\alpha$) and the unit ($\beta$) is an odd number, the chain ($\alpha\beta$) has a structure having (X3-1) pieces of assembly and having one unit ($\beta$) on the terminal on the unit ($\alpha$) side, or a structure having (X3-1) pieces of assembly and one unit ($\alpha$) on the terminal on the unit ($\beta$) side.

$(CF_2CF_2CF_2CF_2CF_2O)_{x1}(CF_2O)_{x2}$ $(CF_2CF_2CF_2CF_2CF_2O)_{x1}(CF_2CF_2O)_{x2}$ $(CF_2CF_2CF_2CF_2CF_2CF_2O)_{x1}(CF_2O)_{x2}$ $(CF_2CF_2CF_2CF_2CF_2CF_2O)_{x1}(CF_2CF_2O)_{x2}$ $(CF_2CF_2CF_2CF_2CF_2O-CF_2O)_{x3}$ $(CF_2CF_2CF_2CF_2CF_2O-CF_2CF_2O)_{x3}$ $(CF_2CF_2CF_2CF_2CF_2CF_2O-CF_2O)_{x3}$ $(CF_2CF_2CF_2CF_2CF_2CF_2O-CF_2CF_2O)_{x3}$ $(CF_2O-CF_2CF_2CF_2CF_2CF_2O)_{x3}$ $(CF_2O-CF_2CF_2CF_2CF_2CF_2CF_2O)_{x3}$ $(CF_2CF_2O-CF_2CF_2CF_2CF_2CF_2O)_{x3}$ $(CF_2CF_2O-CF_2CF_2CF_2CF_2CF_2CF_2O)_{x3}$ wherein x1 and x2 are each an integer of at least 1, x1+x2 is an integer of from 2 to 200, and x3 is an integer of from 1 to 100.

The chain ($\alpha\beta$) is preferably one having the following structure, in view of easy production of the compound (1):

$(CF_2CF_2CF_2CF_2CF_2O-CF_2O)_{x3}$ $(CF_2CF_2CF_2CF_2CF_2CF_2O-CF_2O)_{x3}$ $(CF_2CF_2O-CF_2CF_2CF_2CF_2CF_2O)_{x3-1}CF_2CF_2O$ $(CF_2CF_2O-CF_2CF_2CF_2CF_2CF_2CF_2O)_{x3-1}CF_2CF_2O$

The chain ($\alpha\beta$) is also preferably one having the following structure having a combination two or more of arrangements of the unit ($\alpha$) and the unit ($\beta$) randomly, in blocks or alternately. In the following formulae, x21, x22, x31 and x4 are each an integer of at least 1.

$(CF_2O-CF_2CF_2CF_2CF_2CF_2O)_{x31}-(CF_2CF_2O-CF_2CF_2CF_2CF_2O)_{x4}-CF_2CF_2O$; wherein x31+x4 is an integer of from 2 to 99.

$(CF_2CF_2O-CF_2CF_2CF_2CF_2CF_2CF_2O)_{x31}-(CF_2CF_2O-CF_2CF_2CF_2CF_2O)_{x4}-CF_2CF_2O$; wherein x31+x4 is an integer of from 2 to 99.

$(CF_2CF_2O-CF_2CF_2CF_2CF_2CF_2CF_2O)_{x31}-(CF_2CF_2O-CF_2CF_2CF_2CF_2O)_{x4}-(CF_2O)_{x21}(CF_2CF_2O)_{x22}$; wherein x21+x22+x31×2+x4×2 is an integer of from 6 to 200.

$(CF_2CF_2O-CF_2CF_2CF_2CF_2CF_2CF_2O)_{x31}-(CF_2O)_{x21}-(CF_2CF_2O)_{x22}-(CF_2CF_2O-CF_2CF_2CF_2CF_2O)_{x4}-CF_2CF_2O$; wherein x21+X22+X31×2+x4×2 is an integer of from 7 to 199.

$CF_2O-CF_2CF_2CF_2CF_2CF_2O-CF_2CF_2O-(CF_2O)_{x21}(CF_2CF_2O)_{x22}$; wherein x21+x22 is an integer of from 2 to 197.

$CF_2O-CF_2CF_2CF_2CF_2CF_2O-(CF_2CF_2O-CF_2CF_2CF_2CF_2O)_{x4}-CF_2CF_2O$; wherein x4 is an integer of from 1 to 98.

In the compound (1), $(R^fO)_m$ may be represented also by $[(R^{f1}O)_{m1}(R^{f2}O)_{m2}(R^{f3}O)_{m3}(R^{f4}O)_{m4}(R^{f5}O)_{m5}(R^{f6}O)_{m6}]$. That is, the compound (1) may be represented by the following formula (11):

$$A^1-O-[(R^{f1}O)_{m1}(R^{f2}O)_{m2}(R^{f3}O)_{m3}(R^{f4}O)_{m4}(R^{f5}O)_{m5}(R^{f6}O)_{m6}]-B^1 \quad (11)$$

In the above formula, $R^{f1}$ is a $C_1$ perfluoroalkylene group, $R^{f2}$ is a $C_2$ perfluoroalkylene group, $R^{f3}$ is a $C_3$ perfluoroalkylene group, $R^{f4}$ is a $C_4$ perfluoroalkylene group, $R^{f5}$ is a $C^5$ perfluoroalkylene group, $R^{f6}$ is a $C_6$ perfluoroalkylene group, and m1, m2, m3, m4, m5 and m6 are each 0 or an integer of at least 1, provided that m1+m2+m3+m4 is an integer of at least 1, m5+m6 is an integer of at least 1, and m1+m2+m3+m4+m5+m6 is an integer of from 2 to 200.

In the above formula, each of the units represented by ($R^{f1}O$), ($R^{f2}O$), ($R^{f3}O$) and ($R^{f4}O$) is the unit ($\beta$), and each of the units represented by ($R^{f5}O$) and ($R^{f6}O$) is the unit ($\alpha$). In the above formula, m1 to m6 respectively represent the number of units ($R^{f1}O$) to ($R^{f6}O$), not the arrangement of the respective units ($R^{f1}O$) to ($R^{f6}O$). For example, $(R^{f5}O)_{m5}$ represents that the number of ($R^{f5}O$) is m5, not the block arrangement structure of $(R^{f5}O)_{m5}$. Likewise, the order of description of ($R^{f1}O$) to ($R^{f6}O$) does not represent the binding order of the respective units.

As mentioned above, $R^{f2}$ to $R^{f6}$ are each preferably a linear perfluoroalkylene group. That is, it is preferred that $R^{f2}$ is $(CF_2)_2$, $R^{f3}$ is $(CF_2)_3$, $R^{f4}$ is $(CF_2)_4$, $R^{f5}$ is $(CF_2)_5$ and $R^{f6}$ is $(CF_2)_6$.

m1+m2+m3+m4 is, in view of more excellent initial water/oil repellency on the surface layer, preferably an integer of at least 3, particularly preferably an integer of at least 5. m1+m2+m3+m4 is, in order that the number average molecular weight of the compound (1) is not too high, preferably an integer of at most 45, particularly preferably an integer of at most 30.

m3 and m4 are preferably 0, in view of more excellent fingerprint stain removability of the surface layer.

m5+m6 is, in view of more excellent initial water/oil repellency, abrasion resistance and light resistance of the surface layer, preferably an integer of at least 3, particularly preferably an integer of at least 5. m5+m6 is, in order that the number average molecular weight of the compound (1) is not too high, preferably an integer of at most 80, particularly preferably an integer of at most 60.

Further, as described above, (m5+m6)/(m1+m2+m3+m4+m5+m6) is preferably from 0.02 to 0.5, particularly preferably from 0.02 to 0.2.

<$A^1$ Group>

$A^1$ is a $C_{1-20}$ perfluoroalkyl group or $B^1$. The perfluoroalkyl group may be linear or branched. In view of more excellent lubricity and abrasion resistance on the surface layer, it is preferably a $C_{1-10}$ perfluoroalkyl group, more preferably a $C_{1-6}$ perfluoroalkyl group, particularly preferably a $C_{1-3}$ perfluoroalkyl group.

$A^1$ may, for example, be $CF_3$—, $CF_3CF_2$—, $CF_3CF_2CF_2$—, $CF_3CF_2CF_2CF_2$—, $CF_3CF_2CF_2CF_2CF_2$—, $CF_3CF_2CF_2CF_2CF_2CF_2$— or $CF_3CF(CF_3)$—.

$A^1$ is, in view of more excellent initial water/oil repellency, abrasion resistance, fingerprint stain removability on the surface layer, preferably $CF_3$—, $CF_3CF_2$— or $CF_3CF_2CF_2$—.

<$B^1$ Group>

The compound (1) has $B^1$ on one end or on both ends of the chain (αβ), that is, $(R^fO)_m$. In a case where the compound (1) has two $B^1$ in one molecule, the two $B^1$ may be the same or different. As mentioned above, according to the description of the chemical formula in the present invention, when $B^1$ is described on the left-side of the chemical formula, $B^1$ is bonded to the terminal carbon atom of the chain (αβ) via an oxygen atom, that is, B—O— is bonded to the left-side of the chain (αβ).

$B^1$ is a group represented by -Q[-$SiR_nL_{3-n}]_k$, and the compound (1) has a hydrolyzable silyl group or the like represented by $SiR_nL_{3-n}$ at the terminal.

Q may be the same linking group in a known fluorinated ether compound used as a surface treatment agent, and is preferably a group having $SiR_nL_{3-n}$ removed from any one of the after-described groups (g1) to (g7).

The hydrolyzable group as L is a group which becomes a hydroxy group by hydrolysis reaction. That is, the hydrolyzable silyl group at the terminal of the compound (1) becomes a silanol group (Si—OH) by hydrolysis reaction. Silanol groups will further be intermolecularly reacted to form Si—O—Si bonds. Further, a silanol group will undergo dehydration condensation reaction with a hydroxy group (substrate-OH) on the surface of a substrate, to form a chemical bond (substrate-O—Si). The compound (1), which has a hydrolyzable silyl group or the like at the terminal, has favorable adhesion to a substrate, has favorable abrasion resistance and is capable of imparting water/oil repellency to the surface of a substrate.

L may, for example, be an alkoxy group, a halogen atom, an acyl group or an isocyanate group (—NCO). The alkoxy group is preferably a $C_{1-4}$ alkoxy group. The halogen atom is preferably a chlorine atom.

L is, in view of easy industrial production, preferably a $C_{1-4}$ alkoxy group or a halogen atom. L is, since outgassing during application will be less, and storage stability of the compound (1) will be excellent, preferably a $C_{1-4}$ alkoxy group, and in a case where storage stability of the compound (1) for a long time is required, particularly preferably an ethoxy group, and in a case where the reaction time after coating should be short, particularly preferably a methoxy group.

The monovalent hydrocarbon group as R may, for example, be an alkyl group, a cycloalkyl group, an alkenyl group or an allyl group.

R is preferably a monovalent hydrocarbon group, particularly preferably a monovalent saturated hydrocarbon group. The number of carbon atoms in the monovalent saturated hydrocarbon group is preferably from 1 to 6, more preferably from 1 to 3, particularly preferably from 1 to 2.

R is, in view of easy preparation, preferably a $C_{1-6}$ alkyl group, more preferably a $C_{1-3}$ alkyl group, particularly preferably a $C_{1-2}$ alkyl group.

n is preferably 0 or 1, particularly preferably 0. By the presence of a plurality of L in the molecule, bonding to the surface of the substrate will be more firm.

When n is at most 1, the plurality of L present in one molecule may be the same or different. In view of availability of raw materials and production efficiency, they are preferably the same.

The hydrolyzable silyl group ($SiR_nL_{3-n}$) is preferably —$Si(OCH_3)_3$, —$SiCH_3(OCH_3)_2$, —$Si(OCH_2CH_3)_3$, —$SiCl_3$, —$Si(OC(O)CH_3)_3$ or —$Si(NCO)_3$. In view of handling efficiency in industrial production, —$Si(OCH_3)_3$ is particularly preferred.

Further, $B^1$, that is, the group represented by -Q[-$SiR_nL_{3-n}]_k$, is preferably a group represented by any one of the formulae (g1) to (g7).

  (g1)

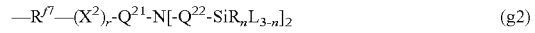  (g2)

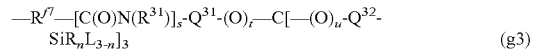  (g3)

  (g4)

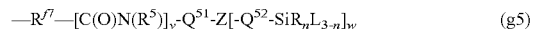  (g5)

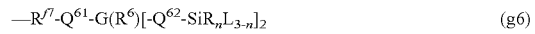  (g6)

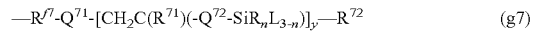  (g7)

wherein $R^{f7}$ is a $C_{1-6}$ perfluoroalkylene group,

R is a hydrogen atom or a monovalent hydrocarbon group,

L is a hydrolyzable group or a hydroxy group, and n is an integer of from 0 to 2.

In the formula (g1), $X^1$ is an etheric oxygen atom or —C(O)N($R^1$)— (provided that N is bonded to $Q^1$), $R^1$ is a hydrogen atom or an alkyl group, p is 0 or 1, and $Q^1$ is an alkylene group, a group having an etheric oxygen atom or a silphenylene skeleton between carbon atoms of an alkylene group having at least 2 carbon atoms, or a group having a bivalent organopolysiloxane residue or a diakylsilylene group between carbon atoms or at a terminal on the side bonded to $(X^1)_p$ of an alkylene group having at least 2 carbon atoms.

In the formula (g2), $X^2$ is an etheric oxygen atom, —NH— or —C(O)N($R^2$)— (provided that N is bonded to $Q^{21}$), $R^2$ is a hydrogen atom or an alkyl group, r is 0 or 1 (provided that it is 0 when $Q^{21}$ is a single bond), $Q^{21}$ is a single bond, an alkylene group, or a group having an etheric oxygen atom, —NH—, —C(O)—, —C(O)O— or —OC(O)— between carbon atoms of an alkylene group having at least 2 carbon atoms, $Q^{22}$ is an alkylene group, or a group having an etheric oxygen atom. —NH— or a bivalent organopolysiloxane residue between carbon atoms of an alkylene group having at least 2 carbon atoms, and two [-$Q^{22}$-Si$R_n L_{3-n}$] may be the same or different.

In the formula (g3), $R^{31}$ is a hydrogen atom or an alkyl group, s is 0 or 1, $Q^{31}$ is a single bond, an alkylene group, or a group having an etheric oxygen atom between carbon atoms of an alkylene group having at least 2 carbon atoms, t is 0 or 1 (provided that it is 0 when $Q^{31}$ is a single bond), u is 0 or 1, $Q^{32}$ is an alkylene group, a group having an etheric oxygen atom or a silphenylene skeleton between carbon atoms of an alkylene group having at least 2 carbon atoms, or a group having —C(O)N($R^{32}$)—, a bivalent organopolysiloxane residue or a diakylsilylene group between carbon atoms or at a terminal on the side bonded to (O)$_u$ of an alkylene group having at least 2 carbon atoms, $R^{32}$ is a hydrogen atom or an alkyl group, and three [—(O)$_u$-$Q^{32}$-Si$R_n L_{3-n}$] may be the same or different.

In the formula (g4), $Q^{41}$ is an alkylene group, or a group having an etheric oxygen atom between carbon atoms of an alkylene group having at least 2 carbon atoms, $Q^{42}$ is an alkylene group, or a group having an etheric oxygen atom or a bivalent organopolysiloxane residue between carbon atoms of an alkylene group having at least 2 carbon atoms, and three [-$Q^{42}$-Si$R_n L_{3-n}$] may be the same or different.

In the formula (g5), $R^5$ is a hydrogen atom or an alkyl group, v is 0 or 1, $Q^{51}$ is an alkylene group, or a group having an etheric oxygen atom between carbon atoms of an alkylene group having at least 2 carbon atoms, Z is a (w+1) valent organopolysiloxane residue, $Q^{52}$ is an alkylene group, or a group having an etheric oxygen atom or a bivalent organopolysiloxane residue between carbon atoms of an alkylene group having at least 2 carbon atoms, w is an integer of from 2 to 7, and w[-$Q^{52}$-Si$R_n L_{3-n}$] may be the same or different.

In the formula (g6), $Q^{61}$ is a single bond, an alkylene group, or a group having an etheric oxygen atom between carbon atoms of an alkylene group having at least 2 carbon atoms, G is a carbon atom or a silicon atom, $R^6$ is a hydroxy group or an alkyl group, $Q^{62}$ is an alkylene group, or a group having an etheric oxygen atom or a bivalent organopolysiloxane residue between carbon atoms of an alkylene group having at least 2 carbon atoms, and two [-$Q^{62}$-Si$R_n L_{3-n}$] may be the same or different.

In the formula (g7), $Q^{71}$ is a single bond, an alkylene group, or a group having an etheric oxygen atom between carbon atoms of an alkylene group having at least 2 carbon atoms, $R^{71}$ is a hydrogen atom or an alkyl group, $Q^{72}$ is a single bond or an alkylene group, $R^{72}$ is a hydrogen atom or a halogen atom, y is an integer of from 1 to 10, and two to ten [-$Q^{72}$-Si$R_n L_{3-n}$] may be the same or different.

$B^1$ is, so as to more sufficiently achieve the effects of the present invention, particularly preferably the group (g2), the group (g3), the group (g4), the group (g5) or the group (g6).

Hereinafter, with respect to the compound (1) represented by the formula (11), a compound (1) wherein $B^1$ is the group (g1) will be referred as compound (11a), a compound (1) wherein $B^1$ is the group (g2) as compound (11b), a compound (1) wherein $B^1$ is the group (g3) as compound (11c), a compound (1) wherein $B^1$ is the group (g4) as compound (11d), a compound (1) wherein $B^1$ is the group (g5) as compound (11e), a compound (1) wherein $B^1$ is the group (g6) as compound (11f), and a compound (1) wherein $B^1$ is the group (g7) as compound (11g).

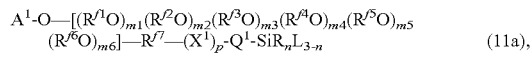 (11a),

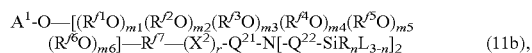 (11b),

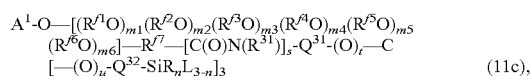 (11c),

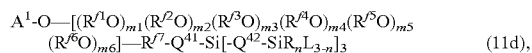 (11d),

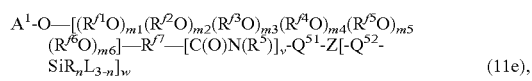 (11e),

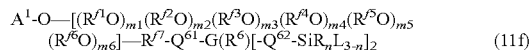 (11f)

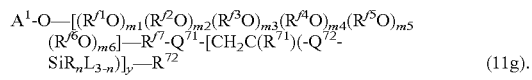 (11g).

$R^{f7}$ may be linear or branched. $R^{f7}$ is, in order that the compound (1) is easily produced, preferably —CF$_2$CF$_2$CF$_2$CF$_2$— or —CF$_2$CF$_2$CF$_2$CF$_2$CF$_2$.

Preferred embodiments of R, L, n and Si$R_n L_{3-n}$ are the same as the preferred embodiments of Si$R_n L_{3-n}$ in the compound (1).

As the bivalent organopolysiloxane residue in each of the groups (g1) to (g6), the following groups may be mentioned. In the following formulae, $R^a$ is a hydrogen atom, an alkyl group, an alkoxy group or a phenyl group. The number of carbon atoms in the alkyl group or the alkoxy group in $R^a$ is preferably from 1 to 10, particularly preferably 1.

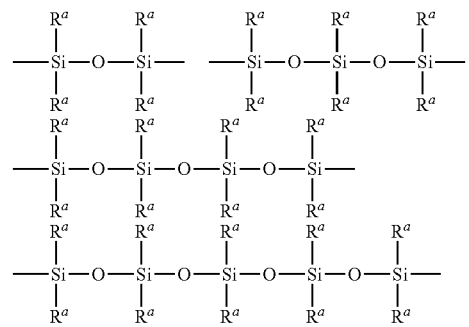

The silphenylene skeleton in the group (g1) or the group (g3) is a group represented by —Si($R^b$)$_2$PhSi($R^b$)$_2$— (wherein Ph is a phenylene group, and $R^b$ is a monovalent organic group). $R^b$ is preferably a C$_{1-10}$ alkyl group, particularly preferably a methyl group.

The dialkylsilylene group in the group (g1) or the group (g3) is a group represented by —Si(R$^c$)$_2$— (wherein R$^c$ is an alkyl group). R$^c$ is preferably a C$_{1-10}$ alkyl group, particularly preferably a methyl group.

<Compound (11a)>

R$^1$ is preferably a hydrogen atom or a C$_{1-4}$ alkyl group, and in view of easy production of the compound (11a), preferably a hydrogen atom.

Q$^1$ is preferably a C$_{1-10}$ alkylene group, a group having an etheric oxygen atom or a silphenylene skeleton between carbon atoms of a C$_{2-10}$ alkylene group, or a group having a bivalent organopolysiloxane residue or a dialkylsilylene group between carbon atoms or at a terminal on the side bonded to (X$^1$)$_p$ of a C$_{2-10}$ alkylene group. Q$^1$ is, in view of easy production of the compound (11a), in a case where (X$^1$)$_p$ is a single bond, preferably —CH$_2$OCH$_2$CH$_2$CH$_2$—, —CH$_2$OCH$_2$CH$_2$OCH$_2$CH$_2$CH$_2$—, —CH$_2$CH$_2$—, —CH$_2$CH$_2$CH$_2$— or —CH$_2$OCH$_2$CH$_2$CH$_2$Si(CH$_3$)$_2$OSi (CH$_3$)$_2$CH$_2$CH$_2$—, in a case where (X$^1$)$_p$ is —O—, preferably —CH$_2$CH$_2$CH$_2$— or —CH$_2$CH$_2$OCH$_2$CH$_2$CH$_2$—, and in a case where (X$^1$)$_p$ is —C(O)N(R$^1$)—, preferably a C$_{2-6}$ alkylene group (provided that the right side is bonded to Si).

As specific examples of the compound (11a), the following compounds may be mentioned. Here, in a case where a perfluoropolyether chain, that is, the chain ($\alpha\beta$) has B$^1$ on one end, PFPE is A$^1$-O—[(R$^{f1}$O)$_{m1}$(R$^{f2}$O)$_{m2}$(R$^{f3}$O)$_{m3}$ (R$^{f4}$O)$_{m4}$(R$^{f5}$O)$_{m5}$(R$^{f6}$O)$_{m6}$]—R$^{f7}$— and in a case where the chain ($\alpha\beta$) has B$^1$ on both ends, PFPE is —R$^{f7}$—O— [(R$^{f1}$O)$_{m1}$(R$^{f2}$O)$_{m2}$(R$^{f3}$O)$_{m3}$(R$^{f4}$O)$_{m4}$(R$^{f5}$O)$_{m5}$(R$^{f6}$O)$_{m6}$]— R$^{f7}$—. A preferred embodiment of PFPE is a combination of the above preferred A$^1$, chain ($\alpha\beta$) and R$^{f7}$.

atoms of a C$_{2-10}$ alkylene group, and in view of easy production of the compound (11b), particularly preferably —CH$_2$CH$_2$CH$_2$— or —CH$_2$CH$_2$OCH$_2$CH$_2$CH$_2$— (provided that the right side is bonded to Si).

As specific examples of the compound (11b), the following compounds may be mentioned. PFPE is the same as the PFPE in the compound (11a), and the preferred embodiment is also the same.

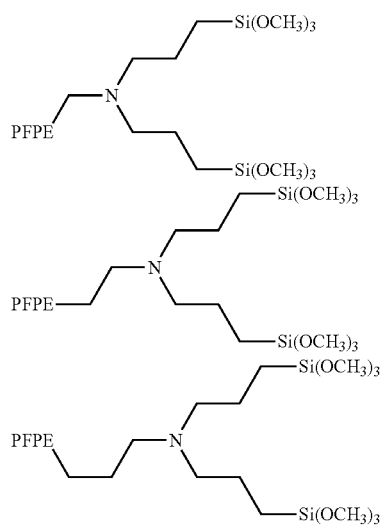

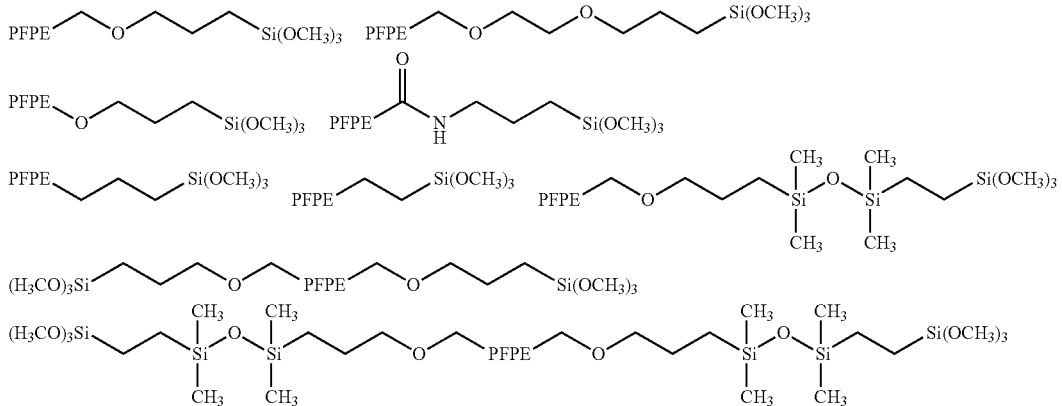

<Compound (11b)>

(X$^2$)$_r$ is, in view of easy production of compound (11b), preferably a single bond.

R$^2$ is preferably a hydrogen atom or a C$_{1-4}$ alkyl group, and in view of easy production of compound (11b), preferably a hydrogen atom.

Q$^{21}$ is, in a case where (X$^2$)$_r$ is a single bond, preferably a C$_{1-10}$ alkylene group or a group having an etheric oxygen atom or —NH— between carbon atoms of a C$_{2-10}$ alkylene group, and in view of easy production of the compound (11b), particularly preferably —CH$_2$—, —CH$_2$CH$_2$—, —CH$_2$CH$_2$CH$_2$—, —CH$_2$OCH$_2$CH$_2$— or —CH$_2$NHCH$_2$CH$_2$— (provided that the right side is bonded to N).

Q$^{22}$ is preferably a C$_{1-10}$ alkylene group, or a group having an etheric oxygen atom or —NH— between carbon -continued

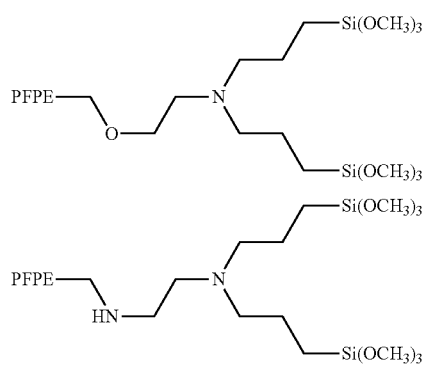

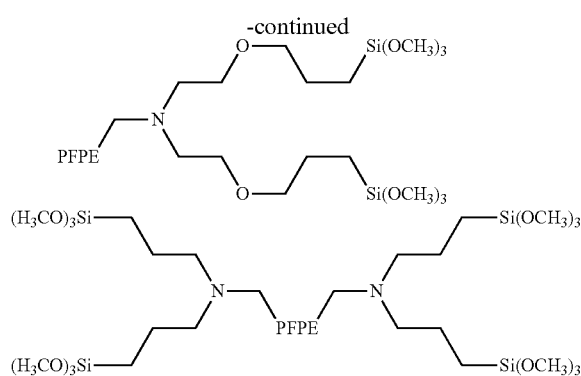

<Compound (11c)>

$R^{31}$ is, in view of easy production of the compound (11c), preferably a hydrogen atom. The alkyl group as $R^{31}$ is preferably a $C_{1-4}$ alkyl group.

$Q^{31}$ is preferably a $C_{1-10}$ alkylene group or a group having an etheric oxygen atom between carbon atoms of a $C_{2-10}$ alkylene group. $-Q^{31}-(O)_t-$ is, in view of easy production of the compound (11c), in a case where s is 0, preferably a single bond, $-CH_2O-$, $-CH_2OCH_2-$, $-CH_2OCH_2CH_2O-$ or $-CH_2OCH_2CH_2OCH_2-$ (provided that the left side is bonded to $R^{r7}$), and in a case where s is 1, preferably a single bond or $-CH_2-$, $-CH_2CH_2-$.

$R^{32}$ is preferably a hydrogen atom or a $C_{1-4}$ alkyl group, and in view of easy production of the compound (11c), preferably a hydrogen atom.

$Q^{32}$ is preferably a $C_{1-10}$ alkylene group, a group having an etheric oxygen atom or a silphenylene skeleton between carbon atoms of a $C_{2-10}$ alkylene group, or a group having $-C(O)N(R^{32})-$, a bivalent organopolysiloxane residue or a dialkylsilylene group between carbon atoms or at a terminal on the side bonded to $(O)_u$ of a $C_{2-10}$ alkylene group. $-(O)_u-Q^{32}-$ is, in view of easy production of the compound (11c), preferably $-CH_2CH_2-$, $-CH_2CH_2CH_2-$, $-CH_2OCH_2CH_2CH_2-$, $-CH_2OCH_2CH_2CH_2CH_2CH_2-$, $-OCH_2CH_2CH_2-$, $-OSi(CH_3)_2CH_2CH_2CH_2-$, $-OSi(CH_3)_2OSi(CH_3)_2CH_2CH_2CH_2-$ or $-CH_2CH_2CH_2Si(CH_3)_2PhSi(CH_3)_2CH_2CH_2-$ (provided that the right side is bonded to Si).

As specific examples of the compound (11c), the following compounds may be mentioned. PFPE is the same as PFPE in the compound (11a), and the preferred embodiment is also the same.

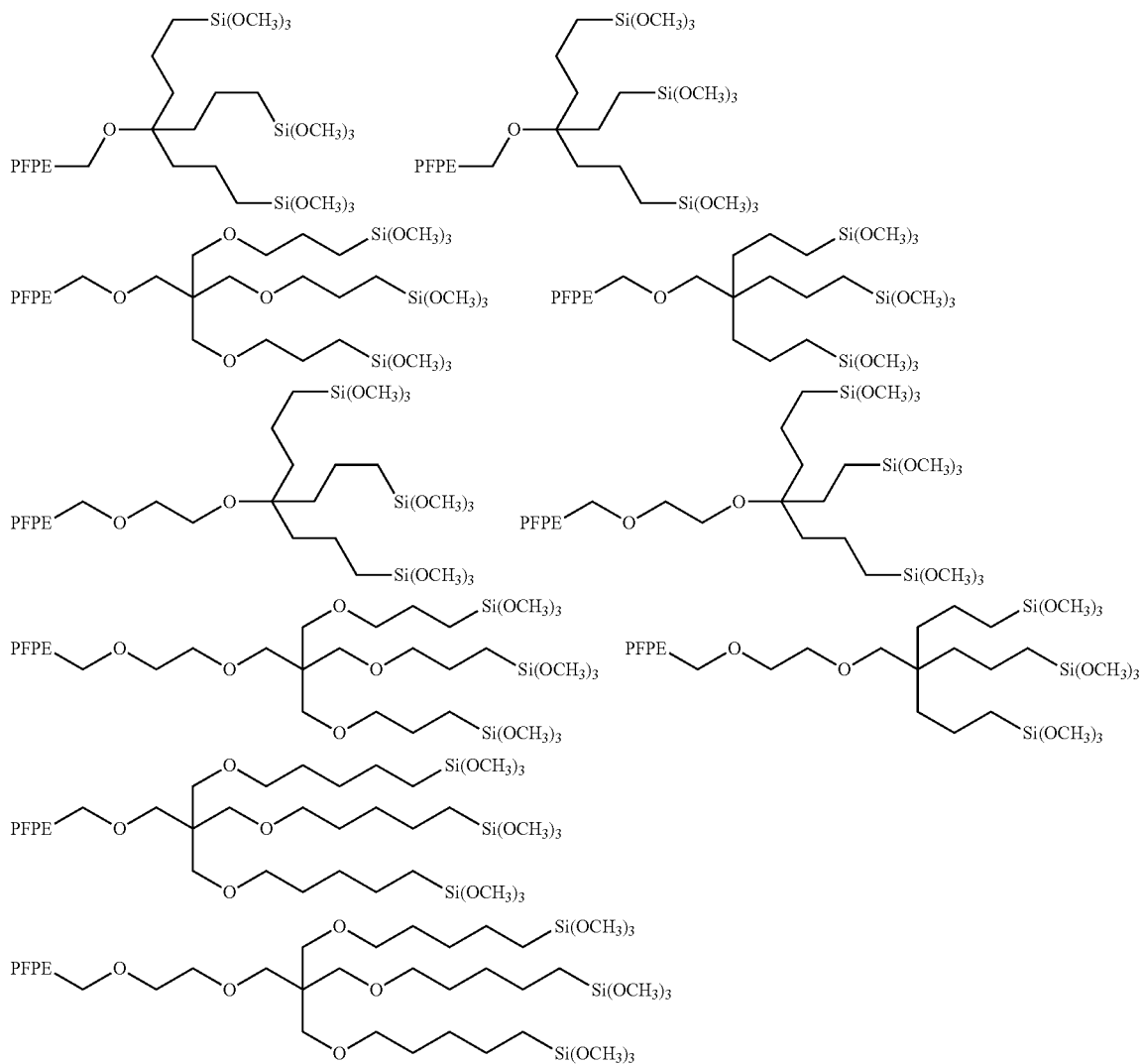

21
-continued
22
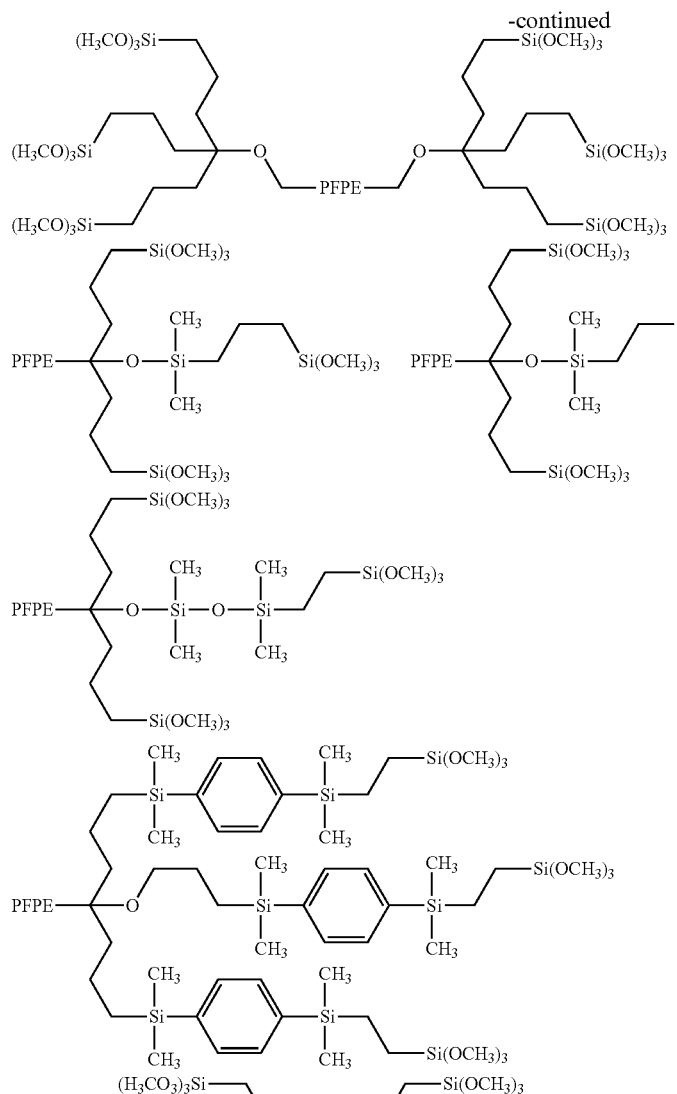

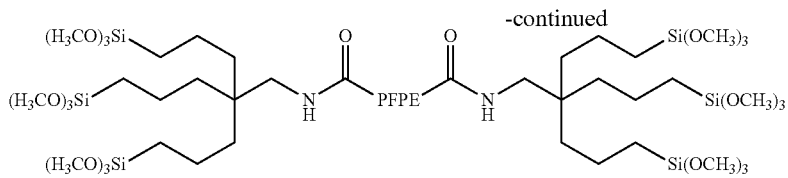

<Compound (11d)>

$Q^{41}$ is preferably a $C_{1-10}$ alkylene group, or a group having an etheric oxygen atom between carbon atoms of a $C_{2-10}$ alkylene group, and in view of easy production of the compound (11d), preferably —CH$_2$OCH$_2$CH$_2$CH$_2$—, —CH$_2$OCH$_2$CH$_2$OCH$_2$CH$_2$CH$_2$—, —CH$_2$CH$_2$— or —CH$_2$CH$_2$CH$_2$— (provided that the right side is bonded to Si).

$Q^{42}$ is preferably a $C_{1-10}$ alkylene group or a group having an etheric oxygen atom or a bivalent organopolysiloxane residue between carbon atoms of a $C_{2-10}$ alkylene group, and in view of easy production of the compound (11d), preferably —CH$_2$CH$_2$CH$_2$— or —CH$_2$CH$_2$OCH$_2$CH$_2$CH$_2$— (provided that the right side is bonded to SiR$_n$L$_{3-n}$).

As specific examples of the compound (11d), the following compounds may be mentioned. PFPE is the same as PFPE in the compound (11a), and the preferred embodiment is also the same.

<Compound (11e)>

$R^5$ is preferably a hydrogen atom or a $C_{1-4}$ alkyl group, and in view of easy production of the compound (11e), preferably a hydrogen atom.

$Q^{51}$ is preferably a $C_{1-10}$ alkylene group, or a group having an etheric oxygen atom between carbon atoms of a $C_{2-10}$ alkylene group, and in view of easy production of the compound (11e), preferably —CH$_2$OCH$_2$CH$_2$CH$_2$—, —CH$_2$OCH$_2$CH$_2$OCH$_2$CH$_2$CH$_2$—, —CH$_2$CH$_2$— or —CH$_2$CH$_2$CH$_2$— (provided that the right side is bonded to Z).

$Q^{52}$ is preferably a $C_{1-10}$ alkylene group or a group having an etheric oxygen atom or a bivalent organopolysiloxane residue between carbon atoms of a $C_{2-10}$ alkylene group, and in view of easy production of the compound (11e), preferably —CH$_2$CH$_2$— or —CH$_2$CH$_2$CH$_2$—.

As the (w+1) valent organopolysiloxane residue as Z, the following groups may be mentioned. In the following for-

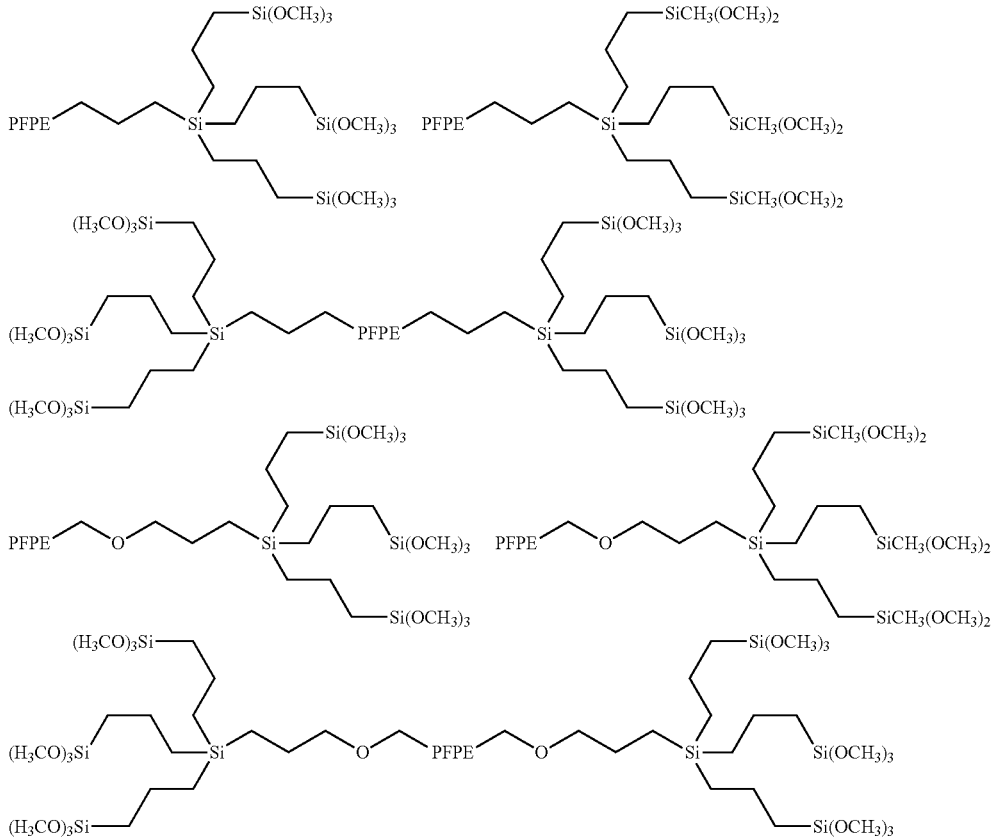

mulae, $R^a$ is a hydrogen atom, an alkyl group, an alkoxy group or a phenyl group. The number of carbon atoms of the alkyl group or the alkoxy group as $R^a$ is preferably from 1 to 10, particularly preferably 1.

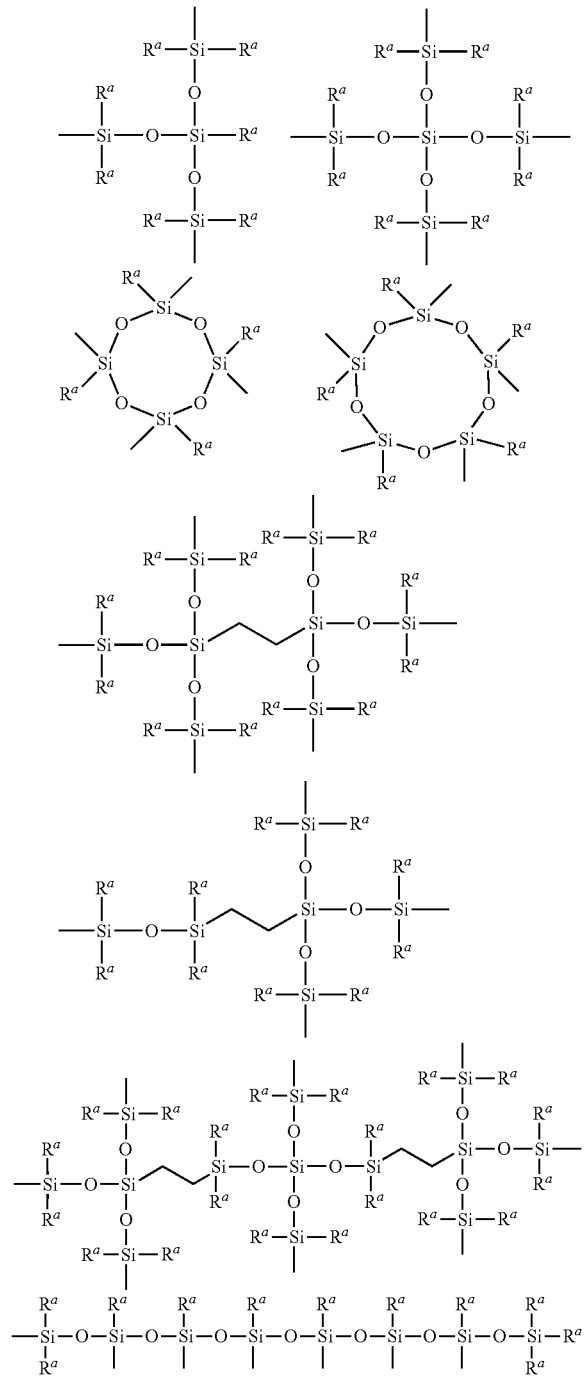

<Compound (11f)>

$Q^{61}$ preferably a single bond, a $C_{1-10}$ alkylene group, or a group having an etheric oxygen atom between carbon atoms of a $C_{2-10}$ alkylene group, and in view of easy production of the compound (11f), particularly preferably a single bond.

$G(R^6)$ is, in view of easy production of the compound (11f), preferably C(OH) or $Si(R^{6a})$(wherein $R^{6a}$ is an alkyl group, the number of carbon atoms of which is preferably from 1 to 10, particularly preferably 1).

$Q^{82}$ is preferably a $C_{1-10}$ alkylene group, or a group having an etheric oxygen atom between carbon atoms of a $C_{2-10}$ alkylene group, and in view of easy production of the compound (11f), preferably —$CH_2CH_2$—, —$CH_2CH_2CH_2$— or —$CH_2CH_2CH_2CH_2CH_2CH_2CH_2CH_2$—.

As specific examples of the compound (11f), the following compounds may be mentioned. PFPE is the same as the PFPE in the compound (11a), and the preferred embodiment is also the same.

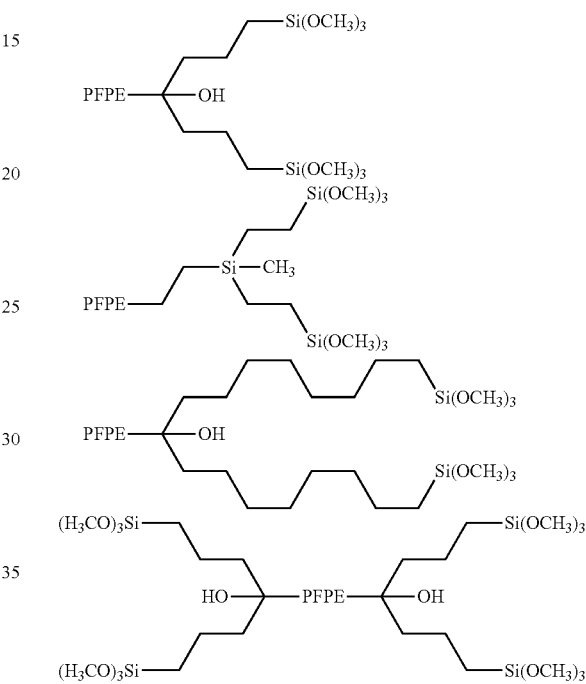

<Compound (11g)>

$Q^{71}$ is preferably a single bond, a $C_{1-10}$ alkylene group or a group having an etheric oxygen atom between carbon atoms of a $C_{2-10}$ alkylene group, and in view of easy production of the compound (11g), preferably a single bond.

$R^1$ is preferably a hydrogen atom or a $C_{1-10}$ alkyl group, and in view of easy production of the compound (11g), preferably a hydrogen atom. The alkyl group as $R^{71}$ is preferably a methyl group.

$Q^{72}$ is a single bond or a $C_{1-10}$ alkylene group, and in view of easy production of the compound (11g), preferably a single bond or —$CH_2$—.

$R^{72}$ is, in view of easy production of the compound (11g), preferably a hydrogen atom.

As specific examples of the compound (11g), the following compounds may be mentioned. PFPE is the same as the PFPE in the compound (11a), and the preferred embodiment is also the same.

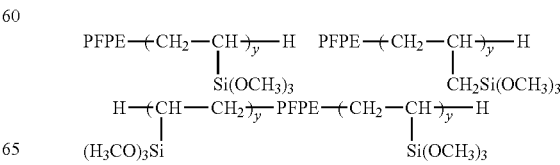

(Compound (10))

The present compound other than the compound (1) is, in order to achieve the effects of the present invention, preferably compound (10) represented by the following formula (10). The compound (10) is a compound having at least 2 chains (αβ), whereas the compound (1) represented by the formula (1) or the formula (11) is a compound having one chain (αβ).

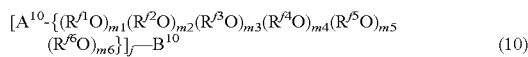

wherein $A^{10}$ is a $C_{1-20}$ perfluoroalkyl group or $B^{10}$, $R^{f1}$ to $R^{f6}$ are the same as $R^{f1}$ to $R^{f6}$ in the above formula (11), m1 to m6 are the same as m1 to m6 in the formula (11), j is an integer of from 2 to 10, $B^{10}$ is $Q^{10}[-SiR_nL_{3-n}]_k$, $Q^{10}$ is a (k+j) valent linking group, R is a hydrogen atom or a monovalent hydrocarbon group, L is a hydrolyzable group or a hydroxy group, n is an integer of from 0 to 2, and k is an integer of from 1 to 10.

The preferred embodiment of the chain (αβ) is the same as the preferred embodiment of the chain (αβ) in the compound (1).

The preferred embodiment of the $C_{1-20}$ perfluoroalkyl group as $A^{10}$ is the same as the preferred embodiment of the $C_{1-20}$ perfluoroalkyl group as $A^1$ in the compound (1).

The compound (10) has from one to (1+j) $B^{10}$. In a case where the compound (10) has a plurality of $B^{10}$ in its molecule, they may be the same or different.

$B^{10}$ is a group represented by $Q^{10}[-SiR_nL_{3-n}]_k$, and the compound (10) has a hydrolyzable silyl group or the like represented by $SiR_nL_{3-n}$ at its terminal. The preferred embodiment of $SiR_nL_{3-n}$ is the same as the preferred embodiment of $SiR_nL_{3-n}$ in the compound (1).

$Q^{10}$ may be the same as the linking group in a known fluorinated ether compound used as a surface treatment agent. $Q^{10}$ may, for example, be specifically a group having a (k+j) valent cyclic structure having a carbon atom or a nitrogen atom to which j chains (αβ) are bonded directly or via a bivalent linking group, and having a carbon atom or a nitrogen atom to which k $SiR_nL_{3-n}$ is bonded directly or via a bivalent linking group. Such a bivalent linking group may be a single bond, —C(O)NH— or an alkylene group.

[Method for Producing Fluorinated Ether Compound]

The present compound may be produced in the same manner as the method for producing a known fluorinated ether compound used as a surface treatment agent, except that a raw material having a specific chain (αβ) or its precursor chain is used as a part of or the entire polyfluoropolyether chain.

(Method for Producing Compound (1))

In a case where the present compound is the compound (1), the compound (1) may be produced, for example, by the following method.

To a terminal of an ester-terminal fluorinated ether compound (the after-described compound (2)), a hydroxy group-terminal fluorinated ether compound (the after-described compound (3)) or an iodine-terminal fluorinated ether compound (the after-described compound (4)), a carbon-carbon unsaturated double bond is introduced by a known method to obtain an unsaturated double bond-terminal fluorinated ether compound (the after-described compound (5)), and subjecting the compound (5) and $HSiR_nL_{3-n}$ to hydrosilylation reaction to obtain the compound (1).

A method of polymerizing $CH_2=CH-SiR_nL_{3-n}$, $CH_2=CHCH_2-SiR_nL_{3-n}$ or the like using an iodine-terminal fluorinated ether compound (compound (4)) as an initiator to obtain the compound (1).

<Compound (2)>

The compound (2) is a compound represented by the following formula (2) and may be represented also by the following formula (12). The compound represented by the following formula (12) will hereinafter be referred to as "compound (12)".

$$A^2\text{-O}-(R^fO)_m-B^2 \quad (2)$$

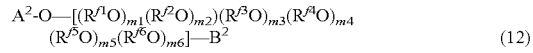

wherein $A^2$ is a $C_{1-20}$ perfluoroalkyl group or $B^2$, $B^2$ is $-R^{f7}-C(O)OR^8$, and $R^8$ is a hydrogen atom or a monovalent organic group.

The $C_{1-20}$ perfluoroalkyl group as $A^2$ is the same as the $C_{1-20}$ perfluoroalkyl group as $A^1$ in the compound (1), and the preferred embodiment is also the same. $R^{f7}$ is the same as $R^{f7}$ in the preferred $B^1$ ($B^1$ represented by the formula (g1) to (g7)) in the compound (1), and the preferred embodiment is also the same.

$R^8$ is preferably an alkyl group. The number of carbon atoms of the alkyl group is preferably from 1 to 10, particularly preferably 1.

<Compound (3)>

The compound (3) is a compound represented by the following formula (3), and may be represented also by the following formula (13). The compound represented by the following formula (13) will be referred to as "compound (13)".

$$A^3\text{-O}-(R^fO)_m-B^3 \quad (3)$$

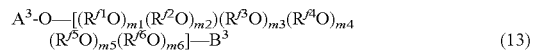

wherein $A^3$ is a $C_{1-20}$ perfluoroalkyl group or $B^3$, and $B^3$ is $-R^{f7}-CH_2OH$.

The $C_{1-20}$ perfluoroalkyl group as $A^3$ is the same as the $C_{1-20}$ perfluoroalkyl group as $A^1$ in the compound (1), and the preferred embodiment is also the same. $R^{f7}$ is the same as $R^{f7}$ in the preferred $B^1$ ($B^1$ represented by the formula (g1) to (g7)) in the compound (1), and the preferred embodiment is also the same.

<Compound (4)>

The compound (4) is a compound represented by the following formula (4), and may be represented also by the following formula (14). The compound represented by the following formula (14) will be hereinafter referred to as "compound (14)".

$$A^4\text{-O}-(R^fO)_m-B^4 \quad (4)$$

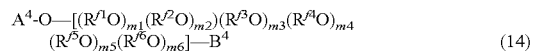

wherein $A^4$ is a $C_{1-20}$ perfluoroalkyl group or $B^4$, and $B^4$ is $-R^{f7}-I$.

The $C_{1-20}$ perfluoroalkyl group as $A^4$ is the same as the $C_{1-20}$ perfluoroalkyl group as $A^1$ in the compound (1), and the preferred embodiment is also the same. $R^{f7}$ is the same as $R^{f7}$ in the preferred $B^1$ ($B^1$ represented by the formula (g1) to (g7)) in the compound (1), and the preferred embodiment is also the same.

<Compound (5)>

The compound (5) is a compound represented by the following formula (5), and may be represented by the following formula (15). A compound represented by the following formula (15) will be hereinafter referred to as "compound 15".

$$A^5-O-(R^fO)_m-B^5 \quad (5)$$

$$A^5-O-[(R^{f1}O)_{m1}(R^{f2}O)_{m2})(R^{f3}O)_{m3}(R^{f4}O)_{m4}(R^{f5}O)_{m5}(R^{f6}O)_{m6}]-B^5 \quad (15)$$

wherein $A^5$ is a $C_{1\text{-}20}$ perfluoroalkyl group or $B^5$, and $B^5$ is $-Q^8[-CH=CH_2]_k$, and $Q^a$ is a (k+1) valent linking group.

The $C_{1\text{-}20}$ perfluoroalkyl group as $A^5$ is the same as the $C_{1\text{-}20}$ perfluoroalkyl group as $A^1$ in the compound (1), and the preferred embodiment is also the same. k is the same as k in the compound (1), and the preferred embodiment is also the same. $R^{f7}$ is the same as $R^{f7}$ in the preferred $B^1$ ($B^1$ represented by the formula (g1) to (g7)) in the compound (1), and the preferred embodiment is also the same.

In the compound (5), $B^5$ is preferably a group represented by any one of the following formulae (g11) to (g16) corresponding to the groups represented by the formulae (g1) to (g7) in the compound (1).

$$-R^{f7}-(X^1)_p-Q^{1a}-CH=CH_2 \quad (g11)$$

$$-R^{f7}-(X^2)_r-Q^{21}-N[-Q^{22a}-CH=CH_2]_2 \quad (g12)$$

$$-R^{f7}-[C(O)N(R^{31})]_s-Q^{31}-(O)_t-C[-(O)_u-Q^{32a}-CH=CH_2]_3 \quad (g13)$$

$$-R^{f7}-Q^{41}-Si[-Q^{42a}-CH=CH_2]_3 \quad (g14)$$

$$-R^{f7}-[C(O)N(R^5)]_v-Q^{51}-Z[-Q^{52a}-CH=CH_2]_w \quad (g15)$$

$$-R^{f7}-Q^{61}-G(R^6)[-Q^{62a}-CH=CH_2]_2 \quad (g16)$$

In the formula (g11), $X^1$ and p are the same as $X^1$ and p in the formula (g1), and the preferred embodiment is also the same. $Q^{1a}$ is an alkylene group (preferably a $C_{1\text{-}8}$ alkylene group), a group having an etheric oxygen atom or a silphenylene skeleton between carbon atoms of an alkylene group having at least 2 (preferably from 2 to 8) carbon atoms, or a group having a bivalent organopolysiloxane residue or a dialkylsilylene group between carbon atoms or at a terminal on the side bonded to ($X^1$), of an alkylene group having at least 2 carbon atoms. $Q^{1a}$-CH=CH$_2$ constitutes at least a part of $Q^1$ in the formula (g1) after the after-described hydrosilylation reaction.

In the formula (12), $X^2$, $R^2$, r and $Q^{21}$ are the same as $X^2$, $R^2$, r and $Q^{21}$ in the formula (g2), and the preferred embodiment is also the same. $Q^{22a}$ is an alkylene group (preferably a $C_{1\text{-}8}$ alkylene group), or a group having an etheric oxygen atom, —NH— or a bivalent organopolysiloxane residue between carbon atoms of an alkylene group having at least 2 (preferably from 2 to 8) carbon atoms. $Q^{22a}$-CH=CH$_2$ constitutes at least a part of $Q^{22}$ in the formula (g2) after the after-described hydrosilylation reaction. Two [-$Q^{22a}$-CH=CH$_2$] may be the same or different.

In the formula (g13), $R^{31}$, s, $Q^{31}$, t, u and $R^{32}$ are the same as $R^{31}$, s, $Q^{31}$, t, u and $R^{32}$ in the formula (g3), and the preferred embodiment is also the same. $Q^{32}a$ is an alkylene group (preferably a $C_{1\text{-}8}$ alkylene group), a group having an etheric oxygen atom or a silphenylene skeleton between carbon atoms of an alkylene group having at least 2 (preferably from 2 to 8) carbon atoms, or a group having —C(O)N($R^{32}$)—, a bivalent organopolysiloxane residue or a dialkylsilylene group between carbon atoms or at a terminal on the side bonded to (O)$_u$ of an alkylene group having at least 2 carbon atoms. $Q^{32a}$-CH=CH$_2$ constitutes at least a part of $Q^{32}$ in the formula (g3) after the after-described hydrosilylation reaction. Three [—(O)$_u$-$Q^{32a}$-CH=CH$_2$] may be the same or different.

In the formula (g14), $Q^{41}$ is the same as $Q^{41}$ in the formula (g4), and the preferred embodiment is also the same. $Q^{42a}$ is an alkylene group (preferably a $C_{1\text{-}8}$ alkylene group) or a group having an etheric oxygen atom or a bivalent organopolysiloxane residue between carbon atoms of an alkylene group having at least 2 (preferably from 2 to 8) carbon atoms. $Q^{42a}$-CH=CH$_2$ constitutes at least a part of $Q^{42}$ in the formula (g4) after the after-described hydrosilylation reaction. Three [-$Q^{42}$-CH=CH$_2$] may be the same or different.

In the formula (g15), $R^5$, v, $Q^{51}$, Z and w are the same as $R^5$, v, $Q^{51}$ and Z in the formula (g5), and the preferred embodiment is also the same. $Q^{52a}$ is an alkylene group (preferably a $C_{1\text{-}8}$ alkylene group) or a group having an etheric oxygen atom or a bivalent organopolysiloxane residue between carbon atoms of an alkylene group having at least 2 (preferably from 2 to 8) carbon atoms. $Q^{52a}$-CH=CH$_2$ constitutes at least a part of $Q^{52}$ in the formula (g5) after the after-described hydrosilylation reaction. w [-$Q^{52a}$-CH=CH$_2$] may be the same or different.

In the formula (g16), $Q^{61}$, G and $R^6$ are the same as $Q^{61}$, G and $R^6$ in the formula (g6), and the preferred embodiment is also the same. $Q^{62a}$ is an alkylene group (preferably a $C_{1\text{-}8}$ alkylene group) or a group having an etheric oxygen atom or a bivalent organopolysiloxane residue between carbon atoms of an alkylene group having at least 2 (preferably from 2 to 8) carbon atoms. $Q^{62a}$-CH=CH$_2$ constitutes at least a part of $Q^{62}$ in the formula (g6) after the after-described hydrosilylation reaction. Two [-$Q^{62a}$-CH=CH$_2$] may be the same or different.

Hereinafter, a compound (15) wherein $B^5$ is the group (g11) will be referred to as compound (15a), a compound (15) wherein $B^5$ is the group (g12) as compound (15b), a compound (15) wherein $B^5$ is the group (g13) as compound (15c), a compound (15) wherein $B^5$ is the group (g14) as compound (15d), a compound (15) wherein $B^5$ is the group (g15) as compound (15e), and a compound (15) wherein $B^5$ is the group (g16) as compound (15f).

$$A^5-O-[(R^{f1}O)_{m1}(R^{f2}O)_{m2})(R^{f3}O)_{m3}(R^{f4}O)_{m4}(R^{f5}O)_{m5}(R^{f6}O)_{m6}]-R^{f7}-(X^1)_p-Q^{1a}-CH=CH_2 \quad (15a),$$

$$A^5-O-[(R^{f1}O)_{m1}(R^{f2}O)_{m2})(R^{f3}O)_{m3}(R^{f4}O)_{m4}(R^{f5}O)_{m5}(R^{f6}O)_{m6}]-R^{f7}-(X^2)_r-Q^{21}-N[-Q^{22a}-CH=CH_2]_2 \quad (15b),$$

$$A^5-O-[(R^{f1}O)_{m1}(R^{f2}O)_{m2})(R^{f3}O)_{m3}(R^{f4}O)_{m4}(R^{f5}O)_{m5}(R^{f6}O)_{m6}]-R^{f7}-[C(O)N(R^{31})]_s-Q^{31}-(O)_t-C[-(O)_u-Q^{32a}-CH=CH_2]_3 \quad (15c),$$

$$A^5-O-[(R^{f1}O)_{m1}(R^{f2}O)_{m2})(R^{f3}O)_{m3}(R^{f4}O)_{m4}(R^{f5}O)_{m5}(R^{f6}O)_{m6}]-R^{f7}-Q^{41}-Si[-Q^{42a}-CH=CH_2]_3 \quad (15d),$$

$$A^5-O-[(R^{f1}O)_{m1}(R^{f2}O)_{m2})(R^{f3}O)_{m3}(R^{f4}O)_{m4}(R^{f5}O)_{m5}(R^{f6}O)_{m6}]-R^{f7}-[C(O)N(R^5)]_v-Q^{51}-Z[-Q^{52a}-CH=CH_2]_w \quad (15e),$$

$$A^5-O-[(R^{f1}O)_{m1}(R^{f2}O)_{m2})(R^{f3}O)_{m3}(R^{f4}O)_{m4}(R^{f5}O)_{m5}(R^{f6}O)_{m6}]-R^{f7}-Q^{61}-G(R^6)[-Q^{62a}-CH=CH_2]_2 \quad (15f).$$

(Specific Examples of Method for Producing Each Compound)

<Method (1) for Producing Compound (12)>

In accordance with the method disclosed in U.S. Pat. No. 4,740,579, in the presence of an acid, HOCH$_2$CF$_2$CF$_2$CH$_2$OH and HC(O)H are reacted to obtain compound (21-1) (1,3-dioxa-5,5,6,6,7,7-hexafluorocyclooctane).

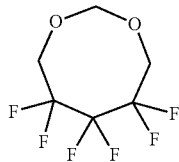 (21-1)

In accordance with the method disclosed in U.S. Pat. No. 4,740,579, in the presence of an acid and $HOCH_2CF_2CF_2CF_2CH_2OH$, the compound (21-1) is subjected to ring-opening polymerization to obtain compound (22-1).

$$HOCH_2CF_2CF_2CF_2CH_2O(CH_2OCH_2CF_2CF_2CF_2CH_2O)_{x3}H \quad (22\text{-}1)$$

The compound (22-1) and an acid halide (for example, $R^{f8}C(O)F$ (wherein $R^{f8}$ is a perfluoroalkyl group or a group having an etheric oxygen atom between carbon atoms of a perfluoroalkyl group having at least 2 carbon atoms) are reacted for esterification to obtain compound (23-1), which is further fluorinated to obtain compound (24-1).

$$R^{f8}C(O)OCH_2CF_2CF_2CF_2CH_2O(CH_2OCH_2CF_2CF_2CF_2CH_2O)_{x3}C(O)R^{f8} \quad (23\text{-}1)$$

$$R^{f8}C(O)OCF_2CF_2CF_2CF_2CF_2O(CF_2OCF_2CF_2CF_2CF_2CF_2O)_{x3}C(O)R^{f8} \quad (24\text{-}1)$$

Compound (24-2) may be obtained instead of the compound (24-1) by using $HOCH_2CF_2CF_2CF_2CF_2CH_2OH$ instead of $HOCH_2CF_2CF_2CF_2CH_2OH$ when the compounds (21-1) and (22-1) are obtained.

$$R^{f8}C(O)OCF_2CF_2CF_2CF_2CF_2CF_2O(CF_2OCF_2CF_2CF_2CF_2CF_2O)_{x3}C(O)R^{f8} \quad (24\text{-}2)$$

Further, compound (24-3) instead of the compound (24-1), or compound (24-4) instead of the compound (24-2), may be obtained by using a monool (for example, $CH_3OH$ or $CF_3CH_2OH$) when the compound (22-1) is obtained.

$$R^{f9}O(CF_2OCF_2CF_2CF_2CF_2CF_2O)_{x3}C(O)R^{f8} \quad (24\text{-}3)$$

$$R^{f9}O(CF_2OCF_2CF_2CF_2CF_2CF_2CF_2O)_{x3}C(O)R^{f8} \quad (24\text{-}4)$$

wherein $R^{f9}$ is a $C_{1\text{-}20}$ perfluoroalkyl group derived from the monool.

Compounds (12-1) to (12-4) are obtained by the reaction of the compounds (24-1) to (24-4) and $R^8OH$.

$$R^8OC(O)CF_2CF_2CF_2CF_2O(CF_2OCF_2CF_2CF_2CF_2CF_2O)_{x3\text{-}1}CF_2OCF_2CF_2CF_2CF_2C(O)OR^8 \quad (12\text{-}1)$$

$$R^8OC(O)CF_2CF_2CF_2CF_2CF_2O(CF_2OCF_2CF_2CF_2CF_2CF_2O)_{x3\text{-}1}CF_2OCF_2CF_2CF_2CF_2CF_2C(O)OR^8 \quad (12\text{-}2)$$

$$R^{f9}O(CF_2OCF_2CF_2CF_2CF_2CF_2O)_{x3\text{-}1}CF_2OCF_2CF_2CF_2CF_2C(O)OR^8 \quad (12\text{-}3)$$

$$R^{f9}O(CF_2OCF_2CF_2CF_2CF_2CF_2CF_2O)_{x3\text{-}1}CF_2OCF_2CF_2CF_2CF_2CF_2C(O)OR^8 \quad (12\text{-}4)$$

<Method (2) for Producing Compound (12)>

A method to prepare $CF_2\!=\!CFO(CF_2)_3C(O)CH_3$ from $HO(CH_2)_4OH$ is disclosed in Journal of Fluorine Chemistry, vol. 126, 2005, p. 521 to 527. In the method, by using $HO(CH_2)_5OH$ or $HO(CH_2)_6OH$ instead of $HO(CH_2)_4OH$, compound (31-1) or compound (31-2) is obtained.

$$CF_2\!=\!CFO(CF_2)_4C(O)OCH_3 \quad (31\text{-}1)$$

$$CF_2\!=\!CFO(CF_2)_5C(O)OCH_3 \quad (31\text{-}2)$$

The compound (31-1) or (31-2) is subjected to hydrogen reduction by using a reducing agent (such as sodium borohydride or lithium aluminum hydride) to obtain compound (32-1) or (32-2).

$$CF_2\!=\!CFO(CF_2)_4CH_2OH \quad (32\text{-}1)$$

$$CF_2\!=\!CFO(CF_2)_5CH_2OH \quad (32\text{-}2)$$

Patent Document 1 discloses a method in which $R^{f9}O(CF_2CF_2O\!-\!CF_2CF_2CF_2CF_2O)_{x3}C(O)R^{f8}$ is prepared from $CF_2\!=\!CFO(CF_2)_3CH_2OH$ and further $R^{f9}O(CF_2CF_2O\!-\!CF_2CF_2CF_2CF_2O)_{x3\text{-}1}CF_2CF_2OCF_2CF_2CF_2C(O)OR^8$ is prepared. In this method, by using the compound (32-1) or (32-2) instead of $CF_2\!=\!CFO(CF_2)_3CH_2OH$, compound (24-5) or (24-6) and further compound (12-5) or (12-6) are obtained.

$$R^{f9}O(CF_2CF_2O\!-\!CF_2CF_2CF_2CF_2CF_2O)_{x3}C(O)R^{f8} \quad (24\text{-}5)$$

$$R^{f9}O(CF_2CF_2O\!-\!CF_2CF_2CF_2CF_2CF_2CF_2O)_{x3}C(O)R^{f8} \quad (24\text{-}6)$$

$$R^{f9}O(CF_2CF_2O\!-\!CF_2CF_2CF_2CF_2CF_2)_{x3\text{-}1}CF_2CF_2OCF_2CF_2CF_2CF_2C(O)OR^8 \quad (12\text{-}5)$$

$$R^{f9}O(CF_2CF_2O\!-\!CF_2CF_2CF_2CF_2CF_2CF_2O)_{x3\text{-}1}CF_2CF_2OCF_2CF_2CF_2CF_2CF_2C(O)OR^8 \quad (12\text{-}6)$$

<Method for producing compound (13)>

The compounds (12-1) to (12-6) are subjected to hydrogen reduction using a reducing agent to obtain compounds (13-1) to (13-6).

$$HOCH_2CF_2CF_2CF_2CF_2O(CF_2CF_2CF_2CF_2CF_2O\!-\!CF_2O)_{x3}CF_2CF_2CF_2CF_2CH_2OH \quad (13\text{-}1)$$

$$HOCH_2CF_2CF_2CF_2CF_2CF_2O(CF_2CF_2CF_2CF_2CF_2CF_2O\!-\!CF_2O)_{x3}CF_2CF_2CF_2CF_2CF_2CH_2OH \quad (13\text{-}2)$$

$$R^{f9}O(CF_2CF_2CF_2CF_2CF_2O\!-\!CF_2O)_{x3}CF_2CF_2CF_2CF_2CH_2OH \quad (13\text{-}3)$$

$$R^{f9}O(CF_2CF_2CF_2CF_2CF_2CF_2O\!-\!CF_2O)_{x3}CF_2CF_2CF_2CF_2CF_2CH_2OH \quad (13\text{-}4)$$

$$R^{f9}O(CF_2CF_2O\!-\!CF_2CF_2CF_2CF_2CF_2O)_{x3\text{-}1}CF_2CF_2OCF_2CF_2CF_2CF_2CH_2OH \quad (13\text{-}5)$$

$$R^{f9}O(CF_2CF_2O\!-\!CF_2CF_2CF_2CF_2CF_2CF_2O)_{x3\text{-}1}CF_2CF_2OCF_2CF_2CF_2CF_2CF_2CH_2OH \quad (13\text{-}6)$$

<Method for Producing Compound (14)>

A metal fluoride (such as NaF, CsF, KF or AgF) and the compound (24-1) are reacted to obtain compound (25-1).

$$FC(O)CF_2CF_2CF_2CF_2O(CF_2CF_2CF_2CF_2CF_2O\!-\!CF_2O)_{x3}CF_2CF_2CF_2CF_2C(O)F \quad (25\text{-}1)$$

The compound (25-1) was iodized using an iodizing agent (such as LiI or iodine/potassium carbonate) to obtain compound (14-1).

$$ICF_2CF_2CF_2CF_2O(CF_2CF_2CF_2CF_2CF_2O\!-\!CF_2O)_{x3}CF_2CF_2CF_2CF_2I \quad (14\text{-}1)$$

Further, compounds (14-2) to (14-6) may be obtained instead of the compound (14-1) by using the compounds (24-2) to (24-6) instead of the compound (24-1).

ICF$_2$CF$_2$CF$_2$CF$_2$CF$_2$O(CF$_2$CF$_2$CF$_2$CF$_2$CF$_2$O—
  CF$_2$O)$_{x3}$CF$_2$CF$_2$CF$_2$CF$_2$CF$_2$I        (14-2)

R$^{f9}$O(CF$_2$CF$_2$CF$_2$CF$_2$CF$_2$O—
  CF$_2$O)$_{x3}$CF$_2$CF$_2$CF$_2$CF$_2$I              (14-3)

R$^{f9}$O(CF$_2$CF$_2$CF$_2$CF$_2$CF$_2$CF$_2$O—
  CF$_2$O)$_{x3}$CF$_2$CF$_2$CF$_2$CF$_2$CF$_2$I        (14-4)

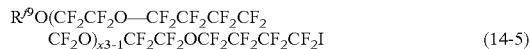

R$^{f9}$O(CF$_2$CF$_2$O—CF$_2$CF$_2$CF$_2$CF$_2$
  CF$_2$O)$_{x3-1}$CF$_2$CF$_2$OCF$_2$CF$_2$CF$_2$CF$_2$I   (14-5)

R$^{f9}$O(CF$_2$CF$_2$O—CF$_2$CF$_2$CF$_2$CF$_2$CF$_2$
  CF$_2$O)$_{x3-1}$CF$_2$CF$_2$OCF$_2$CF$_2$CF$_2$CF$_2$CF$_2$I   (14-6)

<Method for Producing Compound (11a)>

The compound (11a) may be produced, for example, in accordance with the method disclosed in e.g. Patent Document 1 or JP-A-2012-072272, using the compound (12-1) to (12-6), the compound (13-1) to (13-6) or the compound (14-1) to (14-6) as the starting material, via the compound (15a).

<Method for Producing Compound (11b)>

The compound (11b) may be produced, for example, in accordance with the method disclosed in WO2017/038832, using the compound (13-1) to (13-6) as the starting material, via the compound (15b).

<Method for Producing Compound (11c)>

The compound (11c) shown in paragraph [0061] may be produced, for example, in accordance with the method disclosed in WO2017/038830, using the compound (13-1) to (13-6) as the starting material, via the compound (15c) wherein s=0.

The compound (11c) shown in paragraph [0062] may be produced, for example, in accordance with the method disclosed in JP-A-2016-204656, using the compound (12-1) to (12-6) as the starting material, via the compound (15f) wherein G(R$^1$) is C(OH).

The compound (11c) shown in paragraph [0063] may be produced, for example, in accordance with the method disclosed in WO2017/0378830, using the compound (12-1) to (12-6) as the starting material, via the compound (15c) wherein s=1.

<Method for Producing Compound (11d)>

The compound (11d) may be produced, for example, in accordance with the method disclosed in JP-A-2016-037541 or WO2016/121211, using the compound (13-1) to (13-6) as the starting material, via the compound (15d).

<Method for Producing Compound (11e)>

The compound (11e) may be produced, for example, in accordance with the method disclosed in JP-A-2012-072272, using the compound (13-1) to (13-6) as the starting material, via the compound (15e) wherein v=0.

<Method for Producing Compound (11f)>

The compound (11f) wherein G(R$^6$) is C(OH) may be produced, for example, in accordance with the method disclosed in JP-A-2016-037541, using the compound (12-1) to (12-6) as the starting material, via the compound (15f).

<Method for Producing Compound (11g)>

The compound (11g) may be produced, for example, in accordance with the method disclosed in WO2016/121211, by polymerizing CH$_2$=CHSi(OCH$_3$)$_3$, CH$_2$=CHCH$_2$Si(OCH$_3$)$_3$ or the like, using the compound (14-1) to (14-6) as an initiator.

[Fluorinated Ether Composition]

The fluorinated ether composition of the present invention (hereinafter sometimes referred to as "the present composition") comprises at least one type of the present compound and other fluorinated ether compound.

As other fluorinated ether compound, a fluorinated ether compound formed as a by-product during production of the present compound (hereinafter sometimes referred to as "by-product fluorinated ether compound") and a known fluorinated ether compound used in the same applications as the present compound may be mentioned.

Other fluorinated ether compound is preferably one unlikely to impair the properties of the present compound.

As the by-product fluorinated ether compound, unreacted compounds (2) to (5); and fluorinated ether compounds formed through isomerization of some of the allyl groups into an inner olefin accompanying hydrosilylation during the production of the compound (1) may, for example, be mentioned.

As the known fluorinated ether compound, a commercially available fluorinated ether compound may, for example, be mentioned. In a case where the present composition contains a known fluorinated ether compound, it may have new effects such as compensation for the properties of the present compound.

The content of the present compound is preferably at least 60 mass % and less than 100 mass %, more preferably at least 70 mass % and less than 100 mass %, particularly preferably at least 80 mass % and less than 100 mass % in the present composition.

The content of other fluorinated ether compound is preferably more than 0 mass % and at most 40 mass %, more preferably more than 0 mass % and at most 30 mass %, particularly preferably more than 0 mass % and at most 20 mass % in the present composition.

The total content of the present compound and other fluorinated ether compound is preferably from 80 to 100 mass %, particularly preferably from 85 to 100 mass % in the present composition.

When the content of the present compound and the content of other fluorinated ether compound are within the above ranges, the surface layer is more excellent in initial water/oil repellency, abrasion resistance, fingerprint stain removability and light resistance.

The present composition may contain a component other than the present compound and other fluorinated ether compound within a range not to impair the effects of the present invention.

Other component may, for example, be a by-product formed during production of the present compound or the known fluorinated ether compound (excluding the by-product fluorinated ether compound) or a compound inevitable in production such as an unreacted raw material.

Further, known additives such as an acid catalyst or a basic catalyst to promote hydrolysis and condensation reaction of the hydrolyzable silyl group may be mentioned. The acid catalyst may, for example, be hydrochloric acid, nitric acid, acetic acid, sulfuric acid, phosphoric acid, sulfonic acid, methanesulfonic acid or p-toluenesulfonic acid. The basic catalyst may, for example, be sodium hydroxide, potassium hydroxide or ammonia.

The content of other component is preferably from 0 to 9.999 mass %, particularly preferably from 0 to 0.99 mass % in the present composition.

[Coating Liquid]

The coating liquid of the present invention (hereinafter sometimes referred to as "the present coating liquid") comprises the present compound or the present composition, and a liquid medium. The coating liquid may be a solution or a dispersion.

The liquid medium is preferably an organic solvent. The organic solvent may be a fluorinated organic solvent, may be a non-fluorinated organic solvent, or may contain both solvents.

The fluorinated organic solvent may, for example, be a fluorinated alkane, a fluorinated aromatic compound, a fluoroalkyl ether, a fluorinated alkylamine, a fluoroalcohol, etc.

The fluorinated alkane is preferably a $C_{4-8}$ compound. Commercially available products may, for example, be $C_6F_{13}H$ (manufactured by Asahi Glass Company, Limited, ASAHIKLIN (registered trademark) AC-2000), $C_6F_{13}C_2H_5$ (manufactured by Asahi Glass Company, Limited, ASAHIKLIN (registered trademark) AC-6000), and $C_2F_5CHFCHFCF_3$ (manufactured by Chemours, Vertrel (registered trademark) XF).

The fluorinated aromatic compound may, for example, be hexafluorobenzene, trifluoromethylbenzene, perfluorotoluene or bis(trifluoromethyl)benzene.

The fluoroalkyl ether is preferably a $C_{1-4}$ compound. Commercially available products may, for example, be $CF_3CH_2OCF_2CF_2H$ (manufactured by Asahi Glass Company, Limited, ASAHIKLIN (registered trademark) AE-3000), $C_4F_9OCH_3$ (manufactured by 3M, Novec (registered trademark) 7100), $C_4F_9OC_2H_5$ (manufactured by 3M, Novec (registered trademark) 7200), and $C_2F_5CF(OCH_3)C_3F_7$ (manufactured by 3M, Novec (registered trademark) 7300), The fluorinated alkylamine may, for example, be perfluorotripropylamine or perfluorotributylamine, The fluoroalcohol may, for example, be 2,2,3,3-tetrafluoropropanol, 2,2,2-trifluoroethanol or hexafluoroisopropanol.

The non-fluorinated organic solvent is preferably a compound consisting solely of hydrogen atoms and carbon atoms, or a compound consisting of only hydrogen atoms, carbon atoms and oxygen atoms, and may, for example, be a hydrocarbon-type solvent, an alcohol-type organic solvent, a ketone-type organic solvent, an ether-type organic solvent, or an ester-type organic solvent.

The content of the present compound or the present composition is preferably from 0.001 to 10 mass %, particularly preferably from 0.01 to 1 mass % in the present coating liquid.

The content of the liquid medium is preferably from 90 to 99.999 mass %, particularly preferably from 99 to 99.99 mass % in the present coating liquid.

[Article]

The article of the present invention (hereinafter sometimes referred to as "the present article" has a surface layer formed of the present compound or the present composition on the surface of a substrate.

The surface layer contains the present compound in a state where some or all of hydrolyzable silyl groups in the present compound are hydrolyzed and subjected to dehydration condensation reaction.

The thickness of the surface layer is preferably from 1 to 100 nm, particularly preferably from 1 to 50 nm. When the thickness of the surface layer is at least the lower limit value of the above range, the effect by the surface treatment is likely to be sufficiently obtained. When the thickness of the surface layer is at most the upper limit value of the above range, utilization efficiency will be high. The thickness of the surface layer can be calculated from the oscillation period of the interference pattern of the reflected X-ray, obtained by X-ray reflectance method using an X-ray diffractometer for thin film analysis (manufactured by Rigaku Corporation, ATX-G).

The substrate is not particularly limited so long as it is a substrate which is desired to have water/oil repellency imparted. The material of the substrate may, for example, be a metal, a resin, glass, sapphire, ceramic, stone or a composite material thereof. The glass may be chemically tempered. The substrate may have a primer film such as a $SiO_2$ film formed on its surface.

As the substrate, a substrate for a touch panel or a substrate for display is preferred, and a substrate for a touch panel is particularly preferred. As the material of a substrate for a touch panel, glass or a transparent resin is preferred.

[Method for Producing Article]

The present article may be produced, for example, by the following method.

A method of treating the surface of a substrate by dry coating method using the present compound or the present composition, to form a surface layer on the surface of the substrate.

A method of applying the coating liquid to the surface of a substrate by wet coating method, and removing the liquid medium to form a surface layer on the surface of the substrate.

As the dry coating method, a method such as vacuum deposition, CVD or sputtering may be mentioned. With a view to suppressing the decomposition of the present compound and from the viewpoint of simplicity of apparatus, vacuum deposition method is preferred. At the time of vacuum deposition, a pelletized material having a metal porous product of iron, steel of the like impregnated with the present compound or the present composition may be used.

The wet coating method may, for example, be a spin coating method, a wipe coating method, a spray coating method, a squeegee coating method, a dip coating method, a die coating method, an ink-jet method, a flow coating method, a roll coating method, a casting method, a Langmuir-Blodgett method, or a gravure coating method.

EXAMPLES

Now, the present invention will be described in further detail with reference to Examples, but the present invention is not limited to these Examples. Hereinafter, "%" is "mass %" unless otherwise specified. Ex. 1, 3, 5, 7, 9 and 11 are Examples of the present invention, and Ex. 2, 4, 6, 8, 10 and 12 are Comparative Examples.

Ex. 1

Ex. 1-1

Into a 100 ml three-necked flask, 3.50 g of $HOCH_2CF_2CF_2CF_2CH_2OH$, 39.5 g of the compound (21-1) obtained by the method disclosed in Ex. 1 of U.S. Pat. No. 4,740,579 were put and stirred at 60° C. 0.64 g of trifluoromethanesulfonic acid was dropwise added, followed by stirring for 24 hours. The crude product was dissolved in 300 mL of dichloromethane and washed twice with a mixed solution of 50 mL of a 35 mass % hydrogen peroxide solution, 100 mL of a 10 mass % aqueous sodium hydroxide solution and 250 mL of a saturated salt solution and further washed twice with 300 mL of a saturated salt solution. The recovered organic phase was concentrated by an evaporator and purified by silica gel column chromatography (developing solvent: $CF_3CH_2OCF_2CF_2H$ (manufactured by Asahi Glass Company, Limited, AE-3000)) to obtain 35.5 g (yield: 82.6%) of compound (22-1).

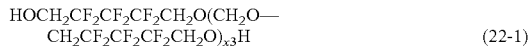
$HOCH_2CF_2CF_2CF_2CH_2O(CH_2O$—
$CH_2CF_2CF_2CF_2CH_2O)_{x3}H$ (22-1)

NMR spectrum of compound (22-1):
$^1$H-NMR (300.4 MHz, solvent: CDCl$_3$, reference: tetramethylsilane (TMS) δ (ppm): 4.8 (22H), 4.0 (48H).
$^{19}$F-NMR (282.7 MHz, solvent: CDCl$_3$, reference: CFCl$_3$) δ (ppm): −121 (44F), −123 (4F), −126 (24F).
Mean value of unit number x3: 11, number average molecular weight of compound (22-1): 2,680.

Ex. 1-2

Into a 100 ml eggplant flask, 35.0 g of the compound (22-1) obtained in Ex. 1-1, 2.75 g of sodium fluoride powder and 30 g of AE-3000 were put, and 21.7 g of CF$_3$CF$_2$CF$_2$OCF(CF$_3$)C(O)F was added. Under a nitrogen atmosphere, the mixture was stirred at 50° C. for 24 hours. After removing the sodium fluoride powder by a pressure filter, excess CF$_3$CF$_2$CF$_2$OCF(CF$_3$)COF and AE-3000 were distilled off under reduced pressure. The obtained crude product was diluted with C$_6$F$_{13}$H (manufactured by Asahi Glass Company, Limited, AC-2000) and passed through a silica gel column, whereupon the collected solution was concentrated by an evaporator to obtain 42.1 g (yield: 97.5%) of compound (23-1-1).

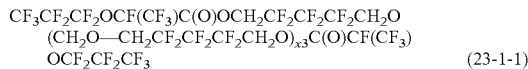
$CF_3CF_2CF_2OCF(CF_3)C(O)OCH_2CF_2CF_2CF_2CH_2O$
$(CH_2O$—$CH_2CF_2CF_2CF_2CH_2O)_{x3}C(O)CF(CF_3)$
$OCF_2CF_2CF_3$ (23-1-1)

NMR spectrum of compound (23-1-1):
$^1$H-NMR (300.4 MHz, solvent: CDCl$_3$, reference: TMS) δ (ppm): 4.8 (26H), 4.0 (44H).
$^{19}$F-NMR (282.7 MHz, solvent: CDCl$_3$, reference: CFCl$_3$) δ (ppm): −79 (2F), −81 (6F), −82 (6F), −86 (2F), −120 (48F), −126 (24F), −129 (4F), −132 (2F).
Mean value of unit number x3: 11, number average molecular weight of compound (23-1-1): 3,300.

Ex. 1-3

At a gas outlet of a 500 mL nickel autoclave, a condenser maintained at 20° C., a NaF pellet packed layer and a condenser maintained at 0° C. were installed in series. A liquid returning line to return the solution collected from the condenser maintained at 0° C. to the autoclave was installed.

Into the autoclave, 250 g of ClCF$_2$CFCl$_2$ (hereinafter sometimes referred to as "R-113") was put and stirred while maintaining the temperature at 25° C. Into the autoclave, nitrogen gas was blown at 25° C. for one hour, and then, 20% fluorine gas was blown at 25° C. for one hour at a flow rate of 4.7 L/hour. While blowing the 20% fluorine gas at the same flow rate, a solution having 20.0 g of the compound (23-1-1) obtained in Ex. 1-2 dissolved in 100 g of R-113, was injected into the autoclave over a period of 4 hours. While blowing the 20% fluorine gas at the same flow rate, the internal pressure of the autoclave was raised to 0.15 MPa (gauge pressure). Into the autoclave, 4 mL of a benzene solution containing 0.03 g/mL of benzene in R-113, was injected while heating to 40° C. from 25° C., and then the benzene solution inlet of the autoclave was closed. After stirring for 15 minutes, 4 mL of the benzene solution was again injected while maintaining the temperature at 40° C., and then the inlet was closed. The same operation was repeated four more times. The total amount of benzene injected was 0.6 g. While blowing the 20% fluorine gas at the same flow rate, stirring was continued for 1 hour. The pressure in the autoclave was brought to atmospheric pressure, and nitrogen gas was blown in for 1 hour. The content of the autoclave was concentrated by an evaporator to obtain 27.5 g (yield: 99.5%) of compound (24-1-1).

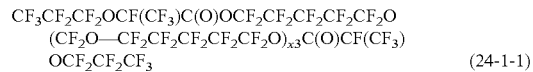
$CF_3CF_2CF_2OCF(CF_3)C(O)OCF_2CF_2CF_2CF_2CF_2O$
$(CF_2O$—$CF_2CF_2CF_2CF_2O)_{x3}C(O)CF(CF_3)$
$OCF_2CF_2CF_3$ (24-1-1)

NMR spectrum of compound (24-1-1):
$^{19}$F-NMR (282.7 MHz, solvent: CDCl$_3$, reference: CFCl$_3$) δ (ppm): −51 (22F), −80 (2F), −81 (6F), −82 (6F), −84 (4F), −85 (44F), −87 (2F), −118 (4F), −122 (20F), −123 (4F), −125 (44F), −130 (4F), −133 (2F).
Mean value of unit number x3: 11, number average molecular weight of compound (24-1-1): 4,560.

Ex. 1-4

Into a round bottom flask made of a tetrafluoroethylene/perfluoro(alkoxy vinyl ether) copolymer (hereinafter sometimes referred to as "PFA"), 27.0 g of the compound (24-1-1) obtained in Ex. 1-3 and 30 g of AE-3000 were put. The mixture was stirred while cooling in an ice bath, and in a nitrogen atmosphere, 1.9 g of methanol was slowly dropwise added from a dropping funnel. While bubbling with nitrogen, the mixture was stirred for 12 hours. The reaction mixture was concentrated by an evaporator to obtain 22.9 g (yield: 98.7%) of compound (12-1-1).

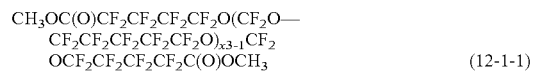
$CH_3OC(O)CF_2CF_2CF_2CF_2O(CF_2O$—
$CF_2CF_2CF_2CF_2O)_{x3-1}CF_2$
$OCF_2CF_2CF_2CF_2C(O)OCH_3$ (12-1-1)

NMR spectrum of compound (12-1-1):
$^1$H-NMR (300.4 MHz, solvent: CDCl$_3$, reference: TMS) δ (ppm): 3.9 (6H).
$^{19}$F-NMR (282.7 MHz, solvent: CDCl$_3$, reference: CFCl$_3$) δ (ppm): −51 (22F), −85 (44F), −118 (4F), −122 (20F), −123 (4F), −126 (44F).
Mean value of unit number x3-1: 10, number average molecular weight of compound (12-1-1): 3,920.

Ex. 1-5

Into a 50 mL eggplant flask, 10.0 g of the compound (12-1-1) obtained in Ex. 1-4, 0.90 g of H$_2$NCH$_2$C(CH$_2$CH=CH$_2$)$_3$ and 10 g of AE-3000 were put and stirred for 12 hours. The obtained reaction mixture was diluted with 30.0 g of AE-3000 and purified by silica gel column chromatography (developing solvent: AE-3000) to obtain 10.2 g (yield: 95.5%) of compound (15c-1).

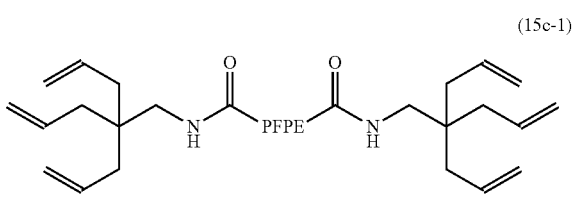

PFPE = $CF_2CF_2CF_2CF_2O(CF_2O$—$CF_2CF_2CF_2CF_2O)_{x3-1}CF_2OCF_2CF_2CF_2CF_2$

NMR Spectrum of compound (15c-1):
$^1$H-NMR (300.4 MHz, solvent: CDCl$_3$, reference: TMS) δ (ppm): 2.1 (12H), 3.4 (4H), 5.2 (12H), 6.2 to 5.9 (6H).

$^{19}$F-NMR (282.7 MHz, solvent: CDCl$_3$, reference: CFCl$_3$) δ (ppm): −51 (22F), −85 (44F), −120 (4F), −122 (20F), −123 (4F), −126 (44F).

Mean value of unit number x3-1: 10, number average molecular weight of compound (15c-1): 4,190.

Ex. 1-6

Into a 10 mL PFA sample tube, 5.0 g of the compound (15c-1) obtained in Ex. 1-5, 0.03 g of a xylene solution (platinum content: 3%) of a platinum/1,3-divinyl-1,1,3,3-tetramethyldisiloxane complex, 1.43 g of HSi(OCH$_3$)$_3$, 0.01 g of aniline and 5.0 g of 1,3-bis(trifluoromethyl)benzene were put and stirred at 40° C. for 10 hours. After completion of the reaction, the solvent, etc. were distilled off under reduced pressure, followed by filtration through a membrane filter having a pore size of 1.0 μm to obtain 5.82 g (yield: 99.1%) of compound (11c-1).

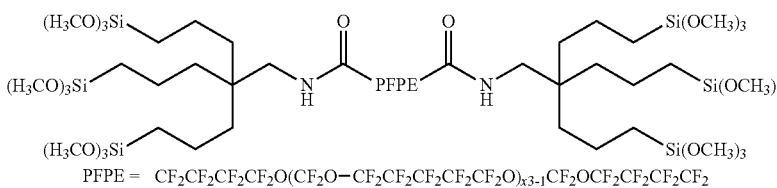

PFPE = CF$_2$CF$_2$CF$_2$CF$_2$O(CF$_2$O—CF$_2$CF$_2$CF$_2$CF$_2$CF$_2$O)$_{x3-1}$CF$_2$OCF$_2$CF$_2$CF$_2$CF$_2$ (11c-1)

NMR Spectrum of compound (11c-1):
$^1$H-NMR (300.4 MHz, solvent: CDCl$_3$, reference: TMS) δ (ppm): 0.75 (12H), 1.3 to 1.6 (24H), 3.4 (4H), 3.7 (54H).
$^{19}$F-NMR (282.7 MHz, solvent: CDCl$_3$, reference: CFCl$_3$) δ (ppm): −51 (22F), −85 (44F), −120 (4F), −122 (20F), −123 (4F), −126 (44F).

Mean value of unit number x3-1: 10, number average molecular weight of compound (11c-1): 4,920. The proportion of the unit (α) is 0.45, from m1=11, m4=1 and m5=10.

Ex. 2

Ex. 2-1

Into a 50 mL eggplant flask, 20.0 g of a perfluoropolyether compound having a carboxy group on both terminals and having (CF$_2$O) and (CF$_2$CF$_2$O) randomly bonded as the unit of the poly(oxyperfluoroalkylene chain) (manufactured by Solvay Solexis, FOMBLIN (registered trademark) ZDIAC4000), 5.0 g of methanol and 20 g of AE-3000 were put and stirred at 50° C. for 12 hours. The solvent, etc. were distilled off from the obtained reaction mixture, followed by dilution with 50.0 g of AE-3000 and purification by silica gel column chromatography (developing solvent: AE-3000) to obtain 14.3 g (yield: 71.0%) of compound (42-1).

CH$_3$OC(O)CF$_2$O{(CF$_2$O)$_1$(CF$_2$CF$_2$O)$_{x2}$}CF$_2$C(O)OCH$_3$ (42-1)

NMR Spectrum of compound (42-1):
$^1$H-NMR (300.4 MHz, solvent: CDCl$_3$, reference: TMS) δ (ppm): 3.9 (6H).
$^{19}$F-NMR (282.7 MHz, solvent: CDCl$_3$, reference: CFCl$_3$) δ (ppm): −52 to −56 (38F), −78 (2F), −80 (2F), −89 to −91 (84F).

Mean value of unit number x1: 20, mean value of unit number x2: 21, number average molecular weight of compound (42-1): 3,990.

Ex. 2-2

In the same manner as in Ex. 1-5 except that 10.0 g of the compound (42-1) was used instead of the compound (12-1-1), 10.3 g (yield: 96.6%) of compound (45c-1) was obtained.

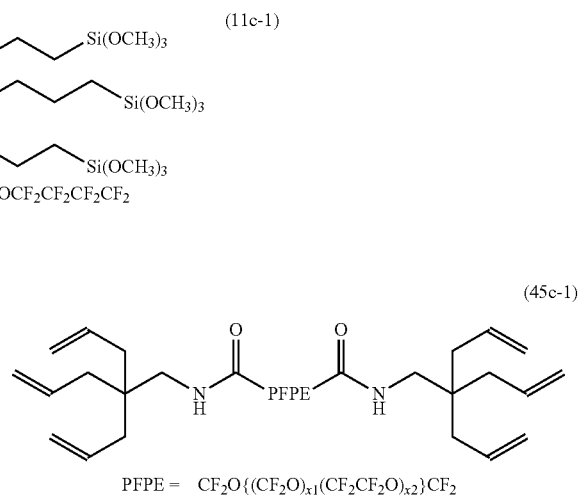

PFPE = CF$_2$O{(CF$_2$O)$_{x1}$(CF$_2$CF$_2$O)$_{x2}$}CF$_2$ (45c-1)

NMR Spectrum of compound (45C-1):
$^1$H-NMR (300.4 MHz, solvent: CDCl$_3$, reference: TMS) δ (ppm): 2.1 (12H), 3.4 (4H), 5.2 (12H), 6.2 to 5.9 (6H).
$^{19}$F-NMR (282.7 MHz, solvent: CDCl$_3$, reference: CFCl$_3$) δ (ppm): −52 to −56 (38F), −77 (2F), −79 (2F), −89 to −91 (84F).

Mean value of unit number x1: 20, mean value of unit number x2: 21, number average molecular weight of compound (45c-1): 4,260.

Ex. 2-3

In the same manner as in Ex. 1-6 except that 5.0 g of the compound (45c-1) was used instead of the compound (15c-1), 5.78 g (yield: 98.6%) of compound (41c-1) was obtained.

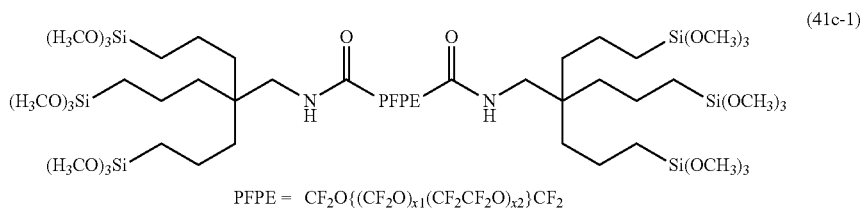

PFPE = CF$_2$O{(CF$_2$O)$_{x1}$(CF$_2$CF$_2$O)$_{x2}$}CF$_2$ (41c-1)

NMR Spectrum of compound (41c-1):
$^1$H-NMR (300.4 MHz, solvent: CDCl$_3$, reference: TMS) δ (ppm): 0.75 (12H), 1.3 to 1.6 (24H), 3.4 (4H), 3.7 (54H).
$^{19}$F-NMR (282.7 MHz, solvent: CDCl$_3$, reference: CFCl$_3$) δ (ppm): −52 to −56 (38F), −77 (2F), −79 (2F), −89 to −91 (84F).

Mean value of unit number x1: 20, mean value of unit number x2: 21, number average molecular weight of compound (41c-1): 4,990. The proportion of the unit (α) is 0 from m5=m6=0.

Ex. 3

Ex. 3-1

In the same manner as in Ex. 1-1 except that 1.5 g of CF$_3$CH$_2$OH was used instead of HOCH$_2$CF$_2$CF$_2$CF$_2$CH$_2$OH, the amount of the compound (21-1) was changed to 35.0 g, and the amount of trifluoromethanesulfonic acid was changed to 0.70 g, 24.4 g (yield: 66.8%) of compound (22-3-1) was obtained.

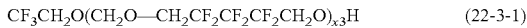

NMR Spectrum of compound (22-3-1):
$^1$H-NMR (300.4 MHz, solvent: CDCl$_3$, reference: TMS) δ (ppm): 4.8 (22H), 4.0 (44H), 3.9 (2H).
$^{19}$F-NMR (282.7 MHz, solvent: CDCl$_3$, reference: CFCl$_3$) δ (ppm): −75 (3F), −121 (42F), −123 (2F), −126 (22F).

Mean value of unit number x3: 11, number average molecular weight of compound (22-3-1): 2,570.

Ex. 3-2

In the same manner as in Ex. 1-2 except that 24.0 g of the compound (22-3-1) was used instead of the compound (22-1), the amount of sodium fluoride was changed to 1.96 g, and the amount of CF$_3$CF$_2$CF$_2$OCF(CF$_3$)C(O)F was changed to 9.32 g, 26.3 g (yield: 97.7%) of compound (23-3-1) was obtained.

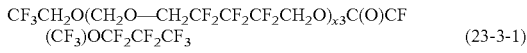

NMR Spectrum of compound (23-3-1):
1H-NMR (300.4 MHz, solvent: CDCl3, reference: TMS) δ (ppm): 4.8 (24H), 4.0 (42H), 3.9 (2H).
$^{19}$F-NMR (282.7 MHz, solvent: CDCl3, reference: CFCl3) δ (ppm): −75 (3F), −79 (1F), −81 (3F), −82 (3F), −86 (1F), −120 (44F), −126 (22F), −129 (2F), −132 (1F).

Mean value of unit number x3: 11, number average molecular weight of compound (23-3-1): 2,880.

Ex. 3-3

In the same manner as in Ex. 1-3 except that 20.0 g of the compound (23-3-1) was used instead of the compound (23-1-1), 28.2 g (yield: 98.9%) of compound (24-3-1) was obtained.

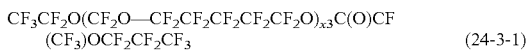

NMR Spectrum of compound (24-3-1):
$^{19}$F-NMR (282.7 MHz, solvent: CDCl$_3$, reference: CFCl$_3$) δ (ppm): −51 (22F), −80 (1F), −81 (3F), −82 (3F), −84 (2F), −85 (42F), −87 (4F), −90 (2F), −118 (2F), −122 (20F), −123 (2F), −125 (42F), −130 (2F), −133 (1F).

Mean value of unit number x3: 11, number average molecular weight of compound (24-3-1): 4,100.

Ex. 3-4

In the same manner as in Ex. 1-4 except that 27.0 g of the compound (24-3-1) was used instead of the compound (24-1-1) and the amount of methanol was changed to 1.05 g, 24.4 g (yield: 98.0%) of compound (12-3-1) was obtained.

NMR Spectrum of compound (12-3-1):
$^1$H-NMR (300.4 MHz, solvent: CDCl$_3$, reference: TMS) δ (ppm): 3.9 (3H).
$^{19}$F-NMR (282.7 MHz, solvent CDCl$_3$, reference: CFCl$_3$) δ (ppm): −51 (22F), −85 (42F), −87 (3F), −90 (2F), −118 (2F), −122 (20F), −123 (2F), −126 (42F).

Mean value of unit number x3-1: 10, number average molecular weight of compound (12-3-1): 3,780.

Ex. 3-5

In the same manner as in Ex. 1-5 except that 10.0 g of the compound (12-3-1) was used instead of the compound (12-1-1) and the amount of H$_2$NCH$_2$C(CH$_2$CH=CH$_2$)$_3$ was changed to 0.50, 9.9 g (yield: 95.6%) of compound (15c-2) was obtained.

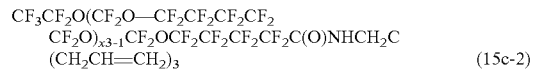

NMR Spectrum of compound (15c-2):
$^1$H-NMR (300.4 MHz, solvent: CDCl$_3$, reference: TMS) δ (ppm): 2.1 (6H), 3.4 (2H), 5.2 (6H), 6.2 to 5.9 (3H).
$^{19}$F-NMR (282.7 MHz, solvent: CDCl$_3$, reference: CFCl$_3$) δ (ppm): −51 (22F), −85 (42F), −87 (3F), −90 (2F), −120 (2F), −122 (20F), −123 (2F), −126 (42F).

Mean value of unit number x3-1: 10, number average molecular weight of compound (15c-2): 3,910.

Ex. 3-6

In the same manner as in Ex. 1-6 except that 5.0 g of the compound (15c-2) was used instead of the compound (15c-1), the amount of the xylene solution (platinum content: 3%) of a platinum/1,3-divinyl-1,1,3,3-tetramethyldisiloxane complex was changed to 0.02 g, the amount of HSi(OCH$_3$)$_3$ was changed to 0.78 g, and the amount of aniline was changed to 0.005 g, 5.45 g (yield: 99.7%) of compound (11c-2) was obtained.

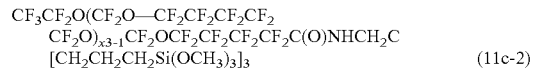

NMR Spectrum of compound (11c-2):
$^1$H-NMR (300.4 MHz, solvent: CDCl$_3$, reference: TMS) δ (ppm): 0.75 (6H), 1.3 to 1.6 (12H), 3.4 (2H), 3.7 (27H).
$^{19}$F-NMR (282.7 MHz, solvent CDCl$_3$, reference: CFCl$_3$) δ (ppm): −51 (22F), −85 (42F), −87 (3F), −90 (2F), −120 (2F), −122 (20F), −123 (2F), −126 (42F).

Mean value of unit number x3-1: 10, number average molecular weight of compound (11c-2): 4.280. The proportion of the unit (α) is 0.48 from m1=11 and m5=10.

Ex. 4

Compound (41c-2) was obtained in accordance with the method disclosed in WO2017/38830, Ex. 16.

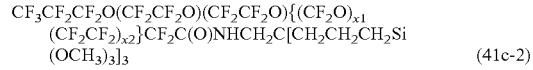

NMR Spectrum of compound (41c-2):
$^{1}$H-NMR (300.4 MHz, solvent: CDCl$_3$, reference: TMS) δ (ppm): 0.75 (6H), 1.3 to 1.6 (12H), 3.4 (2H), 3.7 (27H).
$^{19}$F-NMR (282.7 MHz, solvent: CDCl$_3$, reference: CFCl$_3$) δ (ppm): −52 to −56 (38F), −78 (2F), −80 (2F), −89 to −91 (84F).

Mean value of unit number x1: 22, mean value of unit number x2: 19, number average molecular weight of compound (41c-2): 4,480. The proportion of the unit (α) is 0 from m5=m6=0.

Ex. 5

Ex. 5-1

Compound (31-2) was obtained in accordance with the method disclosed in Journal of Fluorine Chemistry, vol. 126, 2005, p. 521 to 527 except that HO(CH$_2$)$_6$OH was used instead of HO(CH$_2$)$_4$OH.

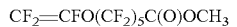
(31-2)

NMR Spectrum of compound (31-2):
$^{1}$H-NMR (300.4 MHz, solvent: CDCl$_3$, reference: TMS) δ (ppm): 3.9 (3H).
$^{19}$F-NMR (282.7 MHz, solvent CDCl$_3$, reference: CFCl$_3$) δ (ppm): −85 (2F), −114 (1F), −118 (2F), −122 (3F), −123 (2F), −126 (2F), −135 (1F).

Ex. 5-2

The compound (31-2) was reduced by the method disclosed in Patent Document 1, Ex. 1-1, to obtain compound (32-2).

(32-2)

NMR Spectrum of compound (32-2):
$^{1}$H-NMR (300.4 MHz, solvent: CDCl$_3$, reference: TMS) δ (ppm): 4.0 (2H).
$^{19}$F-NMR (282.7 MHz, solvent CDCl$_3$, reference: CFCl$_3$) δ (ppm): −85 (2F), −114 (1F), −121 (2F), −122 (3F), −123 (2F), −126 (2F), −135 (1F).

Ex. 5-3

The compound (32-2) was subjected to addition polymerization in accordance with the method disclosed in Patent Document 1, Ex. 6, followed by column purification to obtain compound (22-6-1).

(22-6-1)

NMR Spectrum of compound (22-6-1):
$^{1}$H-NMR (300.4 MHz, solvent: CDCl$_3$, reference: TMS) δ (ppm): 3.7 (3H), 4.0 (2H), 4.4 (18H), 6.1 (10H).
$^{19}$F-NMR (282.7 MHz, solvent: CDCl$_3$, reference: CFCl$_3$) δ (ppm): −86 (20F), −91 (20F), −121 (38F), −122 (20F), −123 (2F), −126 (20F), −145 (10F).

Mean value of unit number x3: 10, number average molecular weight of compound (22-6-1): 3,810.

Ex. 5-4

In the same manner as in Ex. 1-2 except that 30.0 g of the compound (22-6-1) was used instead of the compound (22-1), the amount of the sodium fluoride powder was changed to 1.96 g, and the amount of CF$_3$CF$_2$CF$_2$OCF(CF$_3$)C(O)F was changed to 9.32 g, 32.1 g (yield: 98.9%) of compound (23-6-1) was obtained.

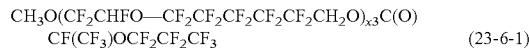
(23-6-1)

NMR Spectrum of compound (23-6-1):
$^{1}$H-NMR (300.4 MHz, solvent: CDCl$_3$, reference: TMS) δ (ppm): 3.7 (3H), 4.4 (18H), 4.8 (2H), 6.1 (10H).
$^{19}$F-NMR (282.7 MHz, solvent CDCl$_3$, reference: CFCl$_3$) δ (ppm): −79 (1F), −81 (3F), −82 (3F), −86 (21F), −91 (20F), −120 (2F), −121 (38F), −122 (20F), −126 (20F), −129 (2F), −131 (1F), −145 (10F).

Mean value of unit number x3: 10, number average molecular weight of compound (23-6-1): 4,120.

Ex. 5-5

In the same manner as in Ex. 1-3 except that 20.0 g of the compound (23-6-1) was used instead of the compound (23-1-1), 22.4 g (yield: 97.9%) of compound (24-6-1) was obtained.

(24-6-1)

NMR Spectrum of compound (24-6-1):
$^{19}$F-NMR (282.7 MHz, solvent: CDCl$_3$, reference: CFCl$_3$) δ (ppm): −56 (3F), −80 (1F), −82 (6F), −83 (2F), −85 (38F), −87 (1F), −91 (40F), −122 (40F), −125 (40F), −130 (2F), −132 (1F).

Mean value of unit number x3: 10, number average molecular weight of compound (24-6-1): 4,720.

Ex. 5-6

In the same manner as in Ex. 1-4 except that 22.0 g of the compound (24-6-1) was used instead of the compound (24-1-1) and the amount of methanol was changed to 0.75 g, 20.2 g (yield: 98.5%) of compound (12-6-1) was obtained.

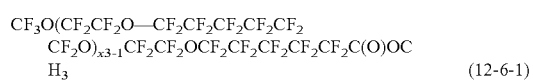
(12-6-1)

NMR Spectrum of compound (12-6-1):
$^{1}$H-NMR (300.4 MHz, solvent: CDCl$_3$, reference: TMS) δ (ppm): 3.9 (3H).
$^{19}$F-NMR (282.7 MHz, solvent CDCl$_3$, reference: CFCl$_3$) δ (ppm): −56 (3F), −85 (38F), −91 (40F), −118 (2F), −122 (38F), −123 (2F), −125 (38F).

Mean value of unit number x3: 10, number average molecular weight of compound (12-6-1): 4,400.

Ex. 5-7

In the same manner as in Ex. 1-5 except that 10.0 g of the compound (12-6-1) was used instead of the compound (12-1-1) and the amount of H$_2$NCH$_2$C(CH$_2$CH=CH$_2$)$_3$ was changed to 0.45 g, 9.6 g (yield: 96.1%) of compound (15c-3) was obtained.

(15c-3)

NMR Spectrum of compound (15c-3):
$^{1}$H-NMR (300.4 MHz, solvent: CDCl$_3$, reference: TMS) δ (ppm): 2.1 (6H), 3.4 (2H), 5.2 (6H), 6.2 to 5.9 (3H).
$^{19}$F-NMR (282.7 MHz, solvent: CDCl$_3$, reference: CFCl$_3$) δ (ppm): −56 (3F), −85 (38F), −91 (40F), −120 (2F), −122 (38F), −125 (40F).

Mean value of unit number x3: 10, number average molecular weight of compound (15c-3): 4,530.

Ex. 5-8

In the same manner as in Ex. 1-6 except that 5.0 g of the compound (15c-3) was used instead of the compound (15c-1), the amount of the xylene solution (platinum content: 3%) of a platinum/1,3-divinyl-1,1,3,3-tetramethyldisiloxane complex was changed to 0.02 g, the amount of $HSi(OCH_3)_3$ was changed to 0.67 g, and the amount of aniline was changed to 0.005 g, 5.32 g (yield: 98.4%) of compound (11c-3) was obtained.

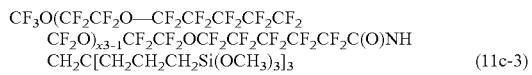
(11c-3)

NMR Spectrum of compound (11c-3):
$^1$H-NMR (300.4 MHz, solvent: $CDCl_3$, reference: TMS) δ (ppm): 0.75 (6H), 1.3 to 1.6 (12H), 3.4 (2H), 3.7 (27H).
$^{19}$F-NMR (282.7 MHz, solvent $CDCl_3$, reference: $CFCl_3$) δ (ppm): −56 (3F), −85 (38F), −91 (40F), −120 (2F), −122 (38F), −125 (40F).

Mean value of unit number x3: 10, number average molecular weight of compound (11c-3): 4,900. The proportion of the unit (α) is 0.48 from m2=11 and m6=10.

Ex. 6

Ex. 6-1

Compound (41c-3) was obtained in accordance with the method disclosed in WO2017/38830, Ex 11.

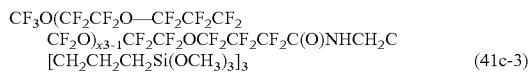
(41c-3)

Mean value of unit number x3: 14, number average molecular weight of compound (41c-3): 5,270. The proportion of the unit (α) is 0 from m5=m6=0.

Ex. 7 to 12: Production and Evaluation of Article

Using the compound obtained in each of Ex. 1 to 6, surface treatment of a substrate was conducted to obtain an article in each of Ex. 7 to 12. As the surface treatment method, in each Ex., the following dry coating and wet coating method were, respectively, employed. As the substrate, chemically tempered glass was used. With respect to the obtained article, evaluations were carried out by the following methods. The results are shown in Table 1.
(Dry Coating Method)

The dry coating was carried out by using a vacuum deposition apparatus (manufactured by ULVAC Co., VTR-350M) (vacuum deposition method), 0.5 g of the compound obtained in each of Ex. 1 to 6 and 13 to 16 was filled in a boat made of molybdenum in the vacuum deposition apparatus, and inside of the vacuum deposition apparatus was evacuated to a level of at most $1 \times 10^{-3}$ Pa. The boat having the compound placed therein, was heated at a temperature raising rate of at most 10° C./min, and at the time when the vapor deposition rate by a quartz oscillator film thickness meter exceeded 1 nm/sec, the shutter was opened to initiate film deposition on the surface of a substrate. When the film thickness became about 50 nm, the shutter was closed to terminate film deposition on the surface of the substrate. The substrate on which the compound was deposited, was subjected to heat treatment at 200° C. for 30 minutes, followed by washing with dichloropentafluoropropane (manufactured by Asahi Glass Company, Limited, AK-225), to obtain an article having a surface layer on the surface of the substrate.
(Wet Coating Method)

The compound obtained in each of Ex. 1 to 6 and 13 to 16, and $C_4F_9OC_2H_5$ (manufactured by 3M, Novec (registered trademark) 7200) as a medium, were mixed to prepare a coating liquid having a solid content concentration of 0.05%. A substrate was dipped in the coating liquid and allowed to stand for 30 minutes, whereupon the substrate was taken out (dip coating method). The coating film was dried at 200° C. for 30 minutes and washed with AK-225, to obtain an article having a surface layer on the surface of the substrate.
(Evaluation Methods)
<Method for Measuring Contact Angle>

The contact angle of about 2 μL of distilled water or n-hexadecane placed on the surface of the surface layer, was measured by using a contact angle measuring apparatus (manufactured by Kyowa Interface Science Co., Ltd., DM-500). Measurements were conducted at five different points on the surface of the surface layer, and the average value was calculated. For the calculation of the contact angle, a 2θ method was employed.
<Initial Contact Angle>

With respect to the surface layer, the initial water contact angle and the initial n-hexadecane contact angle were measured by the above-described measuring method. The evaluation standards are as follows.

Initial water contact angle:
⊚ (excellent): at least 115 degrees.
○ (good): at least 110 degrees and less than 115 degrees.
Δ (acceptable): at least 100 degrees and less than 110 degrees.
× (poor): less than 100 degrees.

Initial n-hexadecane contact angle:
⊚ (excellent): at least 66 degrees.
○ (good): at least 65 degrees and less than 66 degrees.
Δ (acceptable): at least 63 degrees and less than 65 degrees.
× (poor): less than 63 degrees.
<Abrasion Resistance (Steel Wool)>

With respect to the surface layer, in accordance with JIS L0849: 2013 (ISO 105-X12: 2001), using a reciprocating traverse testing machine (manufactured by KNT Co.), steel wool Bon Star (#0000) was reciprocated 10,000 times under a pressure of 98.07 kPa at a speed of 320 cm/min, whereupon the water contact angle was measured. The smaller the decrease in water repellency (water contact angle) after the abrasion, the smaller the decrease in performance due to friction, and the better the abrasion resistance. The evaluation standards are as follows.

⊚ (excellent): The change in water contact angle after reciprocation of 10,000 times is at most 2 degrees.
○ (good): The change in water contact angle after reciprocation of 10,000 times is more than 2 degrees and at most 5 degrees.
Δ (acceptable): The change in water contact angle after reciprocation of 10,000 times is more than 5 degrees and at most 10 degrees.
× (poor): The change in water contact angle after reciprocation of 10,000 times is more than 10 degrees.
<Abrasion Resistance (Eraser)>

With respect to the surface layer, in accordance with JIS L0849: 2013 (ISO 105-X12: 2001), using a reciprocating traverse testing machine (manufactured by KNT Co.), Rubber Eraser (manufactured by Minoan) was reciprocated 30,000 times under a load of 4.9 N at a speed of 60 rpm, whereupon the water contact angle was measured. The smaller the decrease in water repellency (water contact angle) after the abrasion, the smaller the decrease in performance due to friction, and the better the abrasion resistance. The evaluation standards are as follows.

⊚ (excellent): The change in water contact angle after reciprocation of 30,000 times is at most 2 degrees.

◯ (good): The change in water contact angle after reciprocation of 30,000 times is more than 2 degrees and at most 5 degrees.

Δ (acceptable): The change in water contact angle after reciprocation of 30,000 times is more than 5 degrees and at most 10 degrees.

× (poor): The change in water contact angle after reciprocation of 30,000 times is more than 10 degrees.

<Fingerprint Stain Removability>

An artificial fingerprint liquid (liquid consisting of oleic acid and squalene) was deposited on a flat surface of a silicon rubber plug, and then, extra oil was wiped off by a nonwoven fabric (manufactured by Asahi Kasei Corporation, BEMCOT (registered trademark) M-3), to prepare a stamp for fingerprint. The fingerprint stamp was placed on the surface layer and pressed under a load of 9.8 N for 10 seconds. The haze at a portion having a fingerprint adhered, was measured by a haze meter and taken as an initial value. With respect to the portion having a fingerprint adhered, using a reciprocating traverse testing machine (manufactured by KNT Co.) having tissue paper attached, wiping was carried out under a load of 4.9 N. The value of haze was measured every one reciprocation for wiping, and the number of wiping times until the haze became at most 10% from the initial value, was measured. The smaller the number of wiping times, the easier the removal of fingerprint stain, and the better the fingerprint stain removability. The evaluation standards are as follows.

XLS+), light (650 W/m$^2$, 300 to 700 nm) was applied at a black panel temperature of 63° C. for 1,000 hours, whereupon the water contact angle was measured. The smaller the decrease in water contact angle after the accelerated light resistance test, the smaller the decrease in performance due to light, and the better the light resistance. The evaluation standards are as follows.

⊚ (excellent): The change in water contact angle after the accelerated light resistance test is at most 2 degrees.

◯ (good): The change in water contact angle after the accelerated light resistance test is more than 2 degrees and at most 5 degrees.

Δ (acceptable): The change in water contact angle after the accelerated light resistance test is more than 5 degrees and at most 10 degrees.

× (poor): The change in water contact angle after the accelerated light resistance test is more than 10 degrees.

<Lubricity>

The dynamic friction coefficient of the surface layer to an artificial skin (manufactured by Idemitsu Technofine Co., Ltd., PBZ13001) was measured by means of a load variation type friction abrasion test system (manufactured by Shinto Scientific Co., Ltd., HHS2000) under conditions of a contact area of 3 cm×3 cm and a load of 0.98N. The smaller the dynamic friction coefficient, the better the lubricity. The evaluation standards are as follows.

⊚ (excellent): The dynamic friction coefficient is at most 0.2.

◯ (good): The dynamic friction coefficient is more than 0.2 and at most 0.3.

Δ (acceptable): The dynamic friction coefficient is more than 0.3 and at most 0.4.

× (poor): The dynamic friction coefficient is more than 0.4.

TABLE 1

| Ex. | | | 7 | 8 (Comparison) | 9 | 10 (Comparison) | 11 | 12 (Comparison) |
|---|---|---|---|---|---|---|---|---|
| Fluorinated ether compound | | | Compound (11c-1) | Compound (41c-1) | Compound (11c-2) | Compound (41c-2) | Compound (11c-3) | Compound (41c-3) |
| Dry coating method | Initial contact angle | Water | ◯ | Δ | ⊚ | ⊚ | ⊚ | ⊚ |
| | | n-Hexadecane | Δ | × | ⊚ | ⊚ | ⊚ | ⊚ |
| | Abrasion resistance (steel wool) | | Δ | × | ◯ | Δ | ◯ | Δ |
| | Abrasion resistance (eraser) | | Δ | Δ | Δ | Δ | Δ | Δ |
| | Fingerprint stain removability | | ◯ | ◯ | ⊚ | ⊚ | ⊚ | ⊚ |
| | Light resistance | | Δ | × | Δ | × | ◯ | × |
| | Lubricity | | Δ | ◯ | ◯ | ⊚ | Δ | Δ |
| Wet coating method | Initial contact angle | Water | ◯ | Δ | ⊚ | ⊚ | ⊚ | ⊚ |
| | | n-Hexadecane | Δ | × | ⊚ | ⊚ | ⊚ | ⊚ |
| | Abrasion resistance (steel wool) | | Δ | × | ◯ | Δ | Δ | Δ |
| | Abrasion resistance (eraser) | | Δ | × | Δ | × | Δ | × |
| | Fingerprint stain removability | | ◯ | ◯ | ⊚ | ⊚ | ⊚ | ⊚ |
| | Light resistance | | Δ | × | Δ | × | ◯ | × |
| | Lubricity | | Δ | ◯ | ◯ | ⊚ | Δ | Δ |

⊚ (excellent): The number of wiping times is at most 3 times.

◯ (good): The number of wiping times is from 4 to 5 times.

Δ (acceptable): The number of wiping times is from 6 to 8 times.

× (poor): The number of wiping times is at least 9 times.

<Light Resistance>

To the surface layer, by means of a tabletop xenon arc lamp type accelerated light resistance testing machine (manufactured by Toyo Seiki Seisaku-sho, Ltd., SUNTEST It was confirmed that in Ex. 7, 9 and 11 in which the present invention was used, excellent initial water/oil repellency, abrasion resistance and light resistance were achieved.

In Ex. 8 in which the compound (41c-1) having a hydrolyzable silyl group on both terminals of the poly(oxyperfluoroalkylene) chain comprising (CF$_2$O) and (CF$_2$CF$_2$O) via a linking group was used, the initial oil repellency, abrasion resistance and light resistance were inferior.

In Ex. 10 in which the compound (41c-2) having a hydrolyzable silyl group on one terminal of the poly(oxyperfluoroalkylene) chain comprising (CF₂O) and (CF₂CF₂O) via a linking group was used, the abrasion resistance and light resistance were inferior.

In Ex. 12 in which the compound (41c-3) having a hydrolyzable silyl group on one terminal of the poly(oxyperfluoroalkylene) chain comprising (CF₂CF₂O) and (CF₂CF₂CF₂CF₂O) via a linking group was used, the abrasion resistance and light resistance were inferior.

Ex. 13

Ex. 13-1

In a 500 mL three-necked flask, 40 g of HOCH₂CH₂CH₂CH₂CH₂CH₂OH, 59 g of a 48% KOH aqueous solution, 68 g of tert-butyl alcohol and 61 g of deionized water were put, and 23 g of CF₃CF₂CF₂—O—CF=CF₂ was added, followed by stirring in a nitrogen atmosphere. The mixture was washed once with a diluted aqueous hydrochloric acid solution, and the organic phase was recovered and concentrated under reduced pressure to obtain 27 g of crude product (51-1).

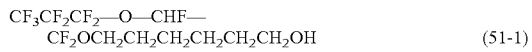
(51-1)

NMR Spectrum of compound (51-1):
¹H-NMR (300.4 MHz, solvent: CDCl₃, reference: TMS) δ (ppm): 1.3 (4H), 1.7 (4H), 2.5 (1H), 3.5 (2H), 3.9 (2H), 5.8 (1H).
¹⁹F-NMR (282.7 MHz, solvent: CDCl₃, reference: CFCl₃) δ (ppm): −82 (3F), −84 to 87 (2F), −89 (2F), −130 (2F), −146 (1F).

Ex. 13-2

Into a 500 mL three-necked flask, 29 g of the compound (51-1) obtained in Ex. 13-1, 294 g of AE-3000 and 12 g of triethylamine were put, and 19 g of p-toluenesulfonyl chloride was added, followed by stirring in a nitrogen atmosphere. The mixture was washed once with a diluted aqueous hydrochloric acid solution, and the organic phase was recovered, concentrated by an evaporator and purified by silica gel column chromatography to obtain 18 g of product (51-2). (OTs: —O—SO₂-Ph-CH₃)

CF₃CF₂CF₂—O—CHF—
CF₂OCH₂CH₂CH₂CH₂CH₂CH₂OTs          (51-2)

NMR Spectrum of compound (51-2):
¹H-NMR (300.4 MHz, solvent: CDCl₃, reference: TMS) δ (ppm): 1.3 (4H), 1.7 (4H), 2.5 (3H), 3.9 (2H), 4.0 (2H), 5.8 (1H), 7.1 to 7.8 (4H).
¹⁹F-NMR (282.7 MHz, solvent: CDCl₃, reference: CFCl₃) δ (ppm): −82 (3F), −84 to 87 (2F), −89 (2F), −130 (2F), −146 (1F).

Ex. 13-3

Into a 300 mL three-necked flask, 4 g of the compound (51-2) obtained in Ex. 13-2, 31 g of compound (60-1) (manufactured by Solvay Solexis, FLUOROLINK (registered trademark) D4000) and 160 g of 1,3-bis(trifluoromethyl)benzene were put, and 12 g of cesium carbonate was added, followed by stirring in a nitrogen atmosphere at 70° C. The solid was removed by filtration, the filtrate was washed with water, and the organic phase was recovered, concentrated under reduced pressure and purified by silica gel column chromatography to obtain 9 g of product (51-3).

HO—CH₂—(CF₂O){(CF₂O)ₓ₁(CF₂CF₂O)ₓ₂}—
CF₂—CH₂—OH          (60-1)

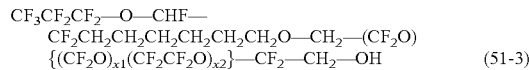
(51-3)

NMR Spectrum of compound (51-3):
¹H-NMR (300.4 MHz, solvent: CDCl₃, reference: TMS) δ (ppm): 1.3 (4H), 1.7 (4H), 2.5 (1H), 3.5 (2H), 3.8 (2H), 4.0 (2H), 4.2 (2H), 5.8 (1H).
¹⁹F-NMR (282.7 MHz, solvent: CDCl₃, reference: CFCl₃) δ (ppm): −52 to −56 (42F), −79 (1F), −80 (1F), −81 (1F), −82 (3F), −84 (1F), −85 to −88 (2F), −89 to −91 (82F), −130 (2F), −146 (1F).

Mean value of unit number x1: 21, mean value of unit number x2: 20, number average molecular weight of compound (51-3): 4,050.

Ex. 13-4

Into a 100 mL eggplant flask, 12 g of the compound (51-3) and 2.3 g of a sodium fluoride powder were put, and 9.3 g of CF₃CF₂CF₂OCF(CF₃)C(O)F was added, followed by stirring in a nitrogen atmosphere. The sodium fluoride powder was removed by filtration and excess CF₃CF₂CF₂OCF(CF₃)C(O)F was distilled off under reduced pressure to obtain 12 g of compound (51-4).

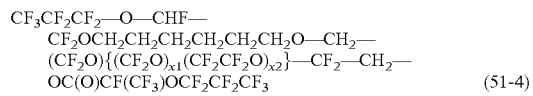
(51-4)

NMR Spectrum of compound (51-4):
¹H-NMR (300.4 MHz, solvent: CDCl₃, reference: TMS) δ (ppm): 1.3 (4H), 1.7 (4H), 2.5 (1H), 3.5 (2H), 4.0 (2H), 4.2 (2H), 4.7 (2H), 5.8 (1H).
¹⁹F-NMR (282.7 MHz, solvent: CDCl₃, reference: CFCl₃) δ (ppm): −52 to −56 (42F), −79 to −88 (16F), −89 to −91 (82F), −130 (4F), −133 (2F), −146 (1F).

Mean value of unit number x1: 21, mean value of unit number x2: 20, number average molecular weight of compound (51-4): 4,450.

Ex. 13-5

At a gas outlet of a 1 L nickel autoclave, a condenser maintained at 20° C., a NaF pellet packed layer and a condenser maintained at 0° C. were installed in series. A liquid returning line to return the solution collected from the condenser maintained at 0° C. to the autoclave was installed.

Into the autoclave, 750 g of ClCF₂CFClCF₂OCF₂CF₂Cl (hereinafter sometimes referred to as CFE-419) was put and stirred while maintaining the temperature at 25° C. Into the autoclave, nitrogen gas was blown at 25° C. for one hour, and then, 20% fluorine gas was blown at 25° C. for one hour at a flow rate of 2.0 L/hour. While blowing the 20% fluorine gas at the same flow rate, a solution having 6.0 g of the compound (51-4) dissolved in 54 g of CFE-419, was injected into the autoclave over a period of 1 hour. While blowing the 20% fluorine gas at the same flaw rate, the internal pressure of the autoclave was raised to 0.15 MPa (gauge pressure). Into the autoclave, 4 mL of a benzene solution containing 0.05 g/mL of benzene in CFE-419, was injected while heating to 40° C. from 25° C., and then the benzene solution inlet of the autoclave was closed. After stirring for 15 minutes, 4 mL of the benzene solution was again injected while maintaining the temperature at 40° C., and then the inlet was closed. The same operation was repeated three more times. The total amount of benzene injected was 0.17 g. While blowing the 20% fluorine gas at the same flow rate, stirring was continued for 1 hour. The pressure in the autoclave was brought to atmospheric pressure, and nitrogen gas was blown in for 1 hour. The content of the autoclave was concentrated by an evaporator to obtain 5.7 g of compound (51-5).

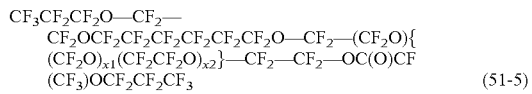

(51-5)

NMR Spectrum of compound (51-5):
$^{19}$F-NMR (282.7 MHz, solvent: CDCl$_3$, reference: CFCl$_3$) δ (ppm): −52 to −56 (42F), −79 to −88 (20F), −89 to −91 (90F), −121 (4F), −124 (4F), −130 (4F), −133 (1F).

Mean value of unit number x1: 21, mean value of unit number x2: 20, number average molecular weight of compound (51-5): 4,550.

Ex. 13-6

Into a round bottomed flask made of PFA, 5.7 g of the compound (51-5) and 10 g of AK-225 were put. The mixture was stirred while cooling in an ice bath, and in a nitrogen atmosphere, 10 g of methanol was slowly dropwise added from a dropping funnel, followed by stirring for 12 hours. The reaction mixture was concentrated by an evaporator to obtain 5.3 g of compound (51-6).

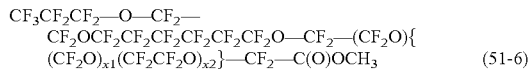

(51-6)

NMR Spectrum of compound (51-6):
$^{1}$H-NMR (300.4 MHz, solvent: CDCl$_3$, reference: TMS) δ (ppm): 3.9 (3H).
$^{19}$F-NMR (282.7 MHz, solvent CDCl$_3$, reference: CFCl$_3$) δ (ppm): −52 to −56 (42F), −79 to −88 (10F), −89 to −91 (90F), −121 (4F), −124 (4F), −130 (2F).

Mean value of unit number x1: 21, mean value of unit number x2: 20, number average molecular weight of compound (51-6): 4,200.

Ex. 13-7

Into a 50 mL eggplant flask, 4.7 g of the compound (51-6) obtained in Ex. 13-6, 0.3 g of H$_2$NCH$_2$C(CH$_2$CH=CH$_2$)$_3$ and 10 g of AC-6000 were put and stirred for 12 hours. The obtained reaction mixture was purified by silica gel column chromatography to obtain 3.1 g of compound (51-7).

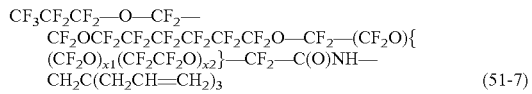

(51-7)

NMR Spectrum of compound (51-7):
$^{1}$H-NMR (300.4 MHz, solvent: CDCl$_3$, reference: TMS) δ (ppm): 2.1 (6H), 3.4 (2H), 5.2 (6H), 5.9 to 6.2 (3H)
$^{19}$F-NMR (282.7 MHz, solvent: CDCl$_3$, reference: CFCl$_3$) δ (ppm): −52 to −56 (42F), −79 to −88 (10F), −89 to −91 (90F), −121 (4F), −124 (4F), −130 (2F).

Mean value of unit number x1: 21, mean value of unit number x2: 20, number average molecular weight of compound (51-7): 3,700.

Ex. 13-8

Into a 10 mL PFA sample tube, 1.5 g of the compound (51-7) obtained in Ex. 13-7, 0.02 g of a xylene solution (platinum content: 3%) of a platinum/1,3-divinyl-1,1,3,3-tetramethyldisiloxane complex, 0.52 of HSi(OCH$_3$)$_3$, 0.01 g of aniline and 2.3 g of AC-6000 were put and stirred at 40° C. After completion of the reaction, the solvent, etc. were distilled off under reduced pressure, followed by filtration through a membrane filter having a pore size of 1.0 μm, to obtain 1.5 g of compound (51-8).

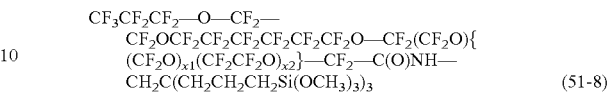

(51-8)

NMR Spectrum of compound (51-8):
$^{1}$H-NMR (300.4 MHz, solvent: CDCl$_3$, reference: TMS) δ (ppm): 0.75 (6H), 1.3 to 1.6 (12H), 3.4 (2H), 3.7 (27H).
$^{19}$F-NMR (282.7 MHz, solvent: CDCl$_3$, reference: CFCl$_3$) δ (ppm): −52 to −56 (42F), −79 to −88 (10F), −89 to −91 (90F), −121 (4F), −124 (4F), −130 (2F).

Mean value of unit number x1: 21, mean value of unit number x2: 20, number average molecular weight of compound (51-8): 3,700. The proportion of the unit (α) is 0.02 from m1=21, m2=22 and m6=1.

Ex. 14

Ex. 14-1

Into a 50 mL three-necked flask, 25 g of methanol and 0.5 g of potassium carbonate were put, and 8 g of the compound (32-2) was added, followed by stirring at room temperature for 12 hours. The mixture was concentrated and washed with a diluted aqueous hydrochloric acid solution, and the organic phase was recovered and concentrated to obtain 8 g of product (52-1).

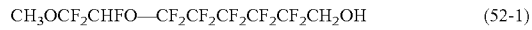

(52-1)

NMR Spectrum of compound (52-1):
$^{1}$H-NMR (300.4 MHz, solvent: CDCl$_3$, reference: TMS) δ (ppm): 3.7 (3H), 4.1 (2H), 6.0 (1H).
$^{19}$F-NMR (282.7 MHz, solvent: CDCl$_3$, reference: CFCl$_3$) δ (ppm): −85 (2F), −93 (2F), −123 (4F), −124 (2F), −126 (2F), −145 (1F).

Ex. 14-2

In accordance with the method disclosed in Patent Document 1 except that the compound (52-1) was used as methanol-added product, addition polymerization was conducted, followed by column purification to obtain compound (52-2).

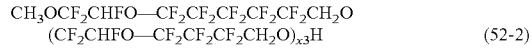

(52-2)

NMR Spectrum of compound (52-2):
$^{1}$H-NMR (300.4 MHz, solvent: CDCl$_3$, reference: TMS) δ (ppm): 3.7 (3H), 4.0 (2H), 4.4 (20H), 6.1 (11H).
$^{19}$F-NMR (282.7 MHz, solvent: CDCl$_3$, reference: CFCl$_3$) δ (ppm): −86 (20F), −91 (20F), −120 (2F), −121 (20F), −122 (2F), −123 (4F), −126 (2F), −128 (22F), −145 (11F).

Mean value of unit number x3: 10, number average molecular weight of compound (52-2): 3,190.

Ex. 14-3

In the same manner as in Ex. 1-2 except that 22 g of the compound (52-2) was used instead of the compound (22-1), the amount of the sodium fluoride powder was changed to 4.3 g, and the amount of CF$_3$CF$_2$CF$_2$OCF(CF$_3$)C(O)F was changed to 11.5 g, 24 g (yield: 97.3%) of compound (52-3) was obtained.

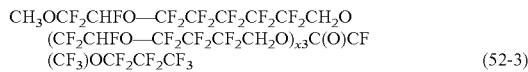

CH$_3$OCF$_2$CHFO—CF$_2$CF$_2$CF$_2$CF$_2$CF$_2$CH$_2$O
(CF$_2$CHFO—CF$_2$CF$_2$CF$_2$CH$_2$O)$_{x3}$C(O)CF
(CF$_3$)OCF$_2$CF$_2$CF$_3$      (52-3)

NMR Spectrum of compound (52-3):
$^1$H-NMR (300.4 MHz, solvent: CDCl$_3$, reference: TMS) δ (ppm): 3.7 (3H), 4.4 (20H), 4.8 (2H), 6.1 (11H).
$^{19}$F-NMR (282.7 MHz, solvent: CDCl$_3$, reference: CFCl$_3$) δ (ppm): −79 (1F), −81 (3F), −82 (3F), −86 (21F), −91 (20F), −120 (2F), −121 (22F), −122 (2F), −123 (2F), −126 (2F), −128 (22F), −131 (2F), −133 (1F), −145 (11F).
Mean value of unit number x3: 10, number average molecular weight of compound (52-3): 3500.

Ex. 14-4

In the same manner as in Ex. 1-3 except that 20.0 g of the compound (52-3) was used instead of the compound (23-1-1), 23.4 g (yield: 98.8%) of the compound (52-4) was obtained.

CF$_3$OCF$_2$CF$_2$O—CF$_2$CF$_2$CF$_2$CF$_2$CF$_2$CF$_2$O
(CF$_2$CF$_2$O—CF$_2$CF$_2$CF$_2$CF$_2$O)$_{x3}$C(O)CF(CF$_3$)
OCF$_2$CF$_2$CF$_3$      (52-4)

NMR Spectrum of compound (52-4):
$^{19}$F-NMR (282.7 MHz, solvent CDCl$_3$, reference: CFCl$_3$) δ (ppm): −56 (3F), −80 (1F), −82 (6F), −83 (40F), −84 (2F), −85 (38F), −87 (3F), −89 (40F), −89 (2F), −91 (2F), −122 (4F), −125 (42F), −130 (2F), −132 (1F).
Mean value of unit number x3: 10, number average molecular weight of compound (52-4): 4,150.

Ex. 14-5

In the same manner as in Ex. 1-4 except that 4.0 g of the compound (52-4) was used instead of the compound (24-1-1), and the amount of methanol was changed to 0.34 g, 3.6 g (yield: 94.8%) of compound (52-5) was obtained.

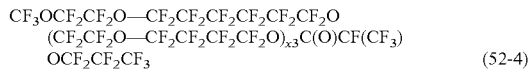

CF$_3$OCF$_2$CF$_2$O—CF$_2$CF$_2$CF$_2$CF$_2$CF$_2$CF$_2$O
(CF$_2$CF$_2$O—CF$_2$CF$_2$CF$_2$CF$_2$
O)$_{x3-1}$CF$_2$CF$_2$OCF$_2$CF$_2$CF$_2$C(O)OCH$_3$      (52-5)

NMR Spectrum of compound (52-5):
$^1$H-NMR (300.4 MHz, solvent: CDCl$_3$, reference: TMS) δ (ppm): 3.9 (3H).
$^{19}$F-NMR (282.7 MHz, solvent: CDCl$_3$, reference: CFCl$_3$) δ (ppm): −56 (3F), −84 (40F), −89 (40F), −91 (2F), −118 (2F), −122 (4F), −123 (4F), −124 (38F), −125 (2F).
Mean value of unit number x3-1: 9, number average molecular weight of compound (52-5): 3,830.

Ex. 14-6

In the same manner as in Ex. 1-5 except that 3.6 g of the compound (52-5) was used instead of the compound (12-1-1), and the amount of H$_2$NCH$_2$C(CH$_2$CH=CH$_2$)$_3$ was changed to 0.46 g, 2.9 g (yield: 78.4%) of compound (52-6) was obtained.

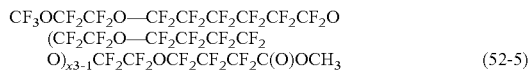

CF$_3$OCF$_2$CF$_2$O—CF$_2$CF$_2$CF$_2$CF$_2$CF$_2$CF$_2$O
(CF$_2$CF$_2$O—CF$_2$CF$_2$CF$_2$CF$_2$O)$_{x3-1}$
OCF$_2$CF$_2$OCF$_2$CF$_2$CF$_2$C(O)NHCH$_2$C
(CH$_2$CH=CH$_2$)$_3$      (52-6)

NMR Spectrum of compound (52-6):
$^1$H-NMR (300.4 MHz, solvent: CDCl$_3$, reference: TMS) δ (ppm): 2.1 (6H), 3.4 (2H), 5.2 (6H), 6.2 to 5.9 (3H).
$^{19}$F-NMR (282.7 MHz, solvent: CDCl$_3$, reference: CFCl$_3$) δ (ppm): −56 (3F), −81 (2F), −83 (2F), −84 (38F), −89 (40F), −91 (2F), −120 (2F), −122 (4F), −125 (4F), −126 (40F)
Mean value of unit number x3-1: 9, number average molecular weight of compound (52-6): 3,960.

Ex. 14-7

In the same manner as in Ex. 1-6 except that 2.9 g of the compound (52-6) was used instead of the compound (15c-1), the amount of the xylene solution (platinum content 3%) of a platinum/1,3-divinyl-1,1,3,3-tetramethyldisiloxane complex was changed to 0.008 g, the amount of HSi (OCH$_3$)$_3$ was changed to 0.30 g, and the amount of aniline was changed to 0.003 g, 2.71 g (yield: 99.1%) of compound (52-7) was obtained.

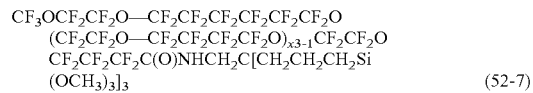

CF$_3$OCF$_2$CF$_2$O—CF$_2$CF$_2$CF$_2$CF$_2$CF$_2$CF$_2$O
(CF$_2$CF$_2$O—CF$_2$CF$_2$CF$_2$CF$_2$O)$_{x3-1}$CF$_2$CF$_2$O
CF$_2$CF$_2$CF$_2$C(O)NHCH$_2$C[CH$_2$CH$_2$CH$_2$Si
(OCH$_3$)$_3$]$_3$      (52-7)

NMR Spectrum of compound (52-7):
$^1$H-NMR (300.4 MHz, solvent: CDCl$_3$, reference: TMS) δ (ppm): 0.75 (6H), 1.3 to 1.6 (12H), 3.4 (2H), 3.7 (27H).
$^{19}$F-NMR (282.7 MHz, solvent: CDCl$_3$, reference: CFCl$_3$) δ (ppm): −56 (3F), −81 (2F), −83 (2F), −84 (38F), −89 (40F), −91 (2F), −120 (2F), −122 (4F), −125 (4F), −126 (40F)
Mean value of unit number x3: 9, number average molecular weight of compound (52-7): 4,320. The proportion of the unit (α) is 0.05 from m2=11, m4=9 and m6=1.

Ex. 15

Ex. 15-1

Into a 500 mL eggplant flask shielded by an aluminum foil, 1.2 g of sodium pyrithione and 50 g of 1,3-bistrifluoromethylbenzene (trade name: SR-solvent) were put, followed by stirring under cooling with ice. Then, 10.0 g of the compound (52-4) obtained in Ex. 14-4 was slowly added, followed by stirring for 2 hours under cooling with ice. 2.7 g of iodine and 0.4 g of 22-azobis(2-methylbutyronitrile) (trade name: V-59) were put, and the aluminum foil for shielding was removed, followed by stirring at 85° C. overnight. The temperature was returned to room temperature at 25° C., ethanol was added, followed by sufficient stirring, and AC-6000 was added for separation into two layers, the lower layer was recovered, and the solvent was distilled off. The obtained crude product was purified by silica gel column chromatography to obtain 7.9 g (yield: 85%) of compound (53-1).

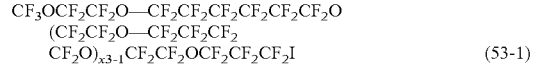

CF$_3$OCF$_2$CF$_2$O—CF$_2$CF$_2$CF$_2$CF$_2$CF$_2$CF$_2$O
(CF$_2$CF$_2$O—CF$_2$CF$_2$CF$_2$
CF$_2$O)$_{x3-1}$CF$_2$CF$_2$OCF$_2$CF$_2$CF$_2$I      (53-1)

NMR Spectrum of compound (53-1):
$^{19}$F-NMR (282.7 MHz, solvent: CDCl3, reference: CFCl3) δ (ppm): −55 (3F), −58 (2F), −81 (2F), −83 (40F), 488 (42F), −90 (2F), −116 (2F), −122 (4F), −125 (4F), −126 (38F).
Mean value of unit number x3-1: 9, number average molecular weight of compound (53-1): 3,820.

Ex. 15-2

Into a 50 mL eggplant flask, 7.9 g of the compound (53-1) obtained in Ex. 15-1, 0.017 g of an azo initiator AIBN (trade name, manufactured by Wako Pure Chemical Industries, Ltd.), 4.1 g of allyltributyltin and 7.9 g of SR-solvent were put, followed by stirring at 85° C. for 12 hours. The reaction crude liquid was washed with hexane and acetone, and the lower layer was recovered. The recovered lower layer was subjected to silica gel column, and the recovered solution was concentrated by an evaporator to obtain 6.9 g (yield: 87%) of compound (53-2).

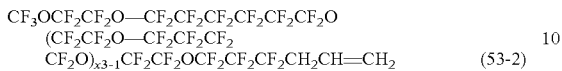
(53-2)

NMR Spectrum of compound (53-2):
$^1$H-NMR (300.4 MHz, solvent: CDCl$_3$, reference: TMS) δ (ppm): 2.8 (2H), 5.5 (2H), 5.8 (1H).
$^{19}$F-NMR (282.7 MHz, solvent: CDCl3, reference: CFCl3) δ (ppm): −55 (3F), −83 (40F), −88 (40F), −90 (2F), −114 (2F), −122 (4F), −125 (4F), −126 (38F), −127 (2F).

Mean value of unit number x3-1: 9, number average molecular weight of compound (53-2): 3,810.

Ex. 15-3

In the same manner as in Ex. 1-6 except that 6.7 g of the compound (53-2) was used instead of the compound (15c-1), the amount of the xylene solution (platinum content: 3%) of a platinum/1,3-divinyl-1,1,3,3-tetramethyldisiloxane complex was changed to 0.023 g, 2.38 g of HSiC was used instead of HSi(OCH$_3$)$_3$, and no aniline was used, 7.4 g (yield: 99.3%) of compound (53-3) was obtained.

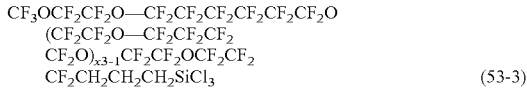
(53-3)

Ex. 15-4

Into a 50 mL eggplant flask, 7.4 g of the compound (53-3) obtained in Ex. 15-3 and 7.4 g of AC-2000 were put. The mixture was stirred under cooling in an ice bath, and in a nitrogen atmosphere, 10.5 mL of allyl magnesium chloride (1.0 moVL, tetrahydrofuran solution) was slowly dropwise added. The temperature was returned to room temperature, followed by stirring for 12 hours, and a diluted aqueous hydrochloric acid solution was added, followed by sufficient stirring, and AC-2000 was added for separation into two phases, the lower layer was recovered, and the solvent was distilled off. The obtained crude product was subjected to silica gel column, and the recovered solution was concentrated by an evaporator to obtain 5.3 g (yield: 71.9%) of compound (53-4).

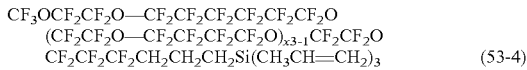
(53-4)

NMR Spectrum of compound (53-4):
$^1$H-NMR (300.4 MHz, solvent: CDCl$_3$, reference: TMS) δ (ppm): 0.9 (2H), 1.7 (6H), 1.9 (2H), 2.3 (2H), 5.0 (6H), 6.0 (3H).
$^{19}$F-NMR (282.7 MHz, solvent: CDCl3, reference: CFCl3) δ (ppm): −55 (3F), −83 (40F), −88 (40F), −90 (2F), −114 (2F), −122 (4F), −125 (4F), −126 (38F), −127 (2F).

Mean value of unit number x3-1: 9, number average molecular weight of compound (53-4): 4,210.

Ex. 15-5

In the same manner as in Ex. 1-6 except that 2.0 g of compound (53-4) was used instead of the compound (15c-1), the amount of the xylene solution (platinum content 3%) of a platinum/1,3-divinyl-1,1,3,3-tetramethyldisiloxane complex was changed to 0.007 g, the amount of HSi (OCH$_3$)$_3$ was changed to 0.23 g, and the amount of aniline was changed 0.002 g, 2.2 g (yield: 99.3%) of compound (53-5) was obtained.

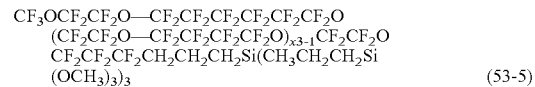
(53-5)

NMR Spectrum of compound (53-5):
$^1$H-NMR (300.4 MHz, solvent: CDCl$_3$, reference: TMS) δ (ppm): 0.8 (14H), 1.6 (8H), 2.1 (2H), 3.6 (27H).
$^{19}$F-NMR (282.7 MHz, solvent: CDCl3, reference: CFCl3) δ (ppm): −55 (3F), −83 (40F), −88 (40F), −90 (2F), −114 (2F), −122 (4F), −125 (4F), −126 (38F), −127 (2F).

Mean value of unit number x3-1: 9, number average molecular weight of compound (53-5): 4,570. The proportion of the unit (α) is 0.05 from m2=11, m4=9 and m6=1.

Ex. 16

Ex. 16-1

In accordance with the method disclosed in Patent Document 1, Ex. 6 except that the amount of methanol-added product was changed to 3 g, the amount of the compound (32-2) was changed to 5.5 g, and 1.0 g of potassium carbonate was used instead of potassium hydroxide, the compound (32-2) was subjected to addition polymerization, followed by column purification to obtain compound (54-1).

(54-1)

NMR Spectrum of compound (54-1):
$^1$H-NMR (300.4 MHz, solvent: CDCl$_3$, reference: TMS) δ (ppm): 3.7 (3H), 4.0 (2H), 4.4 (18H), 6.1 (10H).
$^{19}$F-NMR (282.7 MHz, solvent: CDCl$_3$, reference: CFCl$_3$) δ (ppm): −86 (6F), −91 (6F), −121 (4F), −122 (6F), −123 (2F), −126 (6F), −145 (3F).

Mean value of unit number x3: 3, number average molecular weight of compound (54-1): 1,170.

Ex. 16-2

In accordance with the method disclosed in Patent Document 1, Ex. 6, except that 6.6 g of the compound (54-1) was used instead of the methanol-added product, the amount of the compound (32-2) was changed to 5.5 g, the amount of the compound (11a) was changed to 11.7 g, and 0.7 g of potassium carbonate was used instead of potassium hydroxide, the compound (11a) was subjected to addition polymerization, followed by column purification to obtain compound (54-2).

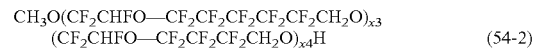
(54-2)

NMR Spectrum of compound (54-2):
$^1$H-NMR (300.4 MHz, solvent: CDCl$_3$, reference: TMS) δ (ppm): 3.7 (3H), 4.0 (2H), 4.4 (18H), 6.1 (10H).
$^{19}$F-NMR (282.7 MHz, solvent CDCl$_3$, reference: CFCl$_3$) δ (ppm): −86 (20F), −91 (20F), −120 (6F), −121 (14F), −122 (6F), −123 (8F), −126 (6F), −128 (−14F), −145 (10F).

Mean value of unit number x3: 3, mean value of unit number x4: 7, number average molecular weight of compound (54-2): 3,110.

Ex. 16-3

In the same manner as in Ex. 1-2 except that 7.6 g of the compound (54-2) was used instead of the compound (22-1), the amount of the sodium fluoride powder was changed to 1.5 g, and the amount of CF$_3$CF$_2$CF$_2$OCF(CF$_3$)C(O)F was changed to 4.0 g, 8.2 g (yield: 97.9%) of compound (54-3) was obtained.

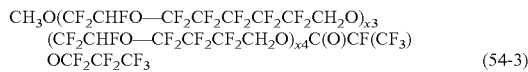
(54-3)

NMR Spectrum of compound (54-3):
$^1$H-NMR (300.4 MHz, solvent: CDCl$_3$, reference: TMS) δ (ppm): 3.7 (3H), 4.4 (20H), 4.8 (2H), 6.1 (10H).
$^{19}$F-NMR (282.7 MHz, solvent: CDCl$_3$, reference: CFCl$_3$) (ppm): −79 (1F), −81 (3F), −82 (3F), −86 (21F), −91 (20F), −120 (6F), −121 (14F), −122 (6F), −123 (6F), −126 (6F), −128 (−14F), −131 (2F), −133 (1F), −145 (10F).

Mean value of unit number x3: 3, mean value of unit number x4: 7, number average molecular weight of compound (54-3): 3,430.

Ex. 16-4

In the same manner as in Ex. 1-3 except that 8.2 g of the compound (54-3) was used instead of the compound (23-1-1), 9.5 g (yield: 98.6%) of compound (54-4) was obtained.

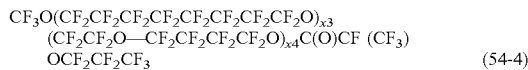
(54-4)

NMR Spectrum of compound (54-4):
$^{19}$F-NMR (282.7 MHz, solvent: CDCl$_3$, reference: CFCl$_3$) δ (ppm): −56 (3F), −80 (1F), −82 (6F), −83 (40F), −84 (2F), −85 (38F), −87 (3F), −89 (40F), −89 (2F), −91 (2F), −122 (12F), −125 (42F), −130 (2F), −132 (1F).

Mean value of unit number x3: 3, mean value of unit number x4: 7, number average molecular weight of compound (54-4): 4,040.

Ex. 16-5

In the same manner as in Ex. 1-4 except that 4.0 of the compound (54-4) was used instead of the compound (24-1-1), and the amount of methanol was changed to 0.4 g, 3.7 g (yield: 99.5%) of compound (54-5) was obtained.

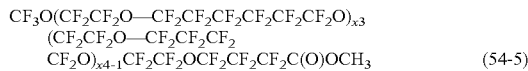
(54-5)

NMR Spectrum of compound (54-5):
$^1$H-NMR (300.4 MHz, solvent: CDCl$_3$, reference: TMS) δ (ppm): 3.9 (3H).
$^{19}$F-NMR (282.7 MHz, solvent: CDCl$_3$, reference: CFCl$_3$) δ (ppm): −56 (3F), −84 (40F), −89 (40F), −91 (2F), −118 (2F), −122 (12F), −123 (12F), −124 (−26F), −125 (2F).

Mean value of unit number x3: 3, mean value of unit number x4-1: 6, number average molecular weight of compound (54-5): 3,760.

Ex. 16-6

In the same manner as in Ex. 1-5 except that 3.7 g of the compound (54-5) was used instead of the compound (12-1-1) and the amount of H$_2$NCH$_2$C(CH$_2$CH=CH$_2$)$_3$ was changed to 0.47 g, 2.9 g (yield: 75.6%) of compound (54-6) was obtained.

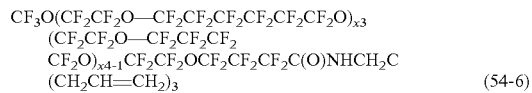
(54-6)

NMR Spectrum of compound (54-6):
$^1$H-NMR (300.4 MHz, solvent: CDCl$_3$, reference: TMS) δ (ppm): 2.1 (6H), 3.4 (2H), 5.2 (6H), 6.2 to 5.9 (3H).
$^{19}$F-NMR (282.7 MHz, solvent CDCl$_3$, reference: CFCl$_3$) δ (ppm): −56 (3F), −81 (2F), −83 (2F), −84 (38F), −89 (40F), −91 (2F), −120 (2F), −122 (12F), −125 (12F), −126 (28F)

Mean value of unit number x3: 3, mean value of unit number x4-1: 6, number average molecular weight of compound (54-6): 3,890.

Ex. 16-7

In the same manner as in Ex. 1-6 except that 2.9 g of the compound (54-6) was used instead of the compound (15c-1), the amount of the xylene solution (platinum content: 3%) of a platinum/1,3-divinyl-1,1,3,3-tetramethyldisiloxane complex was changed to 0.08 g, the amount of HSi(OCH$_3$)$_3$ was changed to 0.30 g, and the amount of aniline was changed to 0.003 g, 2.68 g (yield: 98.6%) of compound (54-7) was obtained.

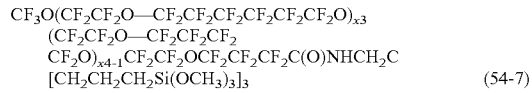
(54-7)

NMR Spectrum of compound (54-7):
$^1$H-NMR (300.4 MHz, solvent: CDCl$_3$, reference: TMS) δ (ppm): 0.75 (6H), 1.3 to 1.6 (12H), 3.4 (2H), 3.7 (27H).
$^{19}$F-NMR (282.7 MHz, solvent: CDCl$_3$, reference: CFCl$_3$) δ (ppm): −56 (3F), −81 (2F), −83 (2F), −84 (38F), −89 (40F), −91 (2F), −120 (2F), −122 (12F), −125 (12F), −126 (28F)

Mean value of unit number x3: 3, mean value of unit number x4-1: 6, number average molecular weight of compound (54-7): 4,250. The proportion of the unit (α) is 0.16 from m2=10, m4=6 and m6=3.

Ex. 17 to 20: Production and Evaluation of Article

Using the compound obtained in each of Ex. 13 to 16, surface treatment of a substrate was conducted to obtain an article in each of Ex. 17 to 20. As the surface treatment method, in each Ex., the same dry coating method and wet coating method as in Ex. 7 to 12 were employed. As the substrate, chemically tempered glass was used. The obtained articles were evaluated in the same manner as in Ex. 7 to 12. The results are shown in Table 2.

As shown in Table 2, it was confirmed that the fluorinated polyether compound in each of Ex. 17 to 20 was excellent in the initial water/oil repellency, abrasion resistance and light resistance.

TABLE 2

| Ex. | | | 17 | 18 | 19 | 20 |
|---|---|---|---|---|---|---|
| Fluorinated ether compound | | | Compound (51-8) | Compound (52-7) | Compound (53-5) | Compound (54-7) |
| Dry coating | Initial contact angle | Water | ◉ | ◉ | ◉ | ◉ |
| | | n-Hexadecane | ◉ | ◉ | ◉ | ◉ |

TABLE 2-continued

| Ex. | | 17 | 18 | 19 | 20 |
|---|---|---|---|---|---|
| method | Abrasion resistance (steel wool) | ◯ | ◯ | ◯ | ◯ |
| | Abrasion resistance (eraser) | ◯ | Δ | Δ | Δ |
| | Fingerprint stain removability | ◉ | ◉ | ◉ | ◉ |
| | Light resistance | Δ | Δ | ◯ | ◯ |
| | Lubricity | ◉ | Δ | Δ | Δ |
| Wet coating method | Initial contact angle Water | ◉ | ◉ | ◉ | ◉ |
| | n-Hexadecane | ◉ | ◉ | ◉ | ◉ |
| | Abrasion resistance (steel wool) | ◯ | ◯ | ◯ | Δ |
| | Abrasion resistance (eraser) | ◯ | Δ | Δ | Δ |
| | Fingerprint stain removability | ◉ | ◉ | ◉ | ◉ |
| | Light resistance | Δ | Δ | ◯ | ◯ |
| | Lubricity | ◉ | Δ | Δ | Δ |

INDUSTRIAL APPLICABILITY

The fluorinated ether compound of the present invention is useful for various applications for which it is required to impart lubricity and water/oil repellency. For example, it may be used for a display input device such as a touch panel; surface protective coating on a transparent glass or transparent plastic member, kitchen antifouling coating; water repellent moistureproof coating or antifouling coating on electronic device, a heat exchanger or a battery; toiletry antifouling coating; coating on a member which requires liquid repellency while conducting electricity; water repellent/waterproof/water sliding coating on a heat exchanger; or a surface low friction coating on the inside of a vibrating strainer or a cylinder, etc. More specific examples of application include a front protective plate, an antireflection plate, a polarizing plate, an antiglare plate or a surface thereof having an antireflection film, of a display, an apparatus having a display input apparatus of which the screen is operated by human fingers or hands, such as a touch panel sheet or a touch panel display of an apparatus such as a mobile phone or a personal digital assistant, a decorative building material for restroom, bathroom, lavatory, kitchen and the like, waterproof coating for a wiring board, water repellent/waterproof coating on a heat exchanger, water repellent coating on a solar cell, waterproof/water repellent coating on a printed wiring board, waterproof/water repellent coating for an electronic equipment casing or an electronic member, insulating property-improving coating on a power transmission line, waterproof/water repellent coating on a filter, waterproof coating on an electromagnetic wave absorption material or an acoustic material, antifouling coating for bathroom, kitchen instrument and toiletry, water repellent/waterproof/water sliding coating on a heat exchanger, surface low-friction coating on the inside of a vibrating strainer or a cylinder, surface protective coating on a machine component, a vacuum apparatus component, a bearing component, an automobile component, an industrial tool, etc.

This application is a continuation of PCT Application No. PCT/JP2018/019371, filed on May 18, 2018, which is based upon and claims the benefit of priority from Japanese Patent Application No. 2017-104731 filed on May 26, 2017. The contents of those applications are incorporated herein by reference in their entireties.

The invention claimed is:

1. A fluorinated ether compound having a poly(oxyperfluoroalkylene) chain having a unit (α) which is an oxyperfluoroalkylene unit having 5 or 6 carbon atoms, and a unit (β) which is an oxyperfluoroalkylene unit having at most 4 carbon atoms, and having at least one of a hydrolysable silyl group and a silanol group on both terminals of the poly(oxyperfluoroalkylene) chain via a linking group,
wherein in the poly(oxyperfluoroalkylene) chain, a proportion of a number of the unit (α) to a total number of the unit (α) and the unit (β) is from 0.02 to 0.2.

2. The fluorinated ether compound according to claim 1, wherein in the poly(oxyperfluoroalkylene) chain, the proportion of the number of the unit (α) to the total number of the unit (α) and the unit (β) is from 0.02 to 0.16.

3. The fluorinated ether compound according to claim 1, wherein the poly(oxyperfluoroalkylene) chain contains a structure having the unit (α) and the unit (β) alternately arranged.

4. The fluorinated ether compound according to claim 1, wherein the unit (α) is $(CF_2CF_2CF_2CF_2CF_2O)$ or $(CF_2CF_2CF_2CF_2CF_2CF_2O)$.

5. The fluorinated ether compound according to claim 1, wherein the unit (β) is $(CF_2O)$ or $(CF_2CF_2O)$.

6. The fluorinated ether compound according to claim 1, which is a compound represented by the following formula (11):

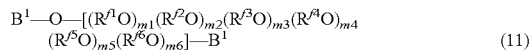

wherein
$R^{f1}$ is a $C_1$ perfluoroalkylene group,
$R^{f2}$ is a $C_2$ perfluoroalkylene group,
$R^{f3}$ is a $C_3$ perfluoroalkylene group,
$R^{f4}$ is a $C_4$ perfluoroalkylene group,
$R^{f5}$ is a $C_5$ perfluoroalkylene group,
$R^{f6}$ is a $C_6$ perfluoroalkylene group,
m1, m2, m3, m4, m5 and m6 are each 0 or an integer of at least 1, m1+m2+m3+m4 is an integer of at least 1, m5+m6 is an integer of at least 1, and m1+m2+m3+m4+m5+m6 is an integer of from 2 to 200,
$B^1$ is $-Q[-SiR_nL_{3-n}]_k$,
Q is a (k+1) valent linking group,
R is a hydrogen atom or a monovalent hydrocarbon group,
L is a hydrolysable group or a hydroxy group,
n is an integer of from 0 to 2, and
k is an integer of from 1 to 10.

7. The fluorinated ether compound according to claim 6, wherein $B^1$ is a group represented by any one of the following formulae (g1) to (g7):

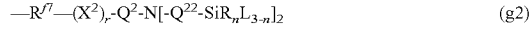

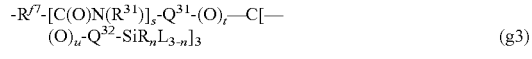

$$-R^{f7}-[C(O)N(R^5)]_v-Q^{51}-Z[-Q^{52}-SiR_nL_{3-n}]_w \quad (g5)$$

$$-R^{f7}-Q^{61}-G(R^6)[-Q^{62}-SiR_nL_{3-n}]_2 \quad (g6)$$

$$-R^{f7}-Q^{71}-[CH_2C(R^{71})(-Q^{72}-SiR_nL_{3-n})]_y-R^{72} \quad (g7)$$

wherein $R^{f7}$ is a $C_{1-6}$ perfluoroalkylene group,

R is a hydrogen atom or a monovalent hydrocarbon group,

L is a hydrolysable group or a hydroxy group, n is an integer of from 0 to 2, in the formula (g1), $X^1$ is an etheric oxygen atom or —C(O)N($R^1$)— provided that N is bonded to $Q^1$, R is a hydrogen atom or an alkyl group, p is 0 or 1, and $Q^1$ is an alkylene group, a group having an etheric oxygen atom or a silphenylene skeleton between carbon atoms of an alkylene group having at least 2 carbon atoms, or a group having a bivalent organopolysiloxane residue or a dialkylsilylene group between carbon atoms or at a terminal on the side bonded to $(X^1)_p$ of an alkylene group having at least 2 carbon atoms, in the formula (g2), $X^2$ is an etheric oxygen atom, —NH— or —C(O)N($R^2$)— provided that N is bonded to $Q^{21}$, $R^2$ is a hydrogen atom or an alkyl group, r is 0 or 1 provided that it is 0 when $Q^{21}$ is a single bond, $Q^{21}$ is a single bond, an alkylene group, or a group having an etheric oxygen atom, —NH—, —C(O)—, —C(O)O— or —OC(O)— between carbon atoms of an alkylene group having at least 2 carbon atoms, $Q^{22}$ is an alkylene group, or a group having an etheric oxygen atom, —NH— or a bivalent organopolysiloxane residue between carbon atoms of an alkylene group having at least 2 carbon atoms, and two $[-Q^{22}-SiR_nL_{3-n}]$ may be the same or different, in the formula (g3), $R^{31}$ is a hydrogen atom or an alkyl group, s is 0 or 1, $Q^{31}$ is a single bond, an alkylene group, or a group having an etheric oxygen atom between carbon atoms of an alkylene group having at least 2 carbon atoms, t is 0 or 1 provided that it is 0 when $Q^{31}$ is a single bond, u is 0 or 1, $Q^{32}$ is an alkylene group, a group having an etheric oxygen atom or a silphenylene skeleton between carbon atoms of an alkylene group having at least 2 carbon atoms, or a group having —C(O)N($R^{32}$)—, a bivalent organopolysiloxane residue or a dialkylsilylene group between carbon atoms or at a terminal on the side bonded to $(O)_u$ of an alkylene group having at least 2 carbon atoms, $R^{32}$ is a hydrogen atom or an alkyl group, and three $[—(O)_u-Q^{32}-SiR_nL_{3-n}]$ may be the same or different, in the formula (g4), $Q^{41}$ is an alkylene group, or a group having an etheric oxygen atom between carbon atoms of an alkylene group having at least 2 carbon atoms, $Q^{42}$ is an alkylene group, or a group having an etheric oxygen atom or a bivalent organopolysiloxane residue between carbon atoms of an alkylene group having at least 2 carbon atoms, and three $[-Q^{42}-SiR_nL_{3-n}]$ may be the same or different, in the formula (g5), $R^5$ is a hydrogen atom or an alkyl group, v is 0 or 1, $Q^{51}$ is an alkylene group, or a group having an etheric oxygen atom between carbon atoms of an alkylene group having at least 2 carbon atoms, Z is a (w+1) valent organopolysiloxane residue, $Q^{52}$ is an alkylene group, or a group having an etheric oxygen atom or a bivalent organopolysiloxane residue between carbon atoms of an alkylene group having at least 2 carbon atoms, w is an integer of from 2 to 7, and w $[-Q^{52}-SiR_nL_{3-n}]$ may be the same or different, in the formula (g6), $Q^{61}$ is a single bond, an alkylene group, or a group having an etheric oxygen atom between carbon atoms of an alkylene group having at least 2 carbon atoms, G is a carbon atom or a silicon atom, $R^6$ is a hydroxy group or an alkyl group, $Q^{62}$ is an alkylene group, or a group having an etheric oxygen atom or a bivalent organopolysiloxane residue between carbon atoms of an alkylene group having at least 2 carbon atoms, and two $[-Q^{62}-SiR_nL_{3-n}]$ may be the same or different, and in the formula (g7), $Q^{71}$ is a single bond, an alkylene group, or a group having an etheric oxygen atom between carbon atoms of an alkylene group having at least 2 carbon atoms, $R^{71}$ is a hydrogen atom or an alkyl group, $Q^{72}$ is a single bond or an alkylene group, $R^{72}$ is a hydrogen atom or a halogen atom, y is an integer of from 1 to 10, and two to ten $[-Q^{72}-SiR_nL_{3-n}]$ may be the same or different.

8. A fluorinated ether composition, comprising at least one of the fluorinated ether compound according to claim 1, and at least one other fluorinated ether compound.

9. A coating liquid comprising the fluorinated ether composition according to claim 8, and a liquid medium.

10. A method for producing an article, which comprises applying the coating liquid according to claim 9 by wet coating method to a surface of a substrate, and removing the liquid medium, to form a surface layer on the surface of the substrate.

11. An article having a surface layer formed of the fluorinated ether composition according to claim 8, on a surface of a substrate.

12. A method for producing an article, which comprises treating a surface of a substrate by dry coating method using the fluorinated ether composition according to claim 8 to form a surface layer on the surface of the substrate.

13. A coating liquid comprising the fluorinated ether compound according to claim 1, and a liquid medium.

14. A method for producing an article, which comprises applying the coating liquid according to claim 13 by wet coating method to a surface of a substrate, and removing the liquid medium, to form a surface layer on the surface of the substrate.

15. An article having a surface layer formed of the fluorinated ether compound according to claim 1, on a surface of a substrate.

16. A method for producing an article, which comprises treating a surface of a substrate by dry coating method using the fluorinated ether compound according to claim 1 to form a surface layer on the surface of the substrate.

* * * * *